(12) United States Patent
Wu et al.

(10) Patent No.: US 10,081,838 B2
(45) Date of Patent: Sep. 25, 2018

(54) GENE EXPRESSION SIGNATURE FOR IL-6/STAT3 SIGNALING PATHWAY AND USE THEREOF

(71) Applicants: Zhong Wu, Poolesville, MD (US); Martin Schlumpberger, Solingen (DE); John Dicarlo, Bethesda, MD (US); Vikram Devgan, Frederick, MD (US); Yexun Wang, Ellicott City, MD (US)

(72) Inventors: Zhong Wu, Poolesville, MD (US); Martin Schlumpberger, Solingen (DE); John Dicarlo, Bethesda, MD (US); Vikram Devgan, Frederick, MD (US); Yexun Wang, Ellicott City, MD (US)

(73) Assignee: QIAGEN SCIENCES, LLC, Germantown, MD (US)

( * ) Notice: Subject to any disclaimer, the term of this patent is extended or adjusted under 35 U.S.C. 154(b) by 313 days.

(21) Appl. No.: 14/398,532

(22) PCT Filed: May 3, 2013

(86) PCT No.: PCT/US2013/039445
§ 371 (c)(1),
(2) Date: Nov. 3, 2014

(87) PCT Pub. No.: WO2013/166373
PCT Pub. Date: Nov. 7, 2013

(65) Prior Publication Data
US 2015/0232926 A1 Aug. 20, 2015

Related U.S. Application Data

(60) Provisional application No. 61/642,037, filed on May 3, 2012.

(51) Int. Cl.
*C12Q 1/6876* (2018.01)
*C12Q 1/6883* (2018.01)

(52) U.S. Cl.
CPC ..... *C12Q 1/6876* (2013.01); *C12Q 2600/158* (2013.01); *C12Q 2600/16* (2013.01)

(58) Field of Classification Search
CPC ............... C12Q 1/6876; C12Q 1/6883; C12Q 2600/112; C12Q 2600/118; C12Q 2600/158; C12Q 2600/16
See application file for complete search history.

(56) References Cited

U.S. PATENT DOCUMENTS

| | | | | |
|---|---|---|---|---|
| 7,939,263 B2* | 5/2011 | Clarke | .................. | C12N 5/0693 435/6.12 |
| 2003/0154032 A1* | 8/2003 | Pittman | .............. | C07K 14/4713 702/20 |
| 2003/0219796 A1* | 11/2003 | Nagata | .................. | C12Q 1/6883 435/6.11 |
| 2005/0118625 A1* | 6/2005 | Mounts | ................ | C12Q 1/6837 435/6.14 |
| 2005/0272080 A1* | 12/2005 | Palma | .................. | C12Q 1/6883 435/6.11 |
| 2006/0275294 A1 | 12/2006 | Omoigui | | |
| 2007/0054275 A1* | 3/2007 | Dogulu | ................ | C12Q 1/6883 435/5 |
| 2007/0243546 A1* | 10/2007 | Cao | ....................... | C12Q 1/6837 435/6.12 |

(Continued)

FOREIGN PATENT DOCUMENTS

WO   WO 10/040571   * 4/2010
WO   WO 10/135669   * 11/2010

(Continued)

OTHER PUBLICATIONS

Fujitani et al. "Transcriptional activation of the IL-6 response element in the junB promoter is mediated by multiple Stat family proteins." Biochemical and biophysical research communications. Jul. 29, 1994;202(2):1181-7.
Wang L, et al. "IL-17 can promote tumor growth through an IL-6-Stat3 signaling pathway," J Exp Med. Jul. 6, 2009;206 (7):1457-64.
Bonetto A, et al. "STAT3 activation in skeletal muscle links muscle wasting and the acute phase response in cancer cachexia," PLoS One. 2011;6(7):e22538.
Bluyssen HA, et al. "IFN gamma-dependent SOCS3 expression inhibits IL-6-induced STAT3 phosphorylation and differentially affects IL-6 mediated transcriptional responses in endothelial cells," Am J Physiol Cell Physiol. Aug. 2010;299(2):C354-62.
Tsuruma R, et al. "Physical and functional interactions between STAT3 and KAP1," Oncogene. May 8, 2008;27 (21):3054-9.

(Continued)

*Primary Examiner* — Kevin Kai Hill
(74) *Attorney, Agent, or Firm* — Robin L. Teskin; LeClairRyan LLP

(57) ABSTRACT

The present invention relates to a set of biomarkers, microarrays that provide for detection thereof, an expression signature comprising 16 genes or a subset thereof, and the use thereof in determining the regulation status of IL-6/STAT3 signaling pathway in a cell sample or subject, as well as compositions for the detection thereof. The regulation status of IL-6/STAT3 signaling pathway in a cell sample or subject may be assayed based on the level of expression of one or more of these genes. The methods and compositions provided herein may be used to evaluate IL-6/STAT3 pathway regulation status in a sample; classify a cell sample as having a deregulated or regulated IL-6/STAT3 signaling pathway; determine whether an agent modulates the IL-6/STAT3 signaling pathway; predict the response of a subject to an agent that modulates the IL-6/STAT3 signaling pathway; assign treatment to a subject; and/or evaluate the pharmacodynamic effects of therapies designed to regulate IL-6/STAT3 pathway signaling. Expression of the biomarkers is preferably determined by RT-PCR using SYBR Green methods, and the expression data analyzed and compared to a control sample by use of the random forest method.

9 Claims, 9 Drawing Sheets

Figure 1:
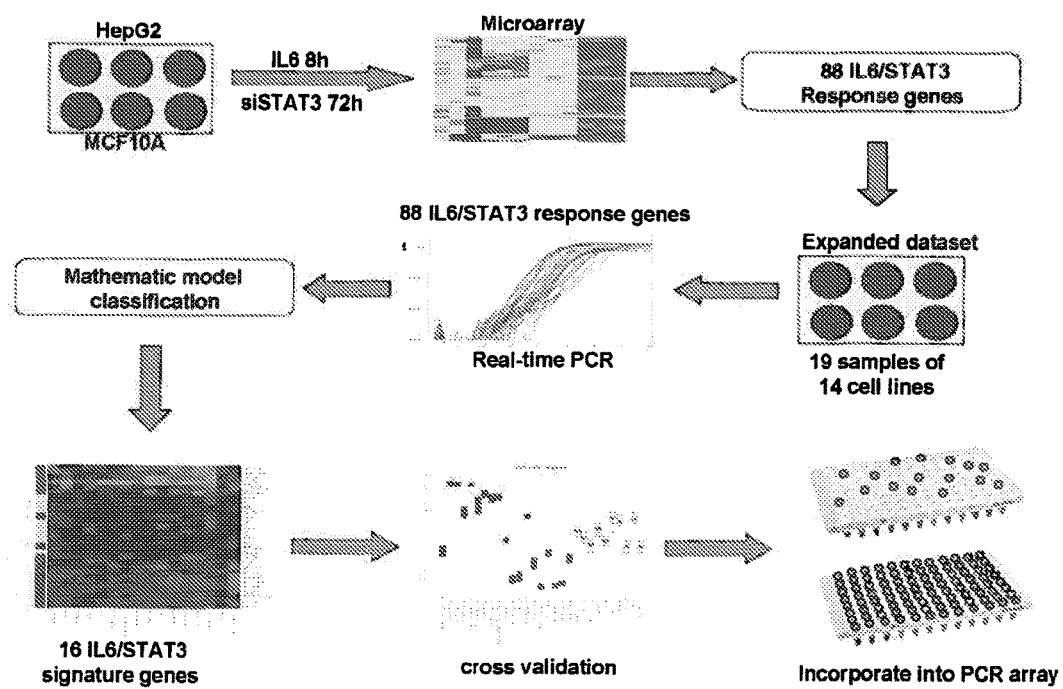

Specification includes a Sequence Listing.

(56) References Cited

U.S. PATENT DOCUMENTS

| | | | |
|---|---|---|---|
| 2008/0226645 A1* | 9/2008 | O'Toole | C12Q 1/6883 514/1.1 |
| 2012/0065125 A1 | 3/2012 | Yu et al. | |
| 2013/0345086 A1* | 12/2013 | Isaacs | C12Q 1/6883 506/9 |

FOREIGN PATENT DOCUMENTS

| | | | |
|---|---|---|---|
| WO | 2011100685 | | 8/2011 |
| WO | WO 12/110793 | * | 8/2012 |

OTHER PUBLICATIONS

Taub R. "Hepatoprotection via the IL-6/Stat3 pathway," J Clin Invest. Oct. 2003;112(7):978-80.

Lin CM, et al. "Chrysin suppresses IL-6-induced angiogenesis via down-regulation of JAK1/STAT3 and VEGF: an in vitro and in ovo approach," J Agric Food Chem. Jun. 9, 2010;58(11):7082-7.

Pflegerl P, et al. "Epidermal loss of JunB leads to a SLE phenotype due to hyper IL-6 signaling," Proc Natl Acad Sci U S A. Dec. 1, 2009;106(48):20423-8.

Yoon S, et al. "STAT3 transcriptional factor activated by reactive oxygen species induces IL6 in starvation-induced autophagy of cancer cells," Autophagy. Nov. 2010;6(8):1125-38.

Haga S, et al. "Stat3 protects against Fas-induced liver injury by redox-dependent and -independent mechanisms," J Clin Invest. Oct. 2003;112(7):989-98.

Zhang et al., "ZIP4 regulates pancreatic cancer cell growth by activating IL-6/STAT3 pathway through zinc finger transcription factor CREB." *Clinical Cancer Research*. 16(5) (2010): 1423-1430.

Yang et al., "Roles of unphosphorylated STATs in signaling." *Cell research*. 18(4) (2008): 443-451.

Wakefield et al., "Bcl3 selectively promotes metastasis of ERBB2-driven mammary tumours." *Cancer research*. 73(2) (2012): 745-755.

Lee et al., "Interleukin-6 induces proinflammatory signaling in Schwann cells: a high-throughput analysis." *Biochemical and biophysical research communications*. 382(2) (2009): 410-414.

Hartman et al., "HER2 overexpression elicits a proinflammatory IL-6 autocrine signaling loop that is critical for tumorigenesis," *Cancer research*. 71(13) (2011): 4380-4391.

* cited by examiner

FIG. 6A

| Well Position | Gene symbol | Primer_F | SEQ ID NO | Primer_R | SEQ ID NO |
|---|---|---|---|---|---|
| A01 | ACSL3 | GGAGTGTTAGGAGCAGCCAG | 1 | CATACGATGTTTGTGATGCAAC | 2 |
| A02 | ADFP | TCCTGTCCAACATCCAAGGTG | 3 | TTGCTAGAAGTGAGGAGGCTG | 4 |
| A03 | ARFGAP3 | GTGAAAGGTGTTGCTGTTTG | 5 | AATGACTGTTCTCCCATACACG | 6 |
| A04 | BTBD11 | GTATCCTCAGAGATGCTGCGTG | 7 | TGACAGAGAAAGCACACCAAATG | 8 |
| A05 | C20orf46 | CCTCCTTCCCAATGGCATC | 9 | AGCTGCCCAGTCTCGTGTTC | 10 |
| A06 | C8A | TCAATCCATGACCAGGGAG | 11 | ATTGTTTCAGGTGTCTGCTTG | 12 |
| A07 | CASP4 | GAGAGACAGCACAATGGGCTC | 13 | CTTCCGAAATACTTCCTCTAGGTG | 14 |
| A08 | CD14 | CCAGAACCTTGTGAGCTGGAC | 15 | CGCTTTAGAAACGGCTCTAGG | 16 |
| A09 | CEBPD | CGCCATGTACGACGACGAG | 17 | CGCCTTGTGATTGCTGTTG | 18 |
| A10 | CFB | GCTCACGCCCGAGACTTTC | 19 | AACCCAAATCCTCATCTTGGAG | 20 |
| A11 | CHI3L1 | ACTCGGGATTAGTACACACTTGTTG | 21 | GTTTGGCTCCTTGGTGATAG | 22 |
| A12 | CITED2 | AATGGGCGAGCACATACAC | 23 | GTGCCCTCCGTTCACAGTC | 24 |
| B01 | CXADR | CATAGGTGAAGACATGGGTGAAC | 25 | GAGACTGGTGGGCCATAAATAAATG | 26 |
| B02 | DNAJC12 | GAAGGCAAAGGAGATTCTGAC | 27 | ACTGCTGGAATGGCATCGAC | 28 |
| B03 | EFNA1 | AGCTGAATGACTACGTGGACATC | 29 | ACTGCCAGCGGACTTGGTC | 30 |
| B04 | FBN2 | CAGATCAGCCTAGAGAGTGTCG | 31 | CCTTTGGTGGATGCGGAAG | 32 |
| B05 | FGA | GAGACTCCACATTTGAAAGCAAG | 33 | CTCTGACAGGGCGAGATTTAG | 34 |
| B06 | FGB | CATGCAGCCAATCCAAACG | 35 | TTCATCCATACTACACCATCATC | 36 |
| B07 | FILIP1L | CTTCAAATGCAGCAGTCTAC | 37 | GATCTCCAGGTTGCACAAAG | 38 |
| B08 | FKBP14 | GAGGTTGCGGTAAGCCGAG | 39 | GCCACCAATCACTAGGAGC | 40 |
| B09 | FLOT2 | GGTGAAGCAGGTCCTCTTG | 41 | CTTCATCCGCTCAGCCTCTG | 42 |
| B10 | FLRT3 | CAGCCTGGAGCATCTTCCTC | 43 | CAGTAAATGAAACCCGCATCG | 44 |
| B11 | FVT1 | ATGAGCATCAATTACCTGGGCAG | 45 | GGCTGTGAACCGAATAATC | 46 |
| B12 | GALNAC4S-6ST | GAGGCTTTGATGACCAAGAGC | 47 | GGCCTGTAGAAATCCCGCAG | 48 |
| C01 | GBP2 | GAACGTATAAAGGCTGAATCTGC | 49 | TGAAGTTTAAGAGCGAGGGTC | 50 |
| C02 | GK | TGCATGACCCCTCCAAGTAGAC | 51 | TAGAGGGAATGGAGCAGGATG | 52 |
| C03 | GLRX | GCAGAGGCTGTGTGGTCATGC | 53 | TGCTTTAATCTTTGCTGGTAGTC | 54 |
| C04 | GSDMC | AGAGATAGGGCTGTGCCTC | 55 | TTATACATAGTGAAACGCTTACGTC | 56 |
| C05 | GSTT1 | GCCAAGGACTTCCCACCTG | 57 | AATGCTTTGTGGACTGCTGAG | 58 |
| C06 | HAMP | CCATGTTCCAGAGGGCGAAG | 59 | GCAGCACATCCCACACTTTG | 60 |
| C07 | HK1 | AACGTGTCCTTCCTCTGTC | 61 | CTGCTTGCCTCTGTGCGTAAC | 62 |
| C08 | HP | TAAGGCATTATGAAGGCAGC | 63 | CCAGTCGCATACCAGGTGTC | 64 |
| C09 | HPR | TAGGGCGTGTGGGTTACGTG | 65 | GTTCGTTCAGTATGGGCTG | 66 |
| C10 | IFITM2 | TCCCACGTACTCTATCTTCCATTC | 67 | CTGATGCAGGACTCGGCTG | 68 |

FIG. 6B

| Well Position | Gene symbol | Primer_F | SEQ ID NO | Primer_R | SEQ ID NO |
|---|---|---|---|---|---|
| C11 | IFNGR1 | AGAATGGATTGATGCCTGC | 69 | TTGTCCAACCCTGGCTTTAAC | 70 |
| C12 | IFNGR2 | GGAGCCTGTTCTTCCTGGTC | 71 | CTCTTCTATCTGTAATGGGATGC | 72 |
| D01 | IL1RAP | CTAGACACCATGAGGCAAATC | 73 | CCTAGTCCAATACCAGATCAGAG | 74 |
| D02 | INSIG2 | TGGCAGAAGGAGAGACAGAG | 75 | CTCGAATCATCAAGTTCACACTC | 76 |
| D03 | KLF9 | GGCCGCCTACATGGACTTC | 77 | AGCTCTTGGCGATGGTGAC | 78 |
| D04 | LBP | TGAGAGTTTGAGGACAAGAAAGATG | 79 | CGGAGCTGAGAGCAGAAATG | 80 |
| D05 | LOXL4 | GTGATGAACGCCCAGCTAGTG | 81 | CAGTCCGGCCCAGATTGTAG | 82 |
| D06 | LRG1 | CTAGAACTCTGTTCCTGCTGC | 83 | CAGGTGGTTGACAGGAGATG | 84 |
| D07 | LY96 | GTTGTTGAAGCTATTTCTGGGAG | 85 | TTGAATTAGGTTGGTGTAGGATG | 86 |
| D08 | MATN3 | TCTCCCGGATAATCGACACTC | 87 | CCTGACATGGTGCCTGTTGAC | 88 |
| D09 | MBL2 | TGAGGTTTCTACTGGGACCAC | 89 | CAGTTCTGCATAAGTTGATTGATAG | 90 |
| D10 | MOCOS | GGCTGCTATATGACCGGAG | 91 | TCGATGAAGGGCTGGATCAG | 92 |
| D11 | NEK6 | GAACCACCCAAATATCATCAAG | 93 | CTGCGTCAGCCAACTCCAG | 94 |
| D12 | NRP1 | CAACAACTATGATACACCTGAGC | 95 | TTCCACTTCACAGCCCAGC | 96 |
| E01 | ORM1 | GCATTTCGCTCACTTGCTG | 97 | AGTTCTTCTCATCGTTCACGTC | 98 |
| E02 | P2RY5 | TTGTATGGGTGCATGTTCAGC | 99 | TGTAAGTTGTAGTTTCATTTCGGAC | 100 |
| E03 | PC | CCTTTCAGCCATCGTCCTTTC | 101 | CCACCTGACCCACCACTTGTAG | 102 |
| E04 | PFKFB3 | GAGCCGCATCGTGTACTAC | 103 | CTGGAGGTTGTGTCTCGTTCTC | 104 |
| E05 | PGK1 | TCTGTTTGATGAAGAGGGAGC | 105 | CAGCCAGCAGGTATGCCAG | 106 |
| E06 | PHF21A | GGCAGAAGGAGATGCACAGC | 107 | TCAGAGTCTACAGGTTTGGAGAG | 108 |
| E07 | PLA2G2A | TGTGTGAGTGTGATAAGGCTGC | 109 | GAGAGGGAAATTCAGCACTGG | 110 |
| E08 | PLOD2 | TAGCCGTATATCTGGTGGTTATG | 111 | GTGTAACTGGTGCAATGAACTC | 112 |
| E09 | PLSCR4 | AACTTGCTTCTGTTGCACTTTAG | 113 | TACATCCCATTCTACATACTGACTG | 114 |
| E10 | PROS1 | ATCGGATACAGGCCCTAAGTC | 115 | TTGTCCAAGACGGCAAGTTG | 116 |
| E11 | PVRL2 | AAGCCAAAGAGACTCAGGTG | 117 | CAGGTATCAGGGCTGGTTCCTC | 118 |
| E12 | RAB43 | GGCCAGGTGATCTTCCTTAGC | 119 | CTAGACCACAAACCGACGCAG | 120 |
| F01 | RCN1 | CATGAGGAGAATGGCCCTG | 121 | CATCTTTGTCTAACTTCCCGTC | 122 |
| F02 | RHOB | TGCCATAAGCGAACTTTGTGC | 123 | GTGTGGTCAGAATGCTACTGTC | 124 |
| F03 | RNASE4 | TGCAGAGGACCCATTCATTG | 125 | CAAGTTGCAGTAGCGATCAC | 126 |
| F04 | SEMA4B | GGAGAAGCCATGTGAGCAAG | 127 | CCGTTGCGTAGCCAGAGTC | 128 |
| F05 | SERPINA3 | CTCTCAGTAAGGAACTTGGAATG | 129 | AGAGCTACACAGGGAATCGCTG | 130 |
| F06 | SERPINB13 | GAAAGAAAGGTGAATCTGCAC | 131 | CAGGAACTTCTGGGCGTACAAC | 132 |
| F07 | SERPINB3 | CGCGGTCTCGTCTATCTG | 133 | GGAAAGGGTGATTACAATGGAAC | 134 |
| F08 | SERPINE1 | AGAGACAGGCCAGCTCGGATTC | 135 | CCAAAGTGCATTACATCCATC | 136 |

FIG. 6C

| Well Position | Gene symbol | Primer_F | SEQ ID NO | Primer_R | SEQ ID NO |
|---|---|---|---|---|---|
| F09 | SLC17A2 | TTGAGTCTGGTTGGAGGAATG | 137 | TCAGAGGCGGGTAAGGGTC | 138 |
| F10 | SNX25 | TCAGTGAGCAAATGTTGGTTTAC | 139 | CTTCTGATTGTGGTCGGTG | 140 |
| F11 | SOD2 | GGAGCACGCTTACTACCTTC | 141 | CATTCTCCCAGTTGATTACATTC | 142 |
| F12 | SPINK1 | CTGAAGAGACGTGGTAAGTGC | 143 | CACTGAGAAGAAAGATGCCTG | 144 |
| G01 | SPP1 | CTGAAACCCACAGCCACAAG | 145 | TGACTATCAATCACATCGGAATG | 146 |
| G02 | STAT3 | TGACATGGAGTTGACCTCG | 147 | CTGGAACCACAAAGTTAGTAGTTTC | 148 |
| G03 | TACC1 | CCTGTGTCGGTGTCCTGTG | 149 | AGGTGAGCACGGCTGTCTTG | 150 |
| G04 | TGM2 | CTTCACAAGGGCGAACCAC | 151 | GCGGCAGACGTACTCCTCAG | 152 |
| G05 | TMEM166 | CTGTACTTTGTTTCTGGCGTGTG | 153 | GTCGCTGCTGCTCTCTCTGTC | 154 |
| G06 | TNFRSF1A | TGTTACACTAATAGAAACTTGGCAC | 155 | CCTTAGGACAGTTCAGCTTGC | 156 |
| G07 | TOX3 | GATTGTCACATCAGTCACCATTG | 157 | TTGCACCGAAGGACTCACTTG | 158 |
| G08 | TPST1 | TGGATGAGGCTGGTGTTACTG | 159 | ATCTCGGACCATCAGGAGAAA | 160 |
| G09 | TUBB2A | AACTTCTCAGATCAATCGTGC | 161 | AGACCATGCTTGAGGACAAC | 162 |
| G10 | TUBB3 | AACAACTGGGCCAAGGGTC | 163 | GTCGGGATACTCCTCACGCAC | 164 |
| G11 | XBP1 | ATATCCTGTTGGGCATTCTG | 165 | GAAAGGGAGGCTGGTAAGGAAC | 166 |
| G12 | ZNF684 | AGGACGGTAGCCGGTATTC | 167 | GCTCCAAGCTGAGGCATGTAGC | 168 |
| H01 | IL6ST | AAGATTTGAAACAGTTGGCATGGAG | 169 | CCTTCACTGAGCAGATATGCTGAA | 170 |
| H02 | SOCS3 | CCACTACTGAACCTCCTCC | 171 | TCTTCCGACAGAGATGCTGAA | 172 |
| H03 | JUNB | CGACTACAAACTCCTGAAACCG | 173 | GAAGAGGCGAGCTTGAGAGAC | 174 |
| H04 | BCL3 | CACTCTCTACCAGATAACTGAGGAG | 175 | TAATAATTTACATCGTGATCCGTGC | 176 |
| H05 | B2M | GCAAGGACTGGTCTTTCTATCTC | 177 | ACTTAACTATCTTGGGCTGTGAC | 178 |
| H06 | HPRT1 | GGCCATCTGCTTAGTAGAGC | 179 | TTAGGAATGCAGCAACTGAC | 180 |
| H07 | RPL13A | TGAGTGAAAGGGAGCCAGAAG | 181 | TGCAGAGTATATGACCAGGTG | 182 |
| H08 | GAPDH | AGAGCACAAGAGGAAGAGAGAG | 183 | GGTTGAGCACAGGGTACTTTATTG | 184 |
| H09 | ACTB | AATGCTTCTAGGCGGACTATG | 185 | CTCCAACCGACTGCTGTCAC | 186 |
| H10 | TFRC | AGCTGAGATTCCTGGTTCG | 187 | CATGCCCTGTATTCATATTGTG | 188 |
| H11 | HSP90AB1 | GCAGAGGAACCCAATGCTG | 189 | GGACACTATACAAGGGCACAAG | 190 |
| H12 | PPIA | AATGGGTTACTTCTGAAACATCAC | 191 | GACTCCTACCCTCAGGTGGTC | 192 |

SEQUENCE LISTING

```
<160> NUMBER OF SEQ ID NOS: 196

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
ggagtgttag gagcagccag                                              20

<210> SEQ ID NO 2
<211> LENGTH: 22
<212> TYPE: DNA
<213> ORGANISM: Artificial
<220> FEATURE:
<223> OTHER INFORMATION: Primer

<400> SEQUENCE: 2
catacgatgt ttgtgatgca ac                                           22

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
tcctgtccaa catccaaggt g                                            21

<210> SEQ ID NO 4
<211> LENGTH: 21
<212> TYPE: DNA
<213> ORGANISM: Artificial
```

<220> FEATURE:
<223> OTHER INFORMATION: Primer

<400> SEQUENCE: 4
ttgctagaag tgaggaggct g                                             21

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
gtgaaaggtg ttgctgtttg                                               20

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
aatgactgtt ctcccataca cg                                            22

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
gtatcctcag agatgctgcg tg                                            22

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
tgacagagaa agcacaccaa atg                                           23

<210> SEQ ID NO 9
<211> LENGTH: 19
<212> TYPE: DNA
<213> ORGANISM: Artificial
<220> FEATURE:
<223> OTHER INFORMATION: Primer

<400> SEQUENCE: 9
cctccttccc aatggcatc                                                19

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
agctgcccag tctcgtgttc                                               20

<210> SEQ ID NO 11
<211> LENGTH: 19
<212> TYPE: DNA
<213> ORGANISM: Artificial
<220> FEATURE:
<223> OTHER INFORMATION: Primer

<400> SEQUENCE: 11
tcaatccatg accagggag                                               19

<210> SEQ ID NO 12
<211> LENGTH: 21
<212> TYPE: DNA
<213> ORGANISM: Artificial
<220> FEATURE:
<223> OTHER INFORMATION: Primer

<400> SEQUENCE: 12
attgtttcag gtgtctgctt g                                            21

<210> SEQ ID NO 13
<211> LENGTH: 21
<212> TYPE: DNA
<213> ORGANISM: Artificial
<220> FEATURE:
<223> OTHER INFORMATION: Primer

<400> SEQUENCE: 13
gagagacagc acaatgggct c                                            21

<210> SEQ ID NO 14
<211> LENGTH: 24
<212> TYPE: DNA
<213> ORGANISM: Artificial
<220> FEATURE:
<223> OTHER INFORMATION: Primer

<400> SEQUENCE: 14
cttccgaaat acttcctcta ggtg                                         24

<210> SEQ ID NO 15
<211> LENGTH: 21
<212> TYPE: DNA
<213> ORGANISM: Artificial
<220> FEATURE:
<223> OTHER INFORMATION: Primer

<400> SEQUENCE: 15
ccagaacctt gtgagctgga c                                            21

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
cgctttagaa acggctctag g                                            21

<210> SEQ ID NO 17
<211> LENGTH: 19
<212> TYPE: DNA
<213> ORGANISM: Artificial
<220> FEATURE:
<223> OTHER INFORMATION: Primer

<400> SEQUENCE: 17
cgccatgtac gacgacgag                                                    19

<210> SEQ ID NO 18
<211> LENGTH: 19
<212> TYPE: DNA
<213> ORGANISM: Artificial
<220> FEATURE:
<223> OTHER INFORMATION: Primer

<400> SEQUENCE: 18
cgccttgtga ttgctgttg                                                    19

<210> SEQ ID NO 19
<211> LENGTH: 19
<212> TYPE: DNA
<213> ORGANISM: Artificial
<220> FEATURE:
<223> OTHER INFORMATION: Primer

<400> SEQUENCE: 19
gctcacgccc gagactttc                                                    19

<210> SEQ ID NO 20
<211> LENGTH: 22
<212> TYPE: DNA
<213> ORGANISM: Artificial
<220> FEATURE:
<223> OTHER INFORMATION: Primer

<400> SEQUENCE: 20
aacccaaatc ctcatcttgg ag                                                22

<210> SEQ ID NO 21
<211> LENGTH: 25
<212> TYPE: DNA
<213> ORGANISM: Artificial
<220> FEATURE:
<223> OTHER INFORMATION: Primer

<400> SEQUENCE: 21
actcgggatt agtacacact tgttg                                             25

<210> SEQ ID NO 22
<211> LENGTH: 20
<212> TYPE: DNA
<213> ORGANISM: Artificial
<220> FEATURE:
<223> OTHER INFORMATION: Primer

<400> SEQUENCE: 22
gtttggctcc ttggtgatag                                                   20

<210> SEQ ID NO 23
<211> LENGTH: 19
<212> TYPE: DNA
<213> ORGANISM: Artificial
<220> FEATURE:
<223> OTHER INFORMATION: Primer

<400> SEQUENCE: 23
aatgggcgag cacatacac                                                    19

<210> SEQ ID NO 24

```
<211> LENGTH: 19
<212> TYPE: DNA
<213> ORGANISM: Artificial
<220> FEATURE:
<223> OTHER INFORMATION: Primer

<400> SEQUENCE: 24
gtgccctccg ttcacagtc                                              19

<210> SEQ ID NO 25
<211> LENGTH: 23
<212> TYPE: DNA
<213> ORGANISM: Artificial
<220> FEATURE:
<223> OTHER INFORMATION: Primer

<400> SEQUENCE: 25
cataggtgaa gacatgggtg aac                                         23

<210> SEQ ID NO 26
<211> LENGTH: 25
<212> TYPE: DNA
<213> ORGANISM: Artificial
<220> FEATURE:
<223> OTHER INFORMATION: Primer

<400> SEQUENCE: 26
gagactggtg ggccataaat aaatg                                       25

<210> SEQ ID NO 27
<211> LENGTH: 21
<212> TYPE: DNA
<213> ORGANISM: Artificial
<220> FEATURE:
<223> OTHER INFORMATION: Primer

<400> SEQUENCE: 27
gaaggcaaag gagattctga c                                           21

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
actgctggaa tggcatcgac                                             20

<210> SEQ ID NO 29
<211> LENGTH: 23
<212> TYPE: DNA
<213> ORGANISM: Artificial
<220> FEATURE:
<223> OTHER INFORMATION: Primer

<400> SEQUENCE: 29
agctgaatga ctacgtggac atc                                         23

<210> SEQ ID NO 30
<211> LENGTH: 19
<212> TYPE: DNA
<213> ORGANISM: Artificial
<220> FEATURE:
<223> OTHER INFORMATION: Primer

<400> SEQUENCE: 30
```

```
actgccagcg gacttggtc                                              19

<210> SEQ ID NO 31
<211> LENGTH: 22
<212> TYPE: DNA
<213> ORGANISM: Artificial
<220> FEATURE:
<223> OTHER INFORMATION: Primer

<400> SEQUENCE: 31
cagatcagcc tagagagtgt cg                                          22

<210> SEQ ID NO 32
<211> LENGTH: 19
<212> TYPE: DNA
<213> ORGANISM: Artificial
<220> FEATURE:
<223> OTHER INFORMATION: Primer

<400> SEQUENCE: 32
cctttggtgg atgcggaag                                              19

<210> SEQ ID NO 33
<211> LENGTH: 23
<212> TYPE: DNA
<213> ORGANISM: Artificial
<220> FEATURE:
<223> OTHER INFORMATION: Primer

<400> SEQUENCE: 33
gagactccac atttgaaagc aag                                         23

<210> SEQ ID NO 34
<211> LENGTH: 21
<212> TYPE: DNA
<213> ORGANISM: Artificial
<220> FEATURE:
<223> OTHER INFORMATION: Primer

<400> SEQUENCE: 34
ctctgacagg gcgagattta g                                           21

<210> SEQ ID NO 35
<211> LENGTH: 19
<212> TYPE: DNA
<213> ORGANISM: Artificial
<220> FEATURE:
<223> OTHER INFORMATION: Primer

<400> SEQUENCE: 35
catgcagcca atccaaacg                                              19

<210> SEQ ID NO 36
<211> LENGTH: 23
<212> TYPE: DNA
<213> ORGANISM: Artificial
<220> FEATURE:
<223> OTHER INFORMATION: Primer

<400> SEQUENCE: 36
ttcatccata ctacaccatc atc                                         23

<210> SEQ ID NO 37
<211> LENGTH: 21
<212> TYPE: DNA
```

```
<213> ORGANISM: Artificial
<220> FEATURE:
<223> OTHER INFORMATION: Primer

<400> SEQUENCE: 37
cttcaaatgc agccagtcta c                                              21

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
gatctccagg ttgcacaaag                                                20

<210> SEQ ID NO 39
<211> LENGTH: 19
<212> TYPE: DNA
<213> ORGANISM: Artificial
<220> FEATURE:
<223> OTHER INFORMATION: Primer

<400> SEQUENCE: 39
gaggttgcgg taagccgag                                                 19

<210> SEQ ID NO 40
<211> LENGTH: 19
<212> TYPE: DNA
<213> ORGANISM: Artificial
<220> FEATURE:
<223> OTHER INFORMATION: Primer

<400> SEQUENCE: 40
gccaccaatc actaggagc                                                 19

<210> SEQ ID NO 41
<211> LENGTH: 19
<212> TYPE: DNA
<213> ORGANISM: Artificial
<220> FEATURE:
<223> OTHER INFORMATION: Primer

<400> SEQUENCE: 41
ggtgaagcag gtcctcttg                                                 19

<210> SEQ ID NO 42
<211> LENGTH: 20
<212> TYPE: DNA
<213> ORGANISM: Artificial
<220> FEATURE:
<223> OTHER INFORMATION: Primer

<400> SEQUENCE: 42
cttcatccgc tcagcctctg                                                20

<210> SEQ ID NO 43
<211> LENGTH: 20
<212> TYPE: DNA
<213> ORGANISM: Artificial
<220> FEATURE:
<223> OTHER INFORMATION: Primer

<400> SEQUENCE: 43
cagcctggag catcttcctc                                                20
```

<210> SEQ ID NO 44
<211> LENGTH: 21
<212> TYPE: DNA
<213> ORGANISM: Artificial
<220> FEATURE:
<223> OTHER INFORMATION: Primer

<400> SEQUENCE: 44
cagtaaatga aacccgcatc g                                             21

<210> SEQ ID NO 45
<211> LENGTH: 23
<212> TYPE: DNA
<213> ORGANISM: Artificial
<220> FEATURE:
<223> OTHER INFORMATION: Primer

<400> SEQUENCE: 45
atgagcatca attacctggg cag                                           23

<210> SEQ ID NO 46
<211> LENGTH: 20
<212> TYPE: DNA
<213> ORGANISM: Artificial
<220> FEATURE:
<223> OTHER INFORMATION: Primer

<400> SEQUENCE: 46
ggctgtgaaa ccgaataatc                                               20

<210> SEQ ID NO 47
<211> LENGTH: 21
<212> TYPE: DNA
<213> ORGANISM: Artificial
<220> FEATURE:
<223> OTHER INFORMATION: Primer

<400> SEQUENCE: 47
gaggctttga tgaccaagag c                                             21

<210> SEQ ID NO 48
<211> LENGTH: 20
<212> TYPE: DNA
<213> ORGANISM: Artificial
<220> FEATURE:
<223> OTHER INFORMATION: Primer

<400> SEQUENCE: 48
ggcctgtaga aatcccgcag                                               20

<210> SEQ ID NO 49
<211> LENGTH: 23
<212> TYPE: DNA
<213> ORGANISM: Artificial
<220> FEATURE:
<223> OTHER INFORMATION: Primer

<400> SEQUENCE: 49
gaacgtataa aggctgaatc tgc                                           23

<210> SEQ ID NO 50
<211> LENGTH: 21
<212> TYPE: DNA
<213> ORGANISM: Artificial
<220> FEATURE:

<223> OTHER INFORMATION: Primer

<400> SEQUENCE: 50
tgaagtttaa gagcgagggt c                                              21

<210> SEQ ID NO 51
<211> LENGTH: 21
<212> TYPE: DNA
<213> ORGANISM: Artificial
<220> FEATURE:
<223> OTHER INFORMATION: Primer

<400> SEQUENCE: 51
tgcatgaccc tccaagtaga c                                              21

<210> SEQ ID NO 52
<211> LENGTH: 21
<212> TYPE: DNA
<213> ORGANISM: Artificial
<220> FEATURE:
<223> OTHER INFORMATION: Primer

<400> SEQUENCE: 52
tagagggaat ggagcaggat g                                              21

<210> SEQ ID NO 53
<211> LENGTH: 19
<212> TYPE: DNA
<213> ORGANISM: Artificial
<220> FEATURE:
<223> OTHER INFORMATION: Primer

<400> SEQUENCE: 53
gcagaggctg tggtcatgc                                                 19

<210> SEQ ID NO 54
<211> LENGTH: 23
<212> TYPE: DNA
<213> ORGANISM: Artificial
<220> FEATURE:
<223> OTHER INFORMATION: Primer

<400> SEQUENCE: 54
tgctttaatc tttgctggta gtc                                            23

<210> SEQ ID NO 55
<211> LENGTH: 19
<212> TYPE: DNA
<213> ORGANISM: Artificial
<220> FEATURE:
<223> OTHER INFORMATION: Primer

<400> SEQUENCE: 55 agagatagg ctgtgcctc                                                  19

<210> SEQ ID NO 56
<211> LENGTH: 25
<212> TYPE: DNA
<213> ORGANISM: Artificial
<220> FEATURE:
<223> OTHER INFORMATION: Primer

<400> SEQUENCE: 56
ttatacatag tgaaacgctt acgtc                                          25

```
<210> SEQ ID NO 57
<211> LENGTH: 19
<212> TYPE: DNA
<213> ORGANISM: Artificial
<220> FEATURE:
<223> OTHER INFORMATION: Primer

<400> SEQUENCE: 57
gccaaggact tcccacctg                                                19

<210> SEQ ID NO 58
<211> LENGTH: 21
<212> TYPE: DNA
<213> ORGANISM: Artificial
<220> FEATURE:
<223> OTHER INFORMATION: Primer

<400> SEQUENCE: 58
aatgctttgt ggactgctga g                                             21

<210> SEQ ID NO 59
<211> LENGTH: 19
<212> TYPE: DNA
<213> ORGANISM: Artificial
<220> FEATURE:
<223> OTHER INFORMATION: Primer

<400> SEQUENCE: 59
ccatgttcca gaggcgaag                                                19

<210> SEQ ID NO 60
<211> LENGTH: 20
<212> TYPE: DNA
<213> ORGANISM: Artificial
<220> FEATURE:
<223> OTHER INFORMATION: Primer

<400> SEQUENCE: 60
gcagcacatc ccacactttg                                               20

<210> SEQ ID NO 61
<211> LENGTH: 20
<212> TYPE: DNA
<213> ORGANISM: Artificial
<220> FEATURE:
<223> OTHER INFORMATION: Primer

<400> SEQUENCE: 61
aacgtgtcct tcctcctgtc                                               20

<210> SEQ ID NO 62
<211> LENGTH: 21
<212> TYPE: DNA
<213> ORGANISM: Artificial
<220> FEATURE:
<223> OTHER INFORMATION: Primer

<400> SEQUENCE: 62
ctgcttgcct ctgtgcgtaa c                                             21

<210> SEQ ID NO 63
<211> LENGTH: 20
<212> TYPE: DNA
<213> ORGANISM: Artificial
<220> FEATURE:
<223> OTHER INFORMATION: Primer
```

```
<400> SEQUENCE: 63
taaggcatta tgaaggcagc                                               20

<210> SEQ ID NO 64
<211> LENGTH: 20
<212> TYPE: DNA
<213> ORGANISM: Artificial
<220> FEATURE:
<223> OTHER INFORMATION: Primer

<400> SEQUENCE: 64
ccagtcgcat accaggtgtc                                               20

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
tagggcgtgt gggttacgtg                                               20

<210> SEQ ID NO 66
<211> LENGTH: 19
<212> TYPE: DNA
<213> ORGANISM: Artificial
<220> FEATURE:
<223> OTHER INFORMATION: Primer

<400> SEQUENCE: 66
gttcgttcag tatgggctg                                                19

<210> SEQ ID NO 67
<211> LENGTH: 24
<212> TYPE: DNA
<213> ORGANISM: Artificial
<220> FEATURE:
<223> OTHER INFORMATION: Primer

<400> SEQUENCE: 67
tcccacgtac tctatcttcc attc                                          24

<210> SEQ ID NO 68
<211> LENGTH: 19
<212> TYPE: DNA
<213> ORGANISM: Artificial
<220> FEATURE:
<223> OTHER INFORMATION: Primer

<400> SEQUENCE: 68
ctgatgcagg actcggctg                                                19

<210> SEQ ID NO 69
<211> LENGTH: 19
<212> TYPE: DNA
<213> ORGANISM: Artificial
<220> FEATURE:
<223> OTHER INFORMATION: Primer

<400> SEQUENCE: 69
agaatggatt gatgcctgc                                                19

<210> SEQ ID NO 70
<211> LENGTH: 21
```

<212> TYPE: DNA
<213> ORGANISM: Artificial
<220> FEATURE:
<223> OTHER INFORMATION: Primer

<400> SEQUENCE: 70
ttgtccaacc ctggctttaa c                                              21

<210> SEQ ID NO 71
<211> LENGTH: 21
<212> TYPE: DNA
<213> ORGANISM: Artificial
<220> FEATURE:
<223> OTHER INFORMATION: Primer

<400> SEQUENCE: 71
ggagcctgtt tcttcctggt c                                              21

<210> SEQ ID NO 72
<211> LENGTH: 23
<212> TYPE: DNA
<213> ORGANISM: Artificial
<220> FEATURE:
<223> OTHER INFORMATION: Primer

<400> SEQUENCE: 72
ctcttctatc tgtaatggga tgc                                            23

<210> SEQ ID NO 73
<211> LENGTH: 21
<212> TYPE: DNA
<213> ORGANISM: Artificial
<220> FEATURE:
<223> OTHER INFORMATION: Primer

<400> SEQUENCE: 73
ctagacacca tgaggcaaat c                                              21

<210> SEQ ID NO 74
<211> LENGTH: 23
<212> TYPE: DNA
<213> ORGANISM: Artificial
<220> FEATURE:
<223> OTHER INFORMATION: Primer

<400> SEQUENCE: 74
cctagtccaa taccagatca gag                                            23

<210> SEQ ID NO 75
<211> LENGTH: 20
<212> TYPE: DNA
<213> ORGANISM: Artificial
<220> FEATURE:
<223> OTHER INFORMATION: Primer

<400> SEQUENCE: 75
tggcagaagg agagacagag                                                20

<210> SEQ ID NO 76
<211> LENGTH: 23
<212> TYPE: DNA
<213> ORGANISM: Artificial
<220> FEATURE:
<223> OTHER INFORMATION: Primer

<400> SEQUENCE: 76
ctcgaatcat caagttcaca ctc                               23

<210> SEQ ID NO 77
<211> LENGTH: 19
<212> TYPE: DNA
<213> ORGANISM: Artificial
<220> FEATURE:
<223> OTHER INFORMATION: Primer

<400> SEQUENCE: 77
ggccgcctac atggacttc                                    19

<210> SEQ ID NO 78
<211> LENGTH: 19
<212> TYPE: DNA
<213> ORGANISM: Artificial
<220> FEATURE:
<223> OTHER INFORMATION: Primer

<400> SEQUENCE: 78
agctcttggc gatggtgac                                    19

<210> SEQ ID NO 79
<211> LENGTH: 25
<212> TYPE: DNA
<213> ORGANISM: Artificial
<220> FEATURE:
<223> OTHER INFORMATION: Primer

<400> SEQUENCE: 79
tgagagtttg aggacaagaa agatg                             25

<210> SEQ ID NO 80
<211> LENGTH: 20
<212> TYPE: DNA
<213> ORGANISM: Artificial
<220> FEATURE:
<223> OTHER INFORMATION: Primer

<400> SEQUENCE: 80
cggagctgag agcagaaatg                                   20

<210> SEQ ID NO 81
<211> LENGTH: 21
<212> TYPE: DNA
<213> ORGANISM: Artificial
<220> FEATURE:
<223> OTHER INFORMATION: Primer

<400> SEQUENCE: 81
gtgatgaacg cccagctagt g                                 21

<210> SEQ ID NO 82
<211> LENGTH: 20
<212> TYPE: DNA
<213> ORGANISM: Artificial
<220> FEATURE:
<223> OTHER INFORMATION: Primer

<400> SEQUENCE: 82
cagtccggcc cagattgtag                                   20

<210> SEQ ID NO 83
<211> LENGTH: 21
<212> TYPE: DNA
<213> ORGANISM: Artificial

```
<220> FEATURE:
<223> OTHER INFORMATION: Primer

<400> SEQUENCE: 83
ctagaactct gttcctgctg c                                              21

<210> SEQ ID NO 84
<211> LENGTH: 20
<212> TYPE: DNA
<213> ORGANISM: Artificial
<220> FEATURE:
<223> OTHER INFORMATION: Primer

<400> SEQUENCE: 84
caggtggttg acaggagatg                                                20

<210> SEQ ID NO 85
<211> LENGTH: 23
<212> TYPE: DNA
<213> ORGANISM: Artificial
<220> FEATURE:
<223> OTHER INFORMATION: Primer

<400> SEQUENCE: 85
gttgttgaag ctatttctgg gag                                            23

<210> SEQ ID NO 86
<211> LENGTH: 23
<212> TYPE: DNA
<213> ORGANISM: Artificial
<220> FEATURE:
<223> OTHER INFORMATION: Primer

<400> SEQUENCE: 86
ttgaattagg ttggtgtagg atg                                            23

<210> SEQ ID NO 87
<211> LENGTH: 21
<212> TYPE: DNA
<213> ORGANISM: Artificial
<220> FEATURE:
<223> OTHER INFORMATION: Primer

<400> SEQUENCE: 87
tctcccggat aatcgacact c                                              21

<210> SEQ ID NO 88
<211> LENGTH: 21
<212> TYPE: DNA
<213> ORGANISM: Artificial
<220> FEATURE:
<223> OTHER INFORMATION: Primer

<400> SEQUENCE: 88
cctgacatgg tgcctgttga c                                              21

<210> SEQ ID NO 89
<211> LENGTH: 21
<212> TYPE: DNA
<213> ORGANISM: Artificial
<220> FEATURE:
<223> OTHER INFORMATION: Primer

<400> SEQUENCE: 89
tgaggtttct actgggacca c                                              21
```

```
<210> SEQ ID NO 90
<211> LENGTH: 25
<212> TYPE: DNA
<213> ORGANISM: Artificial
<220> FEATURE:
<223> OTHER INFORMATION: Primer

<400> SEQUENCE: 90
cagttctgca taagttgatt gatag                                         25

<210> SEQ ID NO 91
<211> LENGTH: 19
<212> TYPE: DNA
<213> ORGANISM: Artificial
<220> FEATURE:
<223> OTHER INFORMATION: Primer

<400> SEQUENCE: 91
ggctgctata tgaccggag                                                19

<210> SEQ ID NO 92
<211> LENGTH: 20
<212> TYPE: DNA
<213> ORGANISM: Artificial
<220> FEATURE:
<223> OTHER INFORMATION: Primer

<400> SEQUENCE: 92
tcgatgaagg gctggatcag                                               20

<210> SEQ ID NO 93
<211> LENGTH: 22
<212> TYPE: DNA
<213> ORGANISM: Artificial
<220> FEATURE:
<223> OTHER INFORMATION: Primer

<400> SEQUENCE: 93
gaaccaccca aatatcatca ag                                            22

<210> SEQ ID NO 94
<211> LENGTH: 19
<212> TYPE: DNA
<213> ORGANISM: Artificial
<220> FEATURE:
<223> OTHER INFORMATION: Primer

<400> SEQUENCE: 94
ctgcgtcagc caactccag                                                19

<210> SEQ ID NO 95
<211> LENGTH: 23
<212> TYPE: DNA
<213> ORGANISM: Artificial
<220> FEATURE:
<223> OTHER INFORMATION: Primer

<400> SEQUENCE: 95
caacaactat gatacacctg agc                                           23

<210> SEQ ID NO 96
<211> LENGTH: 19
<212> TYPE: DNA
<213> ORGANISM: Artificial
<220> FEATURE:
<223> OTHER INFORMATION: Primer
```

```
<400> SEQUENCE: 96
ttccacttca cagcccagc                                           19

<210> SEQ ID NO 97
<211> LENGTH: 19
<212> TYPE: DNA
<213> ORGANISM: Artificial
<220> FEATURE:
<223> OTHER INFORMATION: Primer

<400> SEQUENCE: 97
gcatttcgct cacttgctg                                           19

<210> SEQ ID NO 98
<211> LENGTH: 22
<212> TYPE: DNA
<213> ORGANISM: Artificial
<220> FEATURE:
<223> OTHER INFORMATION: Primer

<400> SEQUENCE: 98
agttcttctc atcgttcacg tc                                       22

<210> SEQ ID NO 99
<211> LENGTH: 21
<212> TYPE: DNA
<213> ORGANISM: Artificial
<220> FEATURE:
<223> OTHER INFORMATION: Primer

<400> SEQUENCE: 99
ttgtatgggt gcatgttcag c                                        21

<210> SEQ ID NO 100
<211> LENGTH: 25
<212> TYPE: DNA
<213> ORGANISM: Artificial
<220> FEATURE:
<223> OTHER INFORMATION: Primer

<400> SEQUENCE: 100
tgtaagttgt agtttcattt cggac                                    25

<210> SEQ ID NO 101
<211> LENGTH: 21
<212> TYPE: DNA
<213> ORGANISM: Artificial
<220> FEATURE:
<223> OTHER INFORMATION: Primer

<400> SEQUENCE: 101
cctttcagcc atcgtccttt c                                        21

<210> SEQ ID NO 102
<211> LENGTH: 22
<212> TYPE: DNA
<213> ORGANISM: Artificial
<220> FEATURE:
<223> OTHER INFORMATION: Primer

<400> SEQUENCE: 102
ccacctgacc caccacttgt ag                                       22

<210> SEQ ID NO 103
```

```
<211> LENGTH: 19
<212> TYPE: DNA
<213> ORGANISM: Artificial
<220> FEATURE:
<223> OTHER INFORMATION: Primer

<400> SEQUENCE: 103
gagccgcatc gtgtactac                                                    19

<210> SEQ ID NO 104
<211> LENGTH: 21
<212> TYPE: DNA
<213> ORGANISM: Artificial
<220> FEATURE:
<223> OTHER INFORMATION: Primer

<400> SEQUENCE: 104
ctggaggttg tgctcgttct c                                                 21

<210> SEQ ID NO 105
<211> LENGTH: 21
<212> TYPE: DNA
<213> ORGANISM: Artificial
<220> FEATURE:
<223> OTHER INFORMATION: Primer

<400> SEQUENCE: 105
tctgtttgat gaagagggag c                                                 21

<210> SEQ ID NO 106
<211> LENGTH: 19
<212> TYPE: DNA
<213> ORGANISM: Artificial
<220> FEATURE:
<223> OTHER INFORMATION: Primer

<400> SEQUENCE: 106
cagccagcag gtatgccag                                                    19

<210> SEQ ID NO 107
<211> LENGTH: 20
<212> TYPE: DNA
<213> ORGANISM: Artificial
<220> FEATURE:
<223> OTHER INFORMATION: Primer

<400> SEQUENCE: 107
ggcagaagga gatgcacagc                                                   20

<210> SEQ ID NO 108
<211> LENGTH: 23
<212> TYPE: DNA
<213> ORGANISM: Artificial
<220> FEATURE:
<223> OTHER INFORMATION: Primer

<400> SEQUENCE: 108
tcagagtcta caggtttgga gag                                               23

<210> SEQ ID NO 109
<211> LENGTH: 22
<212> TYPE: DNA
<213> ORGANISM: Artificial
<220> FEATURE:
<223> OTHER INFORMATION: Primer

<400> SEQUENCE: 109
```

-continued tgtgtgagtg tgataaggct gc                                      22

<210> SEQ ID NO 110
<211> LENGTH: 21
<212> TYPE: DNA
<213> ORGANISM: Artificial
<220> FEATURE:
<223> OTHER INFORMATION: Primer

<400> SEQUENCE: 110
gagagggaaa ttcagcactg g                                       21

<210> SEQ ID NO 111
<211> LENGTH: 23
<212> TYPE: DNA
<213> ORGANISM: Artificial
<220> FEATURE:
<223> OTHER INFORMATION: Primer

<400> SEQUENCE: 111
tagccgtata tctggtggtt atg                                     23

<210> SEQ ID NO 112
<211> LENGTH: 22
<212> TYPE: DNA
<213> ORGANISM: Artificial
<220> FEATURE:
<223> OTHER INFORMATION: Primer

<400> SEQUENCE: 112
gtgtaactgg tgcaatgaac tc                                      22

<210> SEQ ID NO 113
<211> LENGTH: 23
<212> TYPE: DNA
<213> ORGANISM: Artificial
<220> FEATURE:
<223> OTHER INFORMATION: Primer

<400> SEQUENCE: 113
aacttgcttc tgttgcactt tag                                     23

<210> SEQ ID NO 114
<211> LENGTH: 25
<212> TYPE: DNA
<213> ORGANISM: Artificial
<220> FEATURE:
<223> OTHER INFORMATION: Primer

<400> SEQUENCE: 114
tacatcccat tctacatact gactg                                   25

<210> SEQ ID NO 115
<211> LENGTH: 21
<212> TYPE: DNA
<213> ORGANISM: Artificial
<220> FEATURE:
<223> OTHER INFORMATION: Primer

<400> SEQUENCE: 115
atcggataca ggccctaagt c                                       21

<210> SEQ ID NO 116
<211> LENGTH: 20
<212> TYPE: DNA

```
<213> ORGANISM: Artificial
<220> FEATURE:
<223> OTHER INFORMATION: Primer

<400> SEQUENCE: 116
ttgtccaaga cggcaagttg                                              20

<210> SEQ ID NO 117
<211> LENGTH: 20
<212> TYPE: DNA
<213> ORGANISM: Artificial
<220> FEATURE:
<223> OTHER INFORMATION: Primer

<400> SEQUENCE: 117
aagccaaaga gactcaggtg                                              20

<210> SEQ ID NO 118
<211> LENGTH: 22
<212> TYPE: DNA
<213> ORGANISM: Artificial
<220> FEATURE:
<223> OTHER INFORMATION: Primer

<400> SEQUENCE: 118
caggtatcag ggctggttcc tc                                           22

<210> SEQ ID NO 119
<211> LENGTH: 21
<212> TYPE: DNA
<213> ORGANISM: Artificial
<220> FEATURE:
<223> OTHER INFORMATION: Primer

<400> SEQUENCE: 119
ggccaggtga tcttccttag c                                            21

<210> SEQ ID NO 120
<211> LENGTH: 21
<212> TYPE: DNA
<213> ORGANISM: Artificial
<220> FEATURE:
<223> OTHER INFORMATION: Primer

<400> SEQUENCE: 120
ctagaccaca aaccgacgca g                                            21

<210> SEQ ID NO 121
<211> LENGTH: 19
<212> TYPE: DNA
<213> ORGANISM: Artificial
<220> FEATURE:
<223> OTHER INFORMATION: Primer

<400> SEQUENCE: 121
catgaggaga atggccctg                                               19

<210> SEQ ID NO 122
<211> LENGTH: 22
<212> TYPE: DNA
<213> ORGANISM: Artificial
<220> FEATURE:
<223> OTHER INFORMATION: Primer

<400> SEQUENCE: 122
catctttgtc taacttcccg tc                                           22
```

<210> SEQ ID NO 123
<211> LENGTH: 21
<212> TYPE: DNA
<213> ORGANISM: Artificial
<220> FEATURE:
<223> OTHER INFORMATION: Primer

<400> SEQUENCE: 123
tgccataagc gaactttgtg c                                              21

<210> SEQ ID NO 124
<211> LENGTH: 22
<212> TYPE: DNA
<213> ORGANISM: Artificial
<220> FEATURE:
<223> OTHER INFORMATION: Primer

<400> SEQUENCE: 124
gtgtggtcag aatgctactg tc                                             22

<210> SEQ ID NO 125
<211> LENGTH: 20
<212> TYPE: DNA
<213> ORGANISM: Artificial
<220> FEATURE:
<223> OTHER INFORMATION: Primer

<400> SEQUENCE: 125
tgcagaggac ccattcattg                                                20

<210> SEQ ID NO 126
<211> LENGTH: 20
<212> TYPE: DNA
<213> ORGANISM: Artificial
<220> FEATURE:
<223> OTHER INFORMATION: Primer

<400> SEQUENCE: 126
caagttgcag tagcgatcac                                                20

<210> SEQ ID NO 127
<211> LENGTH: 20
<212> TYPE: DNA
<213> ORGANISM: Artificial
<220> FEATURE:
<223> OTHER INFORMATION: Primer

<400> SEQUENCE: 127
ggagaagcca tgtgagcaag                                                20

<210> SEQ ID NO 128
<211> LENGTH: 19
<212> TYPE: DNA
<213> ORGANISM: Artificial
<220> FEATURE:
<223> OTHER INFORMATION: Primer

<400> SEQUENCE: 128
ccgttgcgta gccagagtc                                                 19

<210> SEQ ID NO 129
<211> LENGTH: 23
<212> TYPE: DNA
<213> ORGANISM: Artificial
<220> FEATURE:

```
<223> OTHER INFORMATION: Primer

<400> SEQUENCE: 129
ctctcagtaa ggaacttgga atg                                          23

<210> SEQ ID NO 130
<211> LENGTH: 22
<212> TYPE: DNA
<213> ORGANISM: Artificial
<220> FEATURE:
<223> OTHER INFORMATION: Primer

<400> SEQUENCE: 130
agagctacac agggaatcgc tg                                           22

<210> SEQ ID NO 131
<211> LENGTH: 21
<212> TYPE: DNA
<213> ORGANISM: Artificial
<220> FEATURE:
<223> OTHER INFORMATION: Primer

<400> SEQUENCE: 131
gaaagaaagg tgaatctgca c                                            21

<210> SEQ ID NO 132
<211> LENGTH: 22
<212> TYPE: DNA
<213> ORGANISM: Artificial
<220> FEATURE:
<223> OTHER INFORMATION: Primer

<400> SEQUENCE: 132
caggaacttc tgggcgtaca ac                                           22

<210> SEQ ID NO 133
<211> LENGTH: 19
<212> TYPE: DNA
<213> ORGANISM: Artificial
<220> FEATURE:
<223> OTHER INFORMATION: Primer

<400> SEQUENCE: 133
cgcggtctcg tgctatctg                                               19

<210> SEQ ID NO 134
<211> LENGTH: 23
<212> TYPE: DNA
<213> ORGANISM: Artificial
<220> FEATURE:
<223> OTHER INFORMATION: Primer

<400> SEQUENCE: 134
ggaaagggtg attacaatgg aac                                          23

<210> SEQ ID NO 135
<211> LENGTH: 21
<212> TYPE: DNA
<213> ORGANISM: Artificial
<220> FEATURE:
<223> OTHER INFORMATION: Primer

<400> SEQUENCE: 135
agagacaggc agctcggatt c                                            21
```

<210> SEQ ID NO 136
<211> LENGTH: 21
<212> TYPE: DNA
<213> ORGANISM: Artificial
<220> FEATURE:
<223> OTHER INFORMATION: Primer

<400> SEQUENCE: 136
ccaaagtgca ttacatccat c                                             21

<210> SEQ ID NO 137
<211> LENGTH: 21
<212> TYPE: DNA
<213> ORGANISM: Artificial
<220> FEATURE:
<223> OTHER INFORMATION: Primer

<400> SEQUENCE: 137
ttgagtctgg ttggaggaat g                                             21

<210> SEQ ID NO 138
<211> LENGTH: 19
<212> TYPE: DNA
<213> ORGANISM: Artificial
<220> FEATURE:
<223> OTHER INFORMATION: Primer

<400> SEQUENCE: 138
tcagaggcgg gtaagggtc                                                19

<210> SEQ ID NO 139
<211> LENGTH: 23
<212> TYPE: DNA
<213> ORGANISM: Artificial
<220> FEATURE:
<223> OTHER INFORMATION: Primer

<400> SEQUENCE: 139
tcagtgagca aatgttggtt tac                                           23

<210> SEQ ID NO 140
<211> LENGTH: 19
<212> TYPE: DNA
<213> ORGANISM: Artificial
<220> FEATURE:
<223> OTHER INFORMATION: Primer

<400> SEQUENCE: 140
cttctgattg tggtcggtg                                                19

<210> SEQ ID NO 141
<211> LENGTH: 20
<212> TYPE: DNA
<213> ORGANISM: Artificial
<220> FEATURE:
<223> OTHER INFORMATION: Primer

<400> SEQUENCE: 141
ggagcacgct tactaccttc                                               20

<210> SEQ ID NO 142
<211> LENGTH: 23
<212> TYPE: DNA
<213> ORGANISM: Artificial
<220> FEATURE:
<223> OTHER INFORMATION: Primer

```
<400> SEQUENCE: 142
cattctccca gttgattaca ttc                                              23

<210> SEQ ID NO 143
<211> LENGTH: 21
<212> TYPE: DNA
<213> ORGANISM: Artificial
<220> FEATURE:
<223> OTHER INFORMATION: Primer

<400> SEQUENCE: 143
ctgaagagac gtggtaagtg c                                                21

<210> SEQ ID NO 144
<211> LENGTH: 21
<212> TYPE: DNA
<213> ORGANISM: Artificial
<220> FEATURE:
<223> OTHER INFORMATION: Primer

<400> SEQUENCE: 144
cactgagaag aaagatgcct g                                                21

<210> SEQ ID NO 145
<211> LENGTH: 20
<212> TYPE: DNA
<213> ORGANISM: Artificial
<220> FEATURE:
<223> OTHER INFORMATION: Primer

<400> SEQUENCE: 145
ctgaaaccca cagccacaag                                                  20

<210> SEQ ID NO 146
<211> LENGTH: 23
<212> TYPE: DNA
<213> ORGANISM: Artificial
<220> FEATURE:
<223> OTHER INFORMATION: Primer

<400> SEQUENCE: 146
tgactatcaa tcacatcgga atg                                              23

<210> SEQ ID NO 147
<211> LENGTH: 19
<212> TYPE: DNA
<213> ORGANISM: Artificial
<220> FEATURE:
<223> OTHER INFORMATION: Primer

<400> SEQUENCE: 147
tgacatggag ttgacctcg                                                   19

<210> SEQ ID NO 148
<211> LENGTH: 25
<212> TYPE: DNA
<213> ORGANISM: Artificial
<220> FEATURE:
<223> OTHER INFORMATION: Primer

<400> SEQUENCE: 148
ctggaaccac aaagttagta gtttc                                            25

<210> SEQ ID NO 149
<211> LENGTH: 19
```

```
<212> TYPE: DNA
<213> ORGANISM: Artificial
<220> FEATURE:
<223> OTHER INFORMATION: Primer

<400> SEQUENCE: 149
cctgtgtcgg tgtcctgtg                                                19

<210> SEQ ID NO 150
<211> LENGTH: 20
<212> TYPE: DNA
<213> ORGANISM: Artificial
<220> FEATURE:
<223> OTHER INFORMATION: Primer

<400> SEQUENCE: 150
aggtgagcac ggctgtcttg                                               20

<210> SEQ ID NO 151
<211> LENGTH: 19
<212> TYPE: DNA
<213> ORGANISM: Artificial
<220> FEATURE:
<223> OTHER INFORMATION: Primer

<400> SEQUENCE: 151
cttcacaagg gcgaaccac                                                19

<210> SEQ ID NO 152
<211> LENGTH: 20
<212> TYPE: DNA
<213> ORGANISM: Artificial
<220> FEATURE:
<223> OTHER INFORMATION: Primer

<400> SEQUENCE: 152
gcggcagacg tactcctcag                                               20

<210> SEQ ID NO 153
<211> LENGTH: 23
<212> TYPE: DNA
<213> ORGANISM: Artificial
<220> FEATURE:
<223> OTHER INFORMATION: Primer

<400> SEQUENCE: 153
ctgtactttg tttctggcgt gtg                                           23

<210> SEQ ID NO 154
<211> LENGTH: 21
<212> TYPE: DNA
<213> ORGANISM: Artificial
<220> FEATURE:
<223> OTHER INFORMATION: Primer

<400> SEQUENCE: 154
gtcgctgctg ctctctctgt c                                             21

<210> SEQ ID NO 155
<211> LENGTH: 25
<212> TYPE: DNA
<213> ORGANISM: Artificial
<220> FEATURE:
<223> OTHER INFORMATION: Primer

<400> SEQUENCE: 155
```

```
tgttacacta atagaaactt ggcac                                          25

<210> SEQ ID NO 156
<211> LENGTH: 21
<212> TYPE: DNA
<213> ORGANISM: Artificial
<220> FEATURE:
<223> OTHER INFORMATION: Primer

<400> SEQUENCE: 156
ccttaggaca gttcagcttg c                                              21

<210> SEQ ID NO 157
<211> LENGTH: 23
<212> TYPE: DNA
<213> ORGANISM: Artificial
<220> FEATURE:
<223> OTHER INFORMATION: Primer

<400> SEQUENCE: 157
gattgtcaca tcagtcacca ttg                                            23

<210> SEQ ID NO 158
<211> LENGTH: 21
<212> TYPE: DNA
<213> ORGANISM: Artificial
<220> FEATURE:
<223> OTHER INFORMATION: Primer

<400> SEQUENCE: 158
ttgcaccgaa ggactcactt g                                              21

<210> SEQ ID NO 159
<211> LENGTH: 21
<212> TYPE: DNA
<213> ORGANISM: Artificial
<220> FEATURE:
<223> OTHER INFORMATION: Primer

<400> SEQUENCE: 159
tggatgaggc tggtgttact g                                              21

<210> SEQ ID NO 160
<211> LENGTH: 21
<212> TYPE: DNA
<213> ORGANISM: Artificial
<220> FEATURE:
<223> OTHER INFORMATION: Primer

<400> SEQUENCE: 160
atctcggacc atcaggagaa a                                              21

<210> SEQ ID NO 161
<211> LENGTH: 21
<212> TYPE: DNA
<213> ORGANISM: Artificial
<220> FEATURE:
<223> OTHER INFORMATION: Primer

<400> SEQUENCE: 161
aacttctcag atcaatcgtg c                                              21

<210> SEQ ID NO 162
<211> LENGTH: 20
<212> TYPE: DNA
<213> ORGANISM: Artificial
```

```
<220> FEATURE:
<223> OTHER INFORMATION: Primer

<400> SEQUENCE: 162
agaccatgct tgaggacaac                                              20

<210> SEQ ID NO 163
<211> LENGTH: 19
<212> TYPE: DNA
<213> ORGANISM: Artificial
<220> FEATURE:
<223> OTHER INFORMATION: Primer

<400> SEQUENCE: 163
aacaactggg ccaagggtc                                               19

<210> SEQ ID NO 164
<211> LENGTH: 21
<212> TYPE: DNA
<213> ORGANISM: Artificial
<220> FEATURE:
<223> OTHER INFORMATION: Primer

<400> SEQUENCE: 164
gtcgggatac tcctcacgca c                                            21

<210> SEQ ID NO 165
<211> LENGTH: 20
<212> TYPE: DNA
<213> ORGANISM: Artificial
<220> FEATURE:
<223> OTHER INFORMATION: Primer

<400> SEQUENCE: 165
atatcctgtt gggcattctg                                              20

<210> SEQ ID NO 166
<211> LENGTH: 22
<212> TYPE: DNA
<213> ORGANISM: Artificial
<220> FEATURE:
<223> OTHER INFORMATION: Primer

<400> SEQUENCE: 166
gaaagggagg ctggtaagga ac                                           22

<210> SEQ ID NO 167
<211> LENGTH: 19
<212> TYPE: DNA
<213> ORGANISM: Artificial
<220> FEATURE:
<223> OTHER INFORMATION: Primer

<400> SEQUENCE: 167
aggacggtag ccggtattc                                               19

<210> SEQ ID NO 168
<211> LENGTH: 19
<212> TYPE: DNA
<213> ORGANISM: Artificial
<220> FEATURE:
<223> OTHER INFORMATION: Primer

<400> SEQUENCE: 168
gctccaagcc tgggatcag                                               19
```

<210> SEQ ID NO 169
<211> LENGTH: 25
<212> TYPE: DNA
<213> ORGANISM: Artificial
<220> FEATURE:
<223> OTHER INFORMATION: Primer

<400> SEQUENCE: 169
aagatttgaa acagttggca tggag                                            25

<210> SEQ ID NO 170
<211> LENGTH: 20
<212> TYPE: DNA
<213> ORGANISM: Artificial
<220> FEATURE:
<223> OTHER INFORMATION: Primer

<400> SEQUENCE: 170
ccttcactga ggcatgtagc                                                  20

<210> SEQ ID NO 171
<211> LENGTH: 21
<212> TYPE: DNA
<213> ORGANISM: Artificial
<220> FEATURE:
<223> OTHER INFORMATION: Primer

<400> SEQUENCE: 171
ccacctactg aaccctcctc c                                                21

<210> SEQ ID NO 172
<211> LENGTH: 21
<212> TYPE: DNA
<213> ORGANISM: Artificial
<220> FEATURE:
<223> OTHER INFORMATION: Primer

<400> SEQUENCE: 172
tcttccgaca gagatgctga a                                                21

<210> SEQ ID NO 173
<211> LENGTH: 22
<212> TYPE: DNA
<213> ORGANISM: Artificial
<220> FEATURE:
<223> OTHER INFORMATION: Primer

<400> SEQUENCE: 173
cgactacaaa ctcctgaaac cg                                               22

<210> SEQ ID NO 174
<211> LENGTH: 21
<212> TYPE: DNA
<213> ORGANISM: Artificial
<220> FEATURE:
<223> OTHER INFORMATION: Primer

<400> SEQUENCE: 174
gaagaggcga gcttgagaga c                                                21

<210> SEQ ID NO 175
<211> LENGTH: 25
<212> TYPE: DNA
<213> ORGANISM: Artificial
<220> FEATURE:
<223> OTHER INFORMATION: Primer

```
<400> SEQUENCE: 175
cactctctac cagataactg aggag                                              25

<210> SEQ ID NO 176
<211> LENGTH: 25
<212> TYPE: DNA
<213> ORGANISM: Artificial
<220> FEATURE:
<223> OTHER INFORMATION: Primer

<400> SEQUENCE: 176
taataattta catcgtgatc cgtgc                                              25

<210> SEQ ID NO 177
<211> LENGTH: 23
<212> TYPE: DNA
<213> ORGANISM: Artificial
<220> FEATURE:
<223> OTHER INFORMATION: Primer

<400> SEQUENCE: 177
gcaaggactg gtctttctat ctc                                                23

<210> SEQ ID NO 178
<211> LENGTH: 23
<212> TYPE: DNA
<213> ORGANISM: Artificial
<220> FEATURE:
<223> OTHER INFORMATION: Primer

<400> SEQUENCE: 178
acttaactat cttgggctgt gac                                                23

<210> SEQ ID NO 179
<211> LENGTH: 20
<212> TYPE: DNA
<213> ORGANISM: Artificial
<220> FEATURE:
<223> OTHER INFORMATION: Primer

<400> SEQUENCE: 179
ggccatctgc ttagtagagc                                                    20

<210> SEQ ID NO 180
<211> LENGTH: 20
<212> TYPE: DNA
<213> ORGANISM: Artificial
<220> FEATURE:
<223> OTHER INFORMATION: Primer

<400> SEQUENCE: 180
ttaggaatgc agcaactgac                                                    20

<210> SEQ ID NO 181
<211> LENGTH: 21
<212> TYPE: DNA
<213> ORGANISM: Artificial
<220> FEATURE:
<223> OTHER INFORMATION: Primer

<400> SEQUENCE: 181
tgagtgaaag ggagccagaa g                                                  21

<210> SEQ ID NO 182
```

```
<211> LENGTH: 21
<212> TYPE: DNA
<213> ORGANISM: Artificial
<220> FEATURE:
<223> OTHER INFORMATION: Primer

<400> SEQUENCE: 182
tgcagagtat atgaccaggt g                                              21

<210> SEQ ID NO 183
<211> LENGTH: 22
<212> TYPE: DNA
<213> ORGANISM: Artificial
<220> FEATURE:
<223> OTHER INFORMATION: Primer

<400> SEQUENCE: 183
agagcacaag aggaagagag ag                                             22

<210> SEQ ID NO 184
<211> LENGTH: 24
<212> TYPE: DNA
<213> ORGANISM: Artificial
<220> FEATURE:
<223> OTHER INFORMATION: Primer

<400> SEQUENCE: 184
ggttgagcac agggtacttt attg                                           24

<210> SEQ ID NO 185
<211> LENGTH: 21
<212> TYPE: DNA
<213> ORGANISM: Artificial
<220> FEATURE:
<223> OTHER INFORMATION: Primer

<400> SEQUENCE: 185
aatgcttcta ggcggactat g                                              21

<210> SEQ ID NO 186
<211> LENGTH: 20
<212> TYPE: DNA
<213> ORGANISM: Artificial
<220> FEATURE:
<223> OTHER INFORMATION: Primer

<400> SEQUENCE: 186
ctccaaccga ctgctgtcac                                                20

<210> SEQ ID NO 187
<211> LENGTH: 19
<212> TYPE: DNA
<213> ORGANISM: Artificial
<220> FEATURE:
<223> OTHER INFORMATION: Primer

<400> SEQUENCE: 187
agctgagatt cctggttcg                                                 19

<210> SEQ ID NO 188
<211> LENGTH: 22
<212> TYPE: DNA
<213> ORGANISM: Artificial
<220> FEATURE:
<223> OTHER INFORMATION: Primer

<400> SEQUENCE: 188
```
catgccctgt attcatattg tg 22

<210> SEQ ID NO 189
<211> LENGTH: 19
<212> TYPE: DNA
<213> ORGANISM: Artificial
<220> FEATURE:
<223> OTHER INFORMATION: Primer

<400> SEQUENCE: 189
gcagaggaac ccaatgctg 19

<210> SEQ ID NO 190
<211> LENGTH: 22
<212> TYPE: DNA
<213> ORGANISM: Artificial
<220> FEATURE:
<223> OTHER INFORMATION: Primer

<400> SEQUENCE: 190
ggacactata caagggcaca ag 22

<210> SEQ ID NO 191
<211> LENGTH: 24
<212> TYPE: DNA
<213> ORGANISM: Artificial
<220> FEATURE:
<223> OTHER INFORMATION: Primer

<400> SEQUENCE: 191
aatgggttac ttctgaaaca tcac 24

<210> SEQ ID NO 192
<211> LENGTH: 21
<212> TYPE: DNA
<213> ORGANISM: Artificial
<220> FEATURE:
<223> OTHER INFORMATION: Primer

<400> SEQUENCE: 192
gactcctacc ctcaggtggt c 21

<210> SEQ ID NO 193
<211> LENGTH: 20
<212> TYPE: DNA
<213> ORGANISM: Artificial
<220> FEATURE:
<223> OTHER INFORMATION: Primer

<400> SEQUENCE: 193
gctatgtcgg accttctcag 20

<210> SEQ ID NO 194
<211> LENGTH: 20
<212> TYPE: DNA
<213> ORGANISM: Artificial
<220> FEATURE:
<223> OTHER INFORMATION: Primer

<400> SEQUENCE: 194
cttcgctagg gttgtggatg 20

<210> SEQ ID NO 195
<211> LENGTH: 19
<212> TYPE: DNA

```
<213> ORGANISM: Artificial
<220> FEATURE:
<223> OTHER INFORMATION: Primer

<400> SEQUENCE: 195
gatccgctac catcgctac                                           19

<210> SEQ ID NO 196
<211> LENGTH: 24
<212> TYPE: DNA
<213> ORGANISM: Artificial
<220> FEATURE:
<223> OTHER INFORMATION: Primer

<400> SEQUENCE: 196
atctccacac accatatcat acag                                     24
```

GENE EXPRESSION SIGNATURE FOR IL-6/STAT3 SIGNALING PATHWAY AND USE THEREOF

CROSS-REFERENCE TO RELATED APPLICATIONS

This application is a 35 U.S.C. 371 United States National Phase Application of PCT Application PCT/US2013/039445 filed May 3, 2013 and published as WO 2013/166373 on Nov. 7, 2013, which claims priority to U.S. provisional application Ser. No. 61/642,037 filed on May 3, 2012, each of which is incorporated by reference herein.

This application includes as part of its disclosure a biological sequence listing contained in the file named "43277o1602.txt" and having a size of 33,947 bytes, which was created on Jan. 22, 2015, the contents of which is hereby incorporated by reference in its entirety.

BACKGROUND

1. Field of the Invention

The present invention relates to a novel set of markers, microarrays containing these markers, and an expression signature comprising 16 genes or a subset thereof and the use thereof in determining the regulation status of IL-6/STAT3 signaling pathway in a cell sample or subject, as well as compositions for the detection thereof. The regulation status of IL-6/STAT3 signaling pathway in a cell sample or subject may be assayed based on the level of expression of one or more of these genes. More specifically, the invention provides a set of genes which can be used as biomarkers and as gene signatures for evaluating IL-6/STAT3 pathway regulation or deregulation in a sample; diagnostic and/of classification of a sample, e.g., tumor, as having a deregulated IL-6/STAT3 signaling pathway; determining whether an agent modulates the IL-6/STAT3 signaling pathway in a sample; predicting the response of a subject to an agent that modulates the IL-6/STAT3 signaling pathway; assigning treatment to a subject; and evaluating the pharmacodynamic effects of therapies designed to target the IL-6/STAT3 pathway. The gene expression signature may be used with companion algorithms to provide a quantitative measure of IL-6/STAT3 pathway activity. Expression of the provided biomarkers is preferably determined by RT-PCR using SYBR green, and the expression data analyzed and compared to a control sample by use of the Random Forest method.

2. Description of Related Art

The STAT (Signal Transducer and Activator of Transcription) family consists of seven mammalian members. Originally, STAT proteins were identified as intracellular signaling mediators of cytokine signals. Every STAT family member responds to a defined set of cytokines. Interestingly, STAT3 is known to be activated by IL-6 (Yu H, Pardoll D, Jove R. STATs in cancer inflammation and immunity: a leading role for STAT3. Nat Rev Cancer. 2009 November; 9(11):798-809).

STAT proteins are latent cytoplasmic transcription factors that require phosphorylation for nuclear retention. Engagement of IL-6 to its specific receptor IL-6R (IL-6 receptor) activates receptor-associated tyrosine kinase, such as Janus Kinase 2 (JAK2). Activated JAK2 in turn phosphorylates tyrosine residues in the cytoplasmic tail of the IL-6 receptor that function as docking sites for STAT3. JAK2 dependent phosphorylation of STAT3 leads to its homodimerization and nuclear translocation, where activated STAT3 function as transcriptional activator, inducing expression of target genes (Levy D E, Darnell J E Jr. Stats: transcriptional control and biological impact. Nat Rev Mol Cell Biol. 2002 September; 3(9):651-62).

IL-6/STAT3 has been implicated as crucial mediator for inflammatory response (Grivennikov S I, Karin M. Dangerous liaisons: STAT3 and NF-kappaB collaboration and crosstalk in cancer. Cytokine Growth Factor Rev. 2010 February; 21(1):11-9. Epub 2009 Dec. 16). Moreover, deregulated IL-6/STAT3 signaling has been associated with biological events such as embryonic development, programmed cell death, organogenesis, innate immunity, adaptive immunity and cell growth regulation in many organisms (Mankan A K, Greten F R. Inhibiting signal transducer and activator of transcription 3: rationality and rationale design of inhibitors. Expert Opin Investig Drugs. 2011 September; 20(9):1263-75. Epub 2011 Jul. 14). In addition, STAT3 plays an essential role in cancer initiation and progression by selectively inducing and maintaining a pro-carcinogenic inflammatory microenvironment (Yu H, Pardoll D, Jove R. STATs in cancer inflammation and immunity: a leading role for STAT3. Nat Rev Cancer. 2009 November; 9(11):798-809).

Perturbation of the IL-6/STAT3 signaling pathway causes a change in STAT3 transcriptional activity and, in turn, alters the expression level of STAT3 target genes. Although changes in gene expression of STAT3 target genes can serve as indicators of IL-6/STAT3 pathway activity, real time PCR assay based methods are not yet available to quantitatively measure IL-6/STAT3 pathway activity.

The identification of patient subpopulations most likely to respond to therapy is a central goal of modem molecular medicine. This notion is particularly important for cancer due to the large number of approved and experimental therapies (Rothenberg et al., 2003, Nat. Rev. Cancer 3:303-309), low response rates to many current treatments, and clinical importance of using the optimal therapy in the first treatment cycle (Dracopoli, 2005, Curr. Mol. Med. 5:103-110). In addition, the narrow therapeutic index and severe toxicity profiles associated with currently marketed cytotoxics results in a pressing need for accurate response prediction. Although recent studies have identified gene expression signatures associated with response to cytotoxic chemotherapies (Folgueria et al., 2005, Clin. Cancer Res. 11:7434-7443; Ayers et al., 2004, 22:2284-2293; Chang et al., 2003, Lancet 362:362-369; Rouzier et al., 2005, Proc. Natl. Acad. Sci. USA 102: 8315-8320), these examples (and others from the literature) remain unvalidated and have not yet had a major effect on clinical practice. In addition to technical issues, such as lack of a standard technology platform and difficulties surrounding the collection of clinical samples, the myriad of cellular processes affected by cytotoxic chemotherapies may hinder the identification of practical and robust gene expression predictors of response to these agents. One exception may be the recent finding by microarray that low mRNA expression of the microtubule-associate protein Tau is predictive of improved response to paclitaxel (Rouzier et al., supra).

To improve on the limitations of cytotoxic chemotherapies, current approaches to dnig design in oncology are aimed at modulating specific cell signaling pathways important for tumor growth and survival (Hahn and Weinberg, 2002, Nat. Rev. Cancer 2:331-341; Hanahan and Weinberg, 2000, Cell 100:57-70; Trosko et al., 2004, Ann. N.Y. Acad. Sci. 1028:192-201). In cancer cells, these pathways become deregulated resulting in aberrant signaling, inhibition of apoptosis, increased metastasis, and increased cell proliferation (reviewed in Adjei and Hildalgo, 2005, J. Clin. Oncol. 23:5386-5403). Although normal cells integrate multiple signaling pathways for controlled growth and proliferation, tumors seem to be heavily reliant on activation of one or two pathways ("oncogene activation"). The components of these aberrant signaling pathways represent attractive selective targets for new anticancer therapies. In addition, responder identification for target therapies may be more achievable than for cytotoxics, as it seems logical that patients with tumors that are "driven" by a particular pathway will respond to therapeutics targeting components of that pathway. Therefore, it is crucial that methods to identify the pathways that are active in particular tumors are developed, and this information used to guide therapeutic decisions. Identification of gene expression profiles that are indicative of pathway activation status is one way to achieve this goal.

Given its involvement in numerous biological functions and diseases, a gene expression signature-based readout of IL-6/STAT3 pathway activation may be more appropriate than relying on a single indicator of pathway activity, as the same signature of gene expression may be elicited by activation of multiple components of the pathway.

Based on the foregoing, a reliable method for accurately and quantitatively assessing the IL-6/STAT3 pathway activation status in a biological sample or individual would be beneficial given the apparent role of this pathway in different disease conditions. Particularly, given its involvement in numerous biological functions and diseases, a gene expression signature-based readout of IL-6/STAT3 pathway activation may be more appropriate and predictive than relying on a single indicator of pathway activity, as the same signature of gene expression may be elicited by activation of multiple components of the pathway.

SUMMARY

Signaling pathways play central roles in cellular physiology, and assessing the state of these pathways can help to clarify the molecular mechanisms of disease, non-cancer inflammatory conditions, and the inflammatory response. However, a multitude of components can activate, modify, and/or inhibit IL-6/STAT3 signaling at multiple points along the pathway and/or may be involved in crosstalk with other pathways. As a result, measuring pathway activity using traditional methods that only test a few well-characterized pathway components may miss other important pathway mediators. Conversely, multi-gene expression based methods measure pathway alteration as a function of the downstream effect of pathway regulation on multiple gene expression changes, thus enabling reliable measurement of pathway activity. These downstream gene expression alterations can potentially capture all changes related to any upstream alteration of a pathway component.

The present invention satisfies these unmet needs and describes sets of genes that provide a gene signature for evaluating Notch pathway activity. These gene sets were identified from an initial set of 88 genes derived from microarray profiling on human liver hepatocellular carcinoma cells (HepG2) and human mammary epithelial cells (MCF10A) treated with IL-6 and siRNA targeting STAT3 (FIG. 2A-B). Genes potentially to be included in the Notch gene signature were selected on the basis of statistically significant expression changes in response to IL-6 and reversion of altered expression upon treatment with STAT3 siRNA. These 88 response genes were further verified by SYBR Green based real-time PCR using a 16 sample training set in which nine sample were stimulated with IL-6 to activate pathway activity and seven samples were treated with STAT3 siRNA to reverse the activation of pathway activity by IL-6 (FIG. 3A-B). Using a mathematical classifier method, preferably using Random Forest method, a panel of 16 genes was identified as gene expression signatures for assessing the regulatory status of the IL-6/STAT3 pathway activity. The utility of the 16 gene signature was verified on these samples by cross validation with a Random Forest method and 87.5% of the samples were classified correctly (FIG. 5A-B).

The invention provides compositions for detection of the regulation status of IL-6/STAT3 signaling pathway in a cell sample or subject, comprising primers that amplify at least 5 of the genes selected from the group consisting of STAT3, SOCS3, IFITM2, CEBPD, JUNB, TUBB2A, IL-6ST, CASP4, PROS1, TNFRSF1A, PVRL2, PHF21A, BCL3, NRP1, GLRX, and TGM2 or an ortholog or variant thereof.

In one embodiment, the primers amplify at least 5, at least 6, at least 7, at least 8, at least 9, at least 10, at least 11, at least 12, at least 13, at least 14, or at least 15 of said genes. Preferably, the composition includes primers for amplification of at least 10, at least 11, at least 12, at least 13, at least 14, or at least 15 of said genes. For example, the composition may include primers for amplification of at least 10 of said genes. Most preferably, the composition includes primers for amplification of all 16 of said genes.

In another embodiment, the primers are in contact with the sample to be tested for the level of IL-6/STAT3 pathway activity. In one embodiment, at one of said primers comprises a fluorophore and matched fluorescence quencher. The primers may be contained in one or more wells of a multi-well reaction vessel. Additionally, the primers for amplification of at least two of said genes can be included together in a duplex or multiplex reaction.

TGACATGGAGTTGACCTCG (SEQ ID NO: 147)
and

CTGGAACCACAAAGTTAGTAGTTTC; (SEQ ID NO: 148)

CCACCTACTGAACCCTCCTCC (SEQ ID NO: 171)
and

TCTTCCGACAGAGATGCTGAA; (SEQ ID NO: 172)

TCCCACGTACTCTATCTTCCATTC (SEQ ID NO: 67)
and

CTGATGCAGGACTCGGCTG; (SEQ ID NO: 68)

CGCCATGTACGACGACGAG (SEQ ID NO: 17)
and

CGCCTTGTGATTGCTGTTG; (SEQ ID NO: 18)

CGACTACAAACTCCTGAAACCG (SEQ ID NO: 173)
and

GAAGAGGCGAGCTTGAGAGAC; (SEQ ID NO: 174)

AACTTCTCAGATCAATCGTGC (SEQ ID NO: 161)
and

-continued

AGACCATGCTTGAGGACAAC; (SEQ ID NO: 162)

AAGATTTGAAACAGTTGGCATGGAG (SEQ ID NO: 169)
and

CCTTCACTGAGGCATGTAGC; (SEQ ID NO: 170)

GAGAGACAGCACAATGGGCTC (SEQ ID NO: 13)
and

CTTCCGAAATACTTCCTCTAGGTG; (SEQ ID NO: 14)

ATCGGATACAGGCCCTAAGTC (SEQ ID NO: 115)
and

TTGTCCAAGACGGCAAGTTG; (SEQ ID NO: 116)

TGTTACACTAATAGAAACTTGGCAC (SEQ ID NO: 155)
and

CCTTAGGACAGTTCAGCTTGC; (SEQ ID NO: 156)

AAGCCAAAGAGACTCAGGTG (SEQ ID NO: 117)
and

CAGGTATCAGGGCTGGTTCCTC; (SEQ ID NO: 118)

GGCAGAAGGAGATGCACAGC (SEQ ID NO: 107)
and

TCAGAGTCTACAGGTTTGGAGAG; (SEQ ID NO: 108)

CACTCTCTACCAGATAACTGAGGAG (SEQ ID NO: 175)
and

TAATAATTTACATCGTGATCCGTGC; (SEQ ID NO: 176)

CAACAACTATGATACACCTGAGC (SEQ ID NO: 95)
and

TTCCACTTCACAGCCCAGC; (SEQ ID NO: 96)

GCAGAGGCTGTGGTCATGC (SEQ ID NO: 53)
and

TGCTTTAATCTTTGCTGGTAGTC; (SEQ ID NO: 54)

CTTCACAAGGGCGAACCAC (SEQ ID NO: 151)
and

GCGGCAGACGTACTCCTCAG. (SEQ ID NO: 152)

In another embodiment, the amplified genes are at least 90% identical to or specifically hybridize to at least 5 genes having accession numbers selected from the group consisting of NM_213662, NM_003955, NM_006435, NM_005195, NM_002229, NM_001069, NM_002184, NM_001225, NM_000313, NM_001065, NM_002856, NM_016621, NM_005178, NM_003873, NM_002064, and NM_004613. Preferably, the amplified genes are at least 5 genes having accession numbers selected from the group consisting of NM_213662, NM_003955, NM_006435, NM_005195, NM_002229, NM_001069, NM_002184, NM_001225, NM_000313, NM_001065, NM_002856, NM_016621, NM_005178, NM_003873, NM_002064, and NM_004613.

The compositions of the invention can further comprise primers for detecting the expression level of between 1 and 10 housekeeping genes (e.g., 5 housekeeping genes).

Additionally, the composition can further comprise a DNA or RNA polymerase. In one embodiment, these compositions are adapted for effecting PCR, real-time PCR, strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), reverse transcriptase polymerase chain reaction (RT-PCR), or helicase-dependent isothermal DNA amplification.

In another embodiment, the compositions further comprise a double strand nucleic acid-specific dye that is used for detecting the level of expression. Exemplary double strand nucleic acid specific dyes include, but are not limited to, SYBR Green I, SYBR Gold, ethidium bromide, propidium bromide, Pico Green, Hoechst 33258, YO-PRO-I and YO-YO-I, Boxto, Evagreen, LC Green, LC Green Plus, and Syto 9. Preferably, the composition is effected for real-time PCR amplification with detection by a SYBR Green method.

Moreover, the invention encompasses methods for the detection of IL-6/STAT3 signaling pathway activity or regulation status in a cell sample or subject, comprising use of the inventive compositions. Such methods comprise using these compositions to amplify and detect the level of expression of at least five genes selected from the group consisting of STAT3, SOCS3, IFITM2, CEBPD, JUNB, TUBB2A, IL-6ST, CASP4, PROS1, TNFRSF1A, PVRL2, PHF21A, BCL3, NRP1, GLRX, and TGM2 or an ortholog or variant thereof. Detecting the level of expression can be effected by a method comprising amplification of mRNA of said at least two genes. Preferably, such detection is accomplished using a double strand nucleic acid-specific dye. Non-limiting, exemplary double strand nucleic acid specific dyes include SYBR Green I, SYBR Gold, ethidium bromide, propidium bromide, Pico Green, Hoechst 33258, YO-PRO-I and YO-YO-I, Boxto, Evagreen, LC Green, LC Green Plus, and Syto 9. Amplification can be effected by a method comprising PCR, real-time PCR, strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), reverse transcriptase polymerase chain reaction (RT-PCR), or helicase-dependent isothermal DNA amplification.

Preferably, the methods further comprise comparing the level of expression of said genes in the sample or subject to the level of expression of said genes in a control sample. In one embodiment, the levels of expression are classified using a mathematical classifier method to determine the regulation status of IL-6/STAT3 signaling pathway in the in the sample or subject as compared to the control sample. Preferably, the mathematical classifier is a Random Forest method.

As discussed above, the compositions employed in the methods can include primers that comprise a fluorophore and matched fluorescence quencher. Additionally, such primers may be contained in one or more wells of a multi-well reaction vessel. In one embodiment, the primers for amplification of at least two of said genes are included together in a duplex or multiplex reaction. The methods may further comprise detecting the expression level of between 1 and 10 housekeeping genes.

The invention also encompasses methods for determining the level of activity or regulation status of the IL-6/STAT3 signaling pathway in a cell sample or subject by (1) detecting the expression level of at least 5 of the genes selected from the group consisting of STAT3, SOCS3, IFITM2, CEBPD, JUNB, TUBB2A, IL-6ST, CASP4, PROS1, TNFRSF1A, PVRL2, PHF21A, BCL3, NRP1, GLRX, and TGM2 or an ortholog or variant thereof in a cell sample or subject, e.g., using SYBR Green based real-time PCR. The expression level of the genes in the cell sample or subject can be compared to the expression level of the same genes in a control sample, such that the level of activity or regulation status of the IL-6/STAT3 signaling pathway in a cell sample or in a subject is determined based on this comparison. In one aspect, the ortholog or variant possesses at least 80, 85, 90, or 95% sequence identity to one of the recited genes. In another aspect, the ortholog is a rodent or non-human primate gene.

In particular, methods of determining the level of activity or regulation status of IL-6/STAT3 signaling pathway in a cell sample or in a subject are provided. The methods comprise: (a) detecting the expression of at least 2 genes selected from the group consisting of STAT3, SOCS3, IFITM2, CEBPD, JUNB, TUBB2A, IL-6ST, CASP4, PROS1, TNFRSF1A, PVRL2, PHF21A, BCL3, NRP1, GLRX, and TGM2, or an ortholog or variant thereof, in a cell sample or subject; and (b) comparing the expression level of the genes in the cell sample or subject to the expression level of the same genes in a control cell sample, wherein the level of activity or regulation status of the IL-6/STAT3 signaling pathway in a cell sample or subject is determined based on this comparison. Preferably, at least two primer pairs selected from the group consisting of:

TGACATGGAGTTGACCTCG (SEQ ID NO: 147)
and
CTGGAACCACAAAGTTAGTAGTTTC; (SEQ ID NO: 148)

CCACCTACTGAACCCTCCTCC (SEQ ID NO: 171)
and
TCTTCCGACAGAGATGCTGAA; (SEQ ID NO: 172)

TCCCACGTACTCTATCTTCCATTC (SEQ ID NO: 67)
and
CTGATGCAGGACTCGGCTG; (SEQ ID NO: 68)

CGCCATGTACGACGACGAG (SEQ ID NO: 17)
and
CGCCTTGTGATTGCTGTTG; (SEQ ID NO: 18)

CGACTACAAACTCCTGAAACCG (SEQ ID NO: 173)
and
GAAGAGGCGAGCTTGAGAGAC; (SEQ ID NO: 174)

AACTTCTCAGATCAATCGTGC (SEQ ID NO: 161)
and
AGACCATGCTTGAGGACAAC; (SEQ ID NO: 162)

AAGATTTGAAACAGTTGGCATGGAG (SEQ ID NO: 169)
and
CCTTCACTGAGGCATGTAGC; (SEQ ID NO: 170)

GAGAGACAGCACAATGGGCTC (SEQ ID NO: 13)
and
CTTCCGAAATACTTCCTCTAGGTG; (SEQ ID NO: 14)

ATCGGATACAGGCCCTAAGTC (SEQ ID NO: 115)
and
TTGTCCAAGACGGCAAGTTG; (SEQ ID NO: 116)

TGTTACACTAATAGAAACTTGGCAC (SEQ ID NO: 155)
and
CCTTAGGACAGTTCAGCTTGC; (SEQ ID NO: 156)

AAGCCAAAGAGACTCAGGTG (SEQ ID NO: 117)
and
CAGGTATCAGGGCTGGTTCCTC; (SEQ ID NO: 118)

GGCAGAAGGAGATGCACAGC (SEQ ID NO: 107)
and
TCAGAGTCTACAGGTTTGGAGAG; (SEQ ID NO: 108)

CACTCTCTACCAGATAACTGAGGAG (SEQ ID NO: 175)
and
TAATAATTTACATCGTGATCCGTGC; (SEQ ID NO: 176)

CAACAACTATGATACACCTGAGC (SEQ ID NO: 95)
and
TTCCACTTCACAGCCCAGC; (SEQ ID NO: 96)

GCAGAGGCTGTGGTCATGC (SEQ ID NO: 53)
and
TGCTTTAATCTTTGCTGGTAGTC; (SEQ ID NO: 54)

CTTCACAAGGGCGAACCAC (SEQ ID NO: 151)
and
GCGGCAGACGTACTCCTCAG (SEQ ID NO: 152)

are used to detect the expression of the at least 2 genes.

In one embodiment, gene expression is assayed by real time amplification, which preferably comprises SYBR Green based real-time PCR. The resulting gene expression data is preferably analyzed using a ΔΔCt method and, optionally, further analyzed using a Random Forest method.

In one embodiment, a cell sample is obtained from a patient or non-human animal that is potentially to be treated with a compound or therapy that modulates IL-6/STAT3 signaling and the method is used to predict whether said patient or non-human animal will respond to treatment with said compound or therapy. In another embodiment, a cell sample is obtained from a patient or non-human animal that has been treated with a compound or therapy that modulates IL-6/STAT3 signaling and the method is used to assess the efficacy of the treatment protocol.

These methods may be used to evaluate the regulatory status of IL-6/STAT3 pathway in a sample; classify a cell sample as having a deregulated or regulated IL-6/STAT3 signaling pathway; determine whether an agent modulates the IL-6/STAT3 signaling pathway in sample; predict the response of a subject to an agent that modulates the IL-6/STAT3 signaling pathway (which can be used to assign treatment to a subject); evaluate the pharmacodynamic effects of therapies designed to regulate IL-6/STAT3 pathway signaling; evaluate the pharmacodynamic effects of therapies for treatment of a disease associated with IL-6/STAT3 pathway dysregulation; evaluate toxicity of an agent a compound or therapy that modulates IL-6/STAT3 signaling; detect a disease associated with IL-6/STAT3 pathway dysregulation; identify a disease associated with IL-6/STAT3 pathway dysregulation and/or diagnose a disease associated with IL-6/STAT3 pathway dysregulation or a subject at risk of developing a disease associated with IL-6/STAT3 pathway dysregulation (which can be used to treat said patient for said disease); assign treatment to a subject having a disease associated with IL-6/STAT3 pathway dysregulation; predict treatment outcome for a subject having a disease associated with IL-6/STAT3 pathway dysregulation; monitor treatment efficacy in a subject having a disease associated with IL-6/STAT3 pathway dysregulation; and/or detect inflammation sites in vivo or ex vivo.

In one embodiment, the methods are used to assess a pre-malignant or cancerous inflammatory condition or other disease involving aberrant cell proliferation characterized by IL-6/STAT3 pathway dysregulation (e.g., a precancerous condition, cancer or metastases). Non-limiting examples of cancer include lung, breast, esophageal, head and neck, colonic, gastrointestinal, prostate, multiple myeloma, hepatic, ovarian, neuroblastoma, glioblastoma, melanoma, pancreatic adenocarcinoma, renal cell carcinoma, cholangiocellular carcinoma, and various leukemias and lymphomas. In another embodiment, the methods are used to identify a non-cancer inflammatory condition or disease characterized by IL-6/STAT3 pathway dysregulation. Non-limiting examples of non-cancer inflammatory conditions include hypoferremia of inflammation, acute-phase response to inflammation and infection, chronic inflammation, inflammation in cardiovascular, systemic juvenile rheumatoid arthritis, *Staphylococcus epidermidis*-induced peritoneal inflammation, and pulmonary inflammation (e.g., adult respiratory distress syndrome, shock lung, chronic pulmonary inflammatory disease, pulmonary sarcoidosis, pulmonary fibrosis and silicosis).

Additionally, these methods can be used in a screen for compounds which modulate Notch signaling pathway activity. In one embodiment, such screening methods comprise contacting one or more cells with a compound that potentially modulates Notch pathway activity and detecting the level of activity or regulation status of the Notch signaling pathway in said cells, and, based thereon, identifying said compound as a compound that modulates Notch pathway activity. Preferably, one or more cells are further contacted with an agent known to affect Notch pathway activity.

The invention also encompasses one or more gene expression data sets obtained using the inventive methods. These gene expression data sets can be derived from the same individual or from different individuals. In particular, the expression data sets can be derived from the same or different individual treated with a particular agent or therapeutic regimen. Preferably, the gene expression data sets are annotated to identify one or more variables such as gender, age, disease condition, HLA type, treatment regimen, genetic deficiency. In one embodiment, the gene expression data set is suitable for use as part of a therapeutic assessment and/or design of a treatment regimen and/or the design of a therapeutic planning regimen. Moreover, the invention encompasses methods of using such gene expression set as part of a therapeutic assessment and/or design of a treatment regimen.

DETAILED DESCRIPTION OF THE FIGURES

FIG. 1 is a schematic depicting an overview of the experiments that resulted in identification of a unique gene signature profile of the IL-6/STAT3 pathway.

Figure 2:
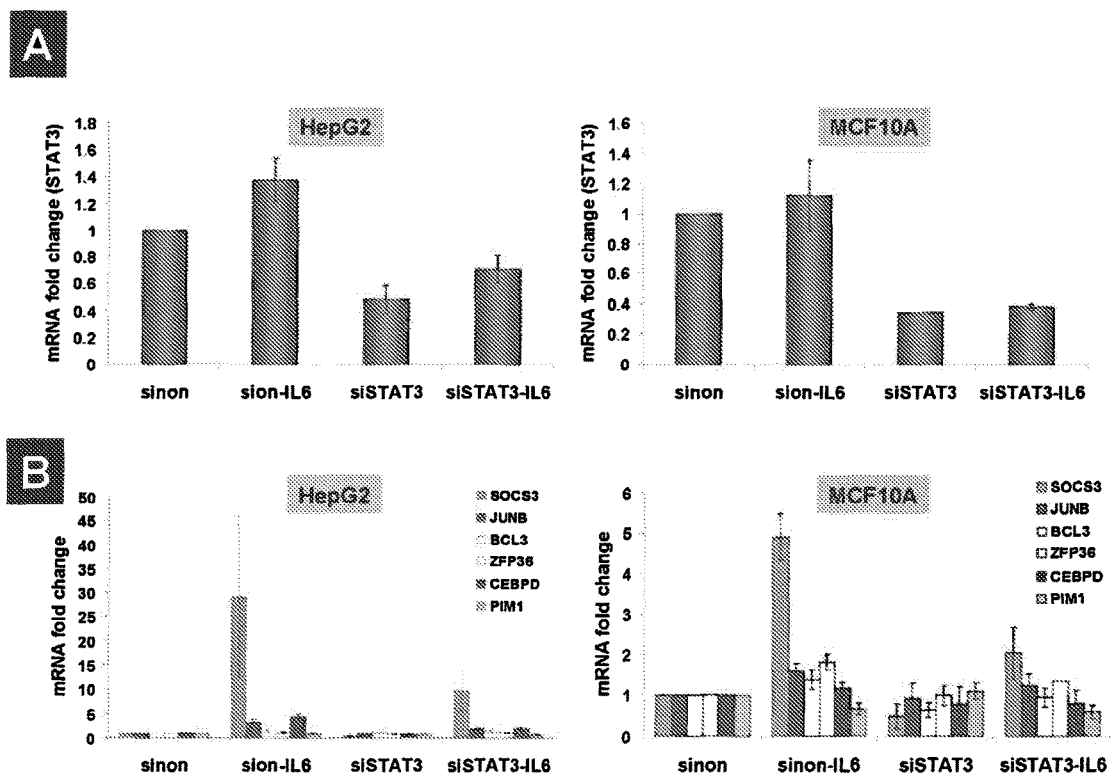

FIG. 2 depicts the result of experiments wherein HepG2 and MCF10A cells were transfected with siRNA targeting STAT3 for 72 hours and IL-6 was added in the last 8 hours. Activation of IL-6/STAT3 pathway was confirmed in both cell lines by increased mRNA expression levels of IL-6/STAT3 targeting genes (Panel B). The effect of STAT3 targeting siRNA was verified by decreased mRNA expression levels of STAT3 in HepG2 and MCF10A cells (Panel A).

Figure 3:
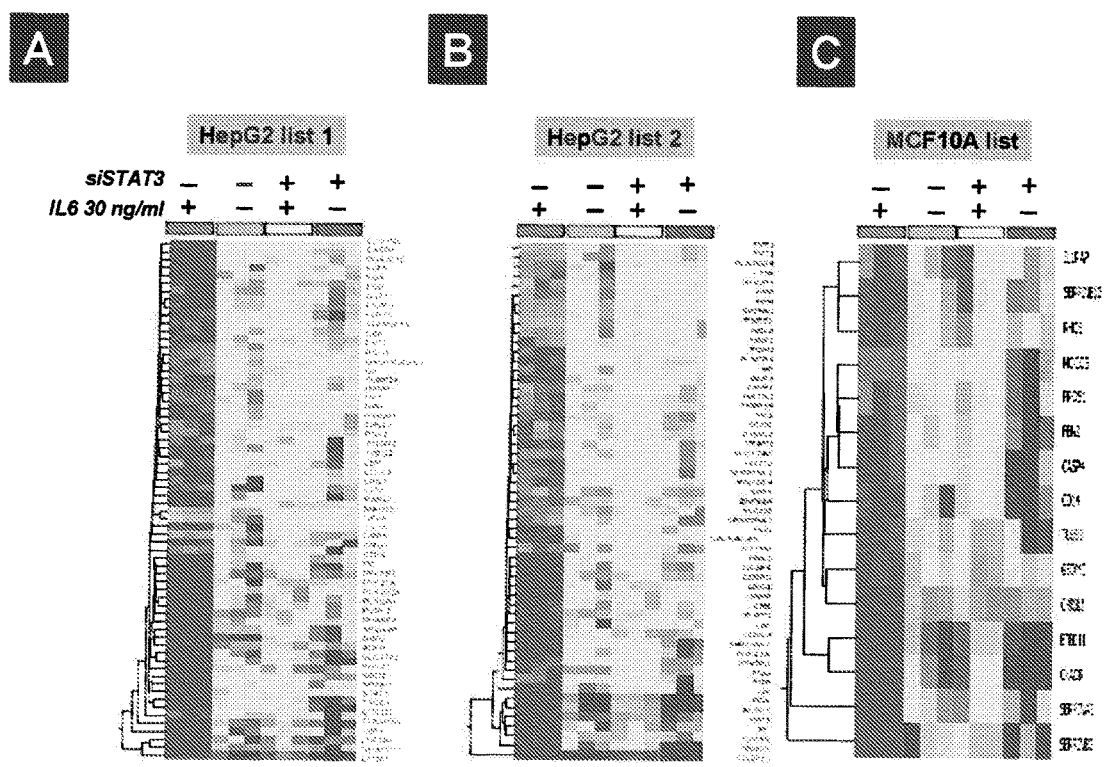

FIG. 3 depicts whole genome microarray analysis used to identify the eighty-eight (88) IL-6/STAT3 response genes. Panels A and B show a list of IL-6/STAT3 response genes identified using HepG2 cells, while Panel C shows a list of IL-6/STAT3 response genes identified using MCF10A cells.

Figure 4:
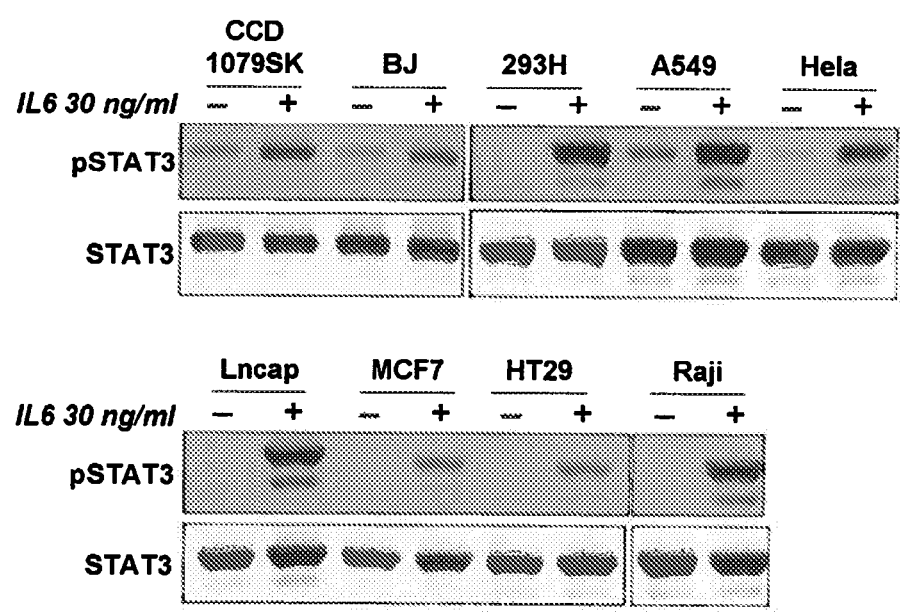
Figure 4:
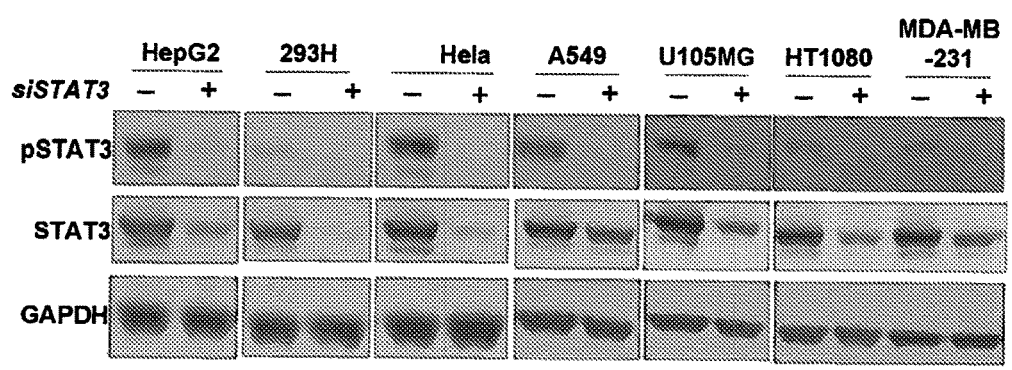

FIG. 4 depicts protein expression levels in sixteen (16) samples, which were used as a training dataset for IL-6/STAT3 pathway gene signature identification. Nine samples were stimulated with IL-6 (Panel A), and western blot analysis confirmed increased STAT3 protein levels. Seven samples were transfected with siRNA targeting STAT3 (Panel B), and western blot analysis confirmed decreased STAT3 protein levels in both phosphorylated and total forms.

Figure 5:
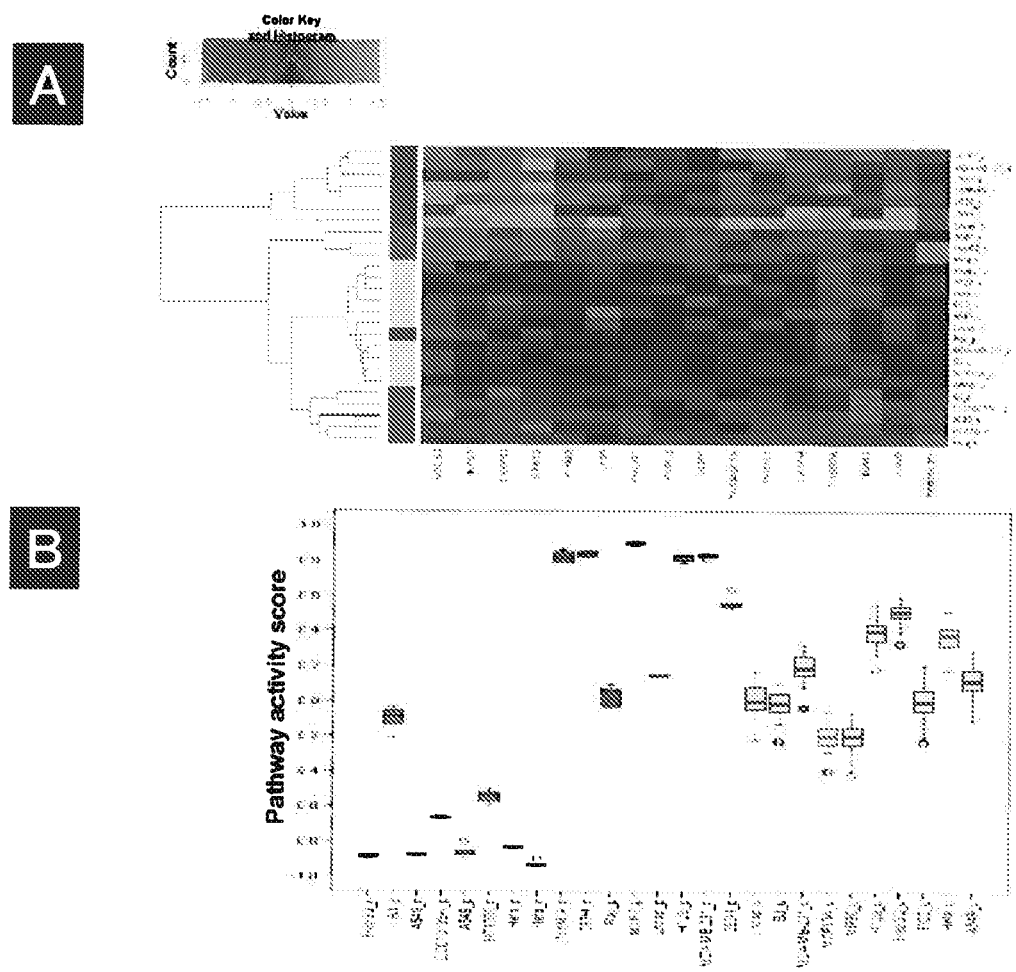

FIG. 5 contains results of cross validation of the gene expression signature of the IL-6/STAT3 pathway. A heatmap depicts the PCR expression data of the 16 signature genes across sixteen samples (Panel A). The gene signature was verified by cross validation on 16 samples with Random Forest Machine classification method (Panel B). The gene signature correctly predicted the regulatory status of fourteen out of sixteen samples in the cross-validation process (Panel B; blue, positively regulated samples; red, negatively regulated samples; gray, untreated samples).

FIG. 6 contains the sequence information for all primers used to validate the 88 TL-6/STAT3 response genes using real-time PCR.

DETAILED DESCRIPTION

Prior to disclosing the invention in detail the following definitions are provided. Unless defined otherwise, all technical and scientific terms used herein have the same meaning as commonly understood to one of ordinary skill in the art to which this invention belongs.

As used herein, oligonucleotide sequences that are complementary to one or more of the genes described herein, refers to oligonucleotides that are capable of hybridizing under stringent conditions to at least part of the nucleotide sequence of said genes. Such hybridizable oligonucleotides will typically exhibit at least about 75% sequence identity at the nucleotide level to said genes, preferably about 80% or 85% sequence identity, or more preferably about 90% or 95% or more sequence identity to said genes.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to" refers to the binding, duplexing or hybridizing of a molecule substantially to or only to a particular nucleotide sequence or sequences under stringent conditions when that sequence is present in a complex mixture (e.g., total cellular) DNA or RNA.

"Biomarker" means any gene, protein, or an EST derived from that gene, the expression or level of which changes between certain conditions. Where the expression of the gene correlates with a certain condition, the gene is a biomarker for that condition.

"Biomarker-derived polynucleotides" means the RNA transcribed from a biomarker gene, any cDNA or cRNA produced therefrom, and any nucleic acid derived therefrom, such as synthetic nucleic acid having a sequence derived from the gene corresponding to the biomarker gene.

"Primer" refers to a polynucleotide or polynucleotide analog having a sequence which base-pairs to a second polynucleotide and can be used to prime synthesis of the complement thereof, e.g., synthesis by a reverse transcriptase, thermostable DNA polymerase, or other DNA or RNA polymerase. Frequently primers are used in pairs, i.e., a forwards and reverse primer which base pair with the opposite ends (and on the complementary strands) of a sequence to be amplified. The length of a primer may vary, and typically includes a region of sufficient length to confer specific base pairing under the applicable reaction conditions. For example, a typical primer for use in an RT-PCR may have a complementary sequence of a length between 19 and 25 bases, though the primer length may be longer or shorter depending upon the cycling temperatures, Tm, CG content, complexity of the nucleic acids in the sample, etc. A primer may also optionally include a non-complementary sequence (most typically at the 5' end), for example, to produce a product containing said non-complementary sequence. A primer may also include one or more modifications, such as the addition of a fluorophore and/or a matched quencher (including the fluorophore and quencher pairs shown in Table 1 herein). Primers typically comprise a DNA sequence but may include other nucleic acids or nucleic acid analogs, e.g., RNA, peptide-nucleic acids (PNAs), chimeric molecules comprising one or more DNA, RNA, and/or PNA bases, etc. A PNA oligonucleotide refers to an oligonucleotide wherein the sugar-backbone is substituted with an amide containing backbone, in particular an aminoethylglycine backbone. The bases are retained and are bound directly or indirectly to aza nitrogen atoms of the amide portion of the backbone (see U.S. Pat. Nos. 5,539, 082; 5,714,331; and 5,719,262, each of which is herein incorporated by reference). Other modifications which may be included in a primer are disclosed in U.S. Pat. No. 6,303,374.

A gene marker is "informative" for a condition, phenotype, genotype or clinical characteristic if the expression of the gene marker is correlated or anti-correlated with the condition, phenotype, genotype or clinical characteristic to a greater degree than would be expected by chance.

As used herein, the term "gene" has its meaning as understood in the art. However, it will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs. For clarity, the term gene generally refers to a portion of a nucleic acid that encodes a protein; the term may optionally encompass regulatory sequences. This definition is not intended to exclude application of the term "gene" to non-protein coding expression units but rather to clarify that, in most cases, the term as used in this document refers to a protein coding nucleic acid. In some cases, the gene includes regulatory sequences involved in transcription, or message production or composition. In other embodiments, the gene comprises transcribed sequences that encode for a protein, polypeptide or peptide. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular embodiments, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like. The sequences which are located 5' of the coding region and which are present on the mRNA are referred to as 5' untranslated sequences ("5'UTR"). The sequences which are located 3' or downstream of the coding region and which are present on the mRNA are referred to as 3' untranslated sequences, or ("3'UTR").

"Signature" refers to the differential expression pattern. It could be expressed as the number of individual unique probes whose expression is detected when a cRNA product is used in microarray analysis. It could also be expressed as the number of individual genes whose expression is detected with real time RT-PCR. A signature may be exemplified by a particular set of biomarkers.

A "similarity value" is a number that represents the degree of similarity between two things being compared. For example, a similarity value may be a number that indicates the overall similarity between a cell sample expression profile using specific phenotype-related biomarkers and a control specific to that template (for instance, the similarity to a "deregulated IL-6/STAT3 signaling pathway" template, where the phenotype is deregulated IL-6/STAT3 signaling pathway status). The similarity value may be expressed as a similarity metric, such as a correlation coefficient, or a classification probability or may simply be expressed as the expression level difference, or the aggregate of the expression level differences, between a cell sample expression profile and a baseline template.

As used herein, the terms "measuring expression levels," "obtaining expression level," and "detecting an expression level" and the like, includes methods that quantify a gene expression level of, for example, a transcript of a gene, or a protein encoded by a gene, as well as methods that determine whether a gene of interest is expressed at all. Thus, an assay which provides a "yes" or "no" result without necessarily providing quantification, of an amount of expression is an assay that "measures expression" as that term is used herein. Alternatively, a measured or obtained expression level may be expressed as any quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. The genes identified as being differentially expressed in tumor cells having IL-6/STAT3 signaling pathway deregulation may be used in a variety of nucleic acid or protein detection assays to detect or quantify the expression level of a gene or multiple genes in a given sample. Exemplary methods for detecting the level of expression of a gene include, but are not limited to, Northern blotting, dot or slot blots, reporter gene matrix (see for example, U.S. Pat. No. 5,569,588) nuclease protection, RT-PCR, microarray profiling, differential display, 2D gel electrophoresis, SELDI-TOF, ICAT, enzyme assay, antibody assay, MNAzyme-based detection methods (see U.S. Ser. No. 61/470,919, US 2011/0143338; US 2007/0231810; WO WO/2008/122084; WO/2007/041774; and Mokany et al., J Am Chem Soc. 2010 Jan. 27; 132(3): 1051-1059, each of which is incorporated by reference in its entirety), and the like. Optionally a gene whose level of expression is to be detected may be amplified, for example by methods that may include one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). In the preferred embodiment gene expression will be detected by RT-PCR, preferably using SYBR green.

A "patient" can mean either a human or non-human animal, preferably a mammal.

As used herein, "subject", as refers to an organism or to a cell sample, tissue sample or organ sample derived therefrom, including, for example, cultured cell lines, biopsy, blood sample, or fluid sample containing a cell. In many instances, the subject or sample derived therefrom, comprises a plurality of cell types. In one embodiment, the sample includes, for example, a mixture of tumor and normal cells. In one embodiment, the sample comprises at least 10%, 15%, 20%, et seq., 90%, or 95% tumor cells. The organism may be an animal, including but not limited to, an animal, such as a cow, a pig, a mouse, a rat, a chicken, a cat, a dog, etc., and is usually a mammal, such as a human.

As used herein, the term "pathway" is intended to mean a set of system components involved in two or more sequential molecular interactions that result in the production of a product or activity. A pathway can produce a variety of products or activities that can include, for example, intermolecular interactions, changes in expression of a nucleic acid or polypeptide, the formation or dissociation of a complex between two or more molecules, accumulation or destruction of a metabolic product, activation or deactivation of an enzyme or binding activity. Thus, the term "pathway" includes a variety of pathway types, such as, for example, a biochemical pathway, a gene expression pathway, and a regulatory pathway. Similarly, a pathway can include a combination of these exemplary pathway types.

"IL-6/STAT3 signaling pathway" refers to the intracellular signaling pathway activated when the cytokine IL-6 binds to the IL-6 receptor (IL-6R), and this complex then associates with gp130, inducing dimerization and the initiation of signaling through signal transducer and activator of transcription-3 (STAT3). The IL-6R is composed of two different subunits: (1) an alpha subunit that produces ligand specificity, and (2) gp130 that is a receptor subunit shared in common with other cytokines in the IL-6 family. Binding of IL-6 to its receptor initiates cellular events including activation of JAK kinases, e.g., JAK2, and activation of ras-mediated signaling. Activated JAK kinases phosphorylate and activate STAT transcription factors, i.e., JAK2 activates STAT3, that then move into the nucleus to activate transcription of genes containing STAT3 response elements, e.g., SOCS3. (See, Akira S, et al. Molecular cloning of APRF, a novel IFN-stimulated gene factor 3 p91-related transcription factor involved in the gp130-mediated signaling pathway. Cell. 1994; 77:63-71; Darnell JE., Jr STATs and gene regulation. Science. 1997; 277:1630-1635; and Starr R, et al., (1997) Nature (London) 387:917-921. The ras-mediated pathway, acting through Shc, Grb-2 and Sos-1 upstream and activating Map kinases downstream, activates transcription factors such as ELK-1 and NF-IL-6 (CIEBP-beta) that can act through their own cognate response elements in the genome. These factors and other transcription factors like AP-1 and SRF (serum response factor) that respond to many different signaling pathways come together to regulate a variety of complex promoters and enhancers that respond to IL-6 and other signaling factors. The IL-6/STAT3 signaling pathway includes, but is not limited to, the genes, and proteins encoded thereby, listed in the Tables in this application.

"IL-6/STAT3 agent" refers to a drug or agent that modulates the canonical IL-6/STAT3 signaling pathway. An IL-6/STAT3 pathway inhibitor inhibits IL-6/STAT3 pathway signaling. Molecular targets of such agents may include JAK2 and STAT3, as well as any of the genes listed herein. Such agents are known in the art and include, but are not limited to: AZD1480 (Hedvat et al., The JAK2 Inhibitor, AZD1480, Potently Blocks Stat3 Signaling and Oncogenesis in Solid Tumors. Cancer Cell. 2009 Dec. 8; 16(6):487-97), WP1066 (Calbiochem, La Jolla, Calif., USA), NSC 74859, Stattic (Santa Cruz Biotechnology, Inc.; Schust et al., Stattic: A Small Molecule Inhibitor of STAT3 Activation and Dimerization. Chemistry & Biology. 2006; 13:1235-1242), and LLL12 (Liu et al., Inhinition of STAT3 signaling blocks the anti-apoptotic activity of IL-6 in human liver cancer cells. J Biol Chem, 285:27429-39, Epub 2010 Jun. 18).

The term "deregulated IL-6/STAT3 pathway" is used herein to mean that the IL-6/STAT3 signaling pathway is either hyperactivated or hypoactivated. A IL-6/STAT3 signaling pathway is hyperactivated in a sample (for example, a tumor sample) if it has at least 10%, 20%, 30%, 40%, 50%, 75%, 100%, 200%, 500%, 1000% greater activity/signaling than the IL-6/STAT3 signaling pathway in a normal (regulated) sample. A IL-6/STAT3 signaling pathway is hypoactivated if it has at least 10%, 20%, 30%, 40%, 50%, 75%, 100% less activity/signaling in a sample (for example, a tumor sample) than the IL-6/STAT3 signaling pathway in a normal (regulated) sample. The normal sample with the regulated IL-6/STAT3 signaling pathway may be from adjacent normal tissue, may be other tumor samples which do not have deregulated IL-6/STAT3 signaling, or may be a pool of samples. Alternatively, comparison of samples' IL-6/STAT3 signaling pathway status may be done with identical samples which have been treated with a drug or agent vs. vehicle. The change in activation status may be due to a mutation of one or more genes in the IL-6/STAT3 signaling pathway (such as point mutations, deletion, or amplification), changes in transcriptional regulation (such as methylation, phosphorylation, or acetylation changes), or changes in protein regulation (such as translation or post-translational control mechanisms).

The term "oncogenic pathway" is used herein to mean a pathway that when hyperactivated or hypoactivated contributes to cancer initiation or progression. In one embodiment, an oncogenic pathway is one that contains an oncogene or a tumor suppressor gene.

The term "treating" in its various grammatical forms in relation to the present invention refers to preventing (i.e. chemoprevention), curing, reversing, attenuating, alleviating, minimizing, suppressing, or halting the deleterious effects of a disease state, disease progression, disease causative agent (e.g. bacteria or viruses), or other abnormal condition. For example, treatment may involve alleviating a symptom (i.e., not necessarily all the symptoms) of a disease of attenuating the progression of a disease.

"Treatment of cancer," as used herein, refers to partially or totally inhibiting, delaying, or preventing the progression of cancer including cancer metastasis; inhibiting, delaying, or preventing the recurrence of cancer including cancer metastasis; or preventing the onset or development of cancer (chemoprevention) in a mammal, for example, a human. In addition, the methods of the present invention may be practiced for the treatment of human patients with cancer. However, it is also likely that the methods would also be effective in the treatment of cancer in other mammals.

"Treatment of non-cancer inflammatory conditions," as used herein, refers to partially or totally inhibiting, delaying, or preventing the progression of the condition; or preventing the onset or development of the condition in a mammal, for example, a human. In addition, the methods of the present invention may be practiced for the treatment of human patients with non-cancer inflammatory conditions. However, it is also likely that the methods would also be effective in the treatment of these conditions in other mammals.

As used herein, the term "therapeutically effective amount" is intended to qualify the amount of the treatment in a therapeutic regiment necessary to treat cancer and/or non-cancer inflammatory conditions. This includes combination therapy involving the use of multiple therapeutic agents, such as a combined amount of a first and second treatment where the combined amount will achieve the desired biological response. The desired biological response is partial or total inhibition, delay, or prevention of the progression of cancer, including cancer metastasis, or partial or total inhibition, delay, or prevention of the progression of a non-cancer inflammatory condition; inhibition, delay, or prevention of the recurrence of cancer including cancer metastasis; or the prevention of the onset of development of cancer (chemoprevention) and/or a non-cancer inflammatory condition in a mammal, for example, a human.

"Displaying or outputting a classification result, prediction result, or efficacy result" means that the results of a gene expression based sample classification or prediction are communicated to a user using any medium, such as for example, orally, writing, visual display, etc., computer readable medium or computer system. It will be clear to one skilled in the art that outputting the result is not limited to outputting to a user or a linked external component(s), such as a computer system or computer memory, but may alternatively or additionally be outputting to internal components, such as any computer readable medium. Computer readable media may include, but are not limited to hard drives, floppy disks, CD-ROMs, DVDs, DATs. Computer readable media does not include carrier waves or other wave forms for data transmission. It will be clear to one skilled in the art that the various sample classification methods disclosed and claimed herein, can, but need not be, computer-implemented, and that, for example, the displaying or outputting step can be done by, for example, by communicating to a person orally or in writing (e.g., in handwriting).

As noted above the present invention identifies a novel set of genes, i.e., a gene signature, the levels of expression of which in a cell sample may be used to assess the regulation status of IL-6/STAT3 signaling pathway in a cell sample or subject. This is significant because, prior to Applicants discovery, there were no real time PCR assay based methods available to quantitatively measure IL-6/STAT3 pathway activity. The gene signature in combination with a companion algorithm fulfills this need, and provides biomarkers for assessing the IL-6/STAT3 pathway activity for various applications, e.g., diagnostic/sample classification, e.g., tumors; predicting treatment response and assigning treatment; determining whether an agent modulates the IL-6/STAT3 signaling pathway; and measuring the pharmacodynamic effect of an agent targeting IL-6/STAT3.

Additionally, due to limitations of cytotoxic based chemotherapies, current oncology drug development is designed to target specific cellular signaling pathways critical for tumor growth and progression. Such targeted drug development requires specific biomarkers to monitor the activity status of pathway. Compared to more traditional methods, which rely on detecting the expression of one or a few indicators within the pathway constituents, multi-gene expression based methods measure pathway alteration as a function of the downstream effect of pathway regulation on multiple gene expression changes. These downstream gene expression alterations can potentially capture all changes related to any upstream alteration of a pathway component.

"Disease associated with IL-6/STAT3 dysregulation" refers to a disease or condition in which IL-6/STAT3 pathway activity is altered, e.g., IL-6/STAT3 activity is elevated or decreased relative to a baseline level or a non-diseased control sample, and/or a disease or condition in which manipulation of IL-6/STAT3 activity may be effective for treatment. The IL-6/STAT3 pathway has been shown to play a role in the inflammatory response, non-cancer inflammatory conditions, and cancer initiation and progression. Persistent activation of STAT3 can mediate tumor-promoting inflammation. STAT3 has a dual role in tumor inflammation and immunity by promoting pro-oncogenic inflammatory pathways, including nuclear factor-κB (NF-κB) and IL-6-GP130-JAK pathways, and by opposing STAT1- and NF-κB-mediated T helper 1 anti-tumour immune responses. Consequently, STAT3 is a promising target to redirect inflammation for cancer therapy. (Yu et al. STATs in cancer inflammation and immunity: a leading role for STAT3. Nature Reviews, 9:798-809 (2009)). Deregulation of IL6/STAT3 signaling has been associated with, e.g., embryonic development, programmed cell death, organogenesis, innate immunity, and adaptive immunity. Activation of the IL-6/STAT3 pathway results in a variety of downstream biological effects, which is reflected by changes in gene expression.

Many cancers and non-cancer inflammatory conditions have been associated with aberrant IL-6/STAT3 signaling. Table 1 includes a non-limiting list of exemplary cancers and non-cancer inflammatory conditions that have been associated with the IL-6/STAT-3 pathway.

TABLE 1

Exemplary cancers and non-cancer inflammatory conditions associated with IL-6/STAT-3.

IL6/STAT3 in cancers

| cancer type | evidence | Reference |
|---|---|---|
| multiple myelomas | Aberrant production of IL6 by neoplastic cells has been implicated as a strong contributory factor to the growth of multiple myeloma and other B-cell dyscrasias, T-cell lymphoma, renal and ovarian cell carcinomas, and Kaposi sarcoma | Kawano, M., et al. Autocrine generation and requirement of BSF-2/IL-6 for human multiple myelomas. Nature 332: 83-85, 1988 |
|  | Stat3, is constitutively activated in bone marrow mononuclear cells from patients with multiple myeloma and in the IL-6-dependent human myeloma cell line U266 | Immunity. 1999 January; 10(1): 105-15. |
| Cholangio-cellular carcinoma | Overexpression of IL6 reduced MIR370 expression and reinstated MAP3K8 expression in malignant cholangiocytes in vitro and in tumor cell xenografts in vivo. | Meng, F., Wehbe-Janek, H., Henson, R., Smith, H., Patel, T. Epigenetic regulation of microRNA-370 by interleukin-6 in malignant human cholangiocytes. Oncogene 27: 378-386, 2008. |
| T-cell lymphomas | STAT3 may transform cells by inducing epigenetic silencing of SHP1 in cooperation with DNMT1 and HDAC1 in T-cell lymphomas | Welte, T., Zhang, S. S. M., Wang, T., Zhang, Z., Hesslein, D. G. T., Yin, Z., Kano, A., Iwamoto, Y., Li, E., Craft, J. E., Bothwell, A. L. M., Fikrig, E., Koni, P. A., Flavell, R. A., Fu, X.-Y. STAT3 deletion during hematopoiesis causes Crohn's disease-like pathogenesis and lethality: a critical role of STAT3 in innate immunity. Proc. Nat. Acad. Sci. 100: 1879-1884, 2003. |
| malignant glioma | expression of C/EBP-beta and STAT3 correlated with mesenchymal differentiation and predicted poor clinical outcome | Carro, M. S., Lim, W. K., Alvarez, M. J., Bollo, R. J., Zhao, X., Snyder, E. Y., Sulman, E. P., Anne, S. L., Doetsch, F., Colman, H., Lasorella, A., Aldape, K., Califano, A., Iavarone, A. The transcriptional network for mesenchymal transformation of brain tumours. Nature 463: 318-325, 2010. |
| head and neck cancer | TGF-alpha/EGFR-mediated autocrine growth of transformed epithelial cells is dependent on activation of Stat3 but not Stat1. | J Clin Invest. 1998 Oct. 1; 102(7): 1385-92. |
| leukemia | Constitutive STAT activation is present in many malignancies and has been especially well characterized in acute and chronic leukemias | Coffer P. J., Koenderman L., de Groot R. P. The role of STATs in myeloid differentiation and leukemia. Oncogene, 19: 2511-2522, 2000 |
|  |  | Lin T. S., Mahajan S., Frank D. A. STAT signaling in the pathogenesis and treatment of leukemias. Oncogene, 19: 2496-2504, 2000 |
| breast cancer | Src and JAK family tyrosine kinases cooperate to mediate constitutive Stat3 activation in the absence | Garcia R., Bowman T. L., Niu G., Yu H., Minton S., Muro-Cacho C. A., Cox C. E., Falcone R., Fairclough R., Parsons S., Laudano A., Gazit A., Levitzki A., Kraker A., Jove R. Constitutive activation of Stat3 |

TABLE 1-continued

Exemplary cancers and non-cancer inflammatory conditions associated with IL-6/STAT-3.

| | of EGF stimulation in model human breast cancer cell lines | by the Src and JAK tyrosine kinases participates in growth regulation of human breast carcinoma cells. Oncogene, 20: 2499-2513, 2001. |
|---|---|---|
| renal cell carcinoma | activated STAT3 | Clin Cancer Res. 2002 April; 8(4): 945-54. |
| melanoma | activated STAT3 | Clin Cancer Res. 2002 April; 8(4): 945-54. |
| ovarian carcinoma | activated STAT3 | Clin Cancer Res. 2002 April; 8(4): 945-54. |
| lung cancer | activated STAT3 | Clin Cancer Res. 2002 April; 8(4): 945-54. |
| prostate cancer | activated STAT3 | Clin Cancer Res. 2002 April; 8(4): 945-54. |
| pancretic adenocarcinoma | activated STAT3 | Clin Cancer Res. 2002 April; 8(4): 945-54. |

| non-cancer inflammatory condition | | |
|---|---|---|
| type | Evidence | Reference |
| hypoferremia of inflammation | IL6 is the necessary and sufficient cytokine for the induction of hepcidin during inflammation | Nemeth, E., Rivera, S., Gabayan, V., Keller, C., Taudorf, S., Pedersen, B. K., Ganz, T. IL-6 mediates hypoferremia of inflammation by inducing the synthesis of the iron regulatory hormone hepcidin. J. Clin. Invest. 113: 1271-1276, 2004. |
| acute-phase response to inflammation and infection | IL6 regulates the zinc importer ZIP14 and contributes to the hypozincemia accompanying the acute-phase response to inflammation and infection | Liuzzi, J. P., Lichten, L. A., Rivera, S., Blanchard, R. K., Aydemir, T. B., Knutson, M. D., Ganz, T., Cousins, R. J. Interleukin-6 regulates the zinc transporter Zip14 in liver and contributes to the hypozincemia of the acute-phase response. Proc. Nat. Acad. Sci. 102: 6843-6848, 2005. |
| | production of both proinflammatory and antiinflammatory cytokines was increased and prolonged, probably as a result of STAT3 deletion in macrophages. | Alonzi, T., D. Maritano, B. Gorgoni, G. Rizzuto, C. Libert, V. Poli. 2001. Essential role of STAT3 in the control of the acute-phase response as revealed by inducible gene inactivation in the liver. Mol. Cell. Biol. 21: 1621 |
| chronic inflammation | constitutive activation of Stat3 has also been observed in chronic inflammation | Hanada, T., T. Yoshida, I. Kinjyo, S. Minoguchi, H. Yasukawa, S. Kato, H. Mimata, Y. Nomura, Y. Seki, M. Kubo, A. Yoshimura. 2001. A mutant form of JAB/SOCS1 augments the cytokine-induced JAK/STAT pathway by accelerating degradation of wild-type JAB/CIS family proteins through the SOCS-box. J. Biol. Chem. 276: 40746 |
| inflammation in cardiovascular | reduced inflammation, as measured by IL6 level, is an important mechanism linking the Mediterranean diet to reduced cardiovascular risk | Dai, J., Miller, A. H., Bremner, J. D., Goldberg, J., Jones, L., Shallenberger, L., Buckham, R., Murrah, N. V., Veledar, E., Wilson, P. W., Vaccarino, V. Adherence to the Mediterranean diet is inversely associated with circulating interleukin-6 among middle-aged men. Circulation 117: 169-175, 2008. |
| | STAT3 is crucial in cardiomyocyte resistance to inflammation and other acute injury and in the pathogenesis of age-related heart failure. | Jacoby, J. J., Kalinowski, A., Liu, M.-G., Zhang, S. S.-M., Gao, Q., Chai, G.-X., Ji, L., Iwamoto, Y., Li, E., Schneider, M., Russell, K. S., Fu, X.-Y. Cardiomyocyte-restricted knockout of STAT3 results in higher sensitivity to inflammation, cardiac fibrosis, and heart failure with advanced age. Proc. Nat. Acad. Sci. 100: 12929-12934, 2003. |
| systemic juvenile rheumatoid arthritis | serum IL6 concentration rises significantly in conjunction with the fever spike associated with systemic juvenile rheumatoid arthritis | Rooney, M., David, J., Symons, J., Di Giovine, F., Varsani, H., Woo, P. Inflammatory cytokine responses in juvenile chronic arthritis. Brit. J. Rheumatol. 34: 454-460, 1995. |
| *Staphylococcus epidermidis*-induced peritoneal inflammation | Il6-mediated T-cell recruitment required gp130-dependent Stat3 activation | McLoughlin, R. M., Jenkins, B. J., Grail, D., Williams, A. S., Fielding, C. A., Parker, C. R., Ernst, M., Topley, N., Jones, S. A. IL-6 trans-signaling via STAT3 directs T cell infiltration in acute inflammation. Proc. Nat. Acad. Sci. 102: 9589-9594, 2005. |

TABLE 1-continued

Exemplary cancers and non-cancer inflammatory conditions associated with IL-6/STAT-3.

| pulmonary inflammation | IL-6 induction of lung inflammation occurs via Stat3 | Am J Physiol Lung Cell Mol Physiol. 2012 April; 302(7): L627-39. Epub 2012 Jan. 20. |

By utilizing IL-6 stimulation and siRNA mediated STAT3 knockdown in HepG2 and MCF10A cells followed by gene expression profiling analysis, the inventors have identified a list of 88 response genes whose expression was upregulated in response to IL-6 and whose increased expression levels were diminished by treatment with STAT3 siRNA. These 88 IL-6/STAT3 response genes were further evaluated by real-time PCR with 16 samples from a panel of 13 different cell lines either stimulated with IL-6 and/or inhibited with STAT3 siRNA. Sixteen (16) genes were identified as a specific panel of indicators for IL-6/STAT3 pathway regulation using a random forest classifier method. The 16 gene signature predicted the regulatory status of IL-6/STAT3 pathway in a training set of 16 samples with an accuracy of 87.5% during cross validation process with a Random Forest method. Therefore, the inventors have verified that they have identified a novel gene expression signature comprising a specific set of 16 genes, the expression of which may be assayed (preferably by RT-PCR) to monitor the regulatory status of IL-6/STAT3 pathway activity, and related applications involving the modulation of this important signaling pathway.

In particular, the inventors discovered that the 16 genes listed below provide a gene expression signature to assess the regulatory status of the IL-6/STAT3 pathway, e.g., differentially classify positive regulation of the IL-6/STAT3 pathway from negative regulation of the IL-6/STAT3 pathway.

STAT3
SOCS3
IFITM2
CEBPD
JUNB
TUBB2A
IL6ST
CASP4
PROS1
TNERSF1A
PVRL2
PHF21A
BCL3
NRP1
GLRX
TGM2

Based on these results, the invention provides methods and materials for assaying the IL-6/STAT3 pathway activity level, e.g., in real time, by assaying the expression levels of these 16 genes or a subset thereof alone or in combination with other genes that are involved in this pathway. Preferably the gene subset assayed will comprise at least 5 of these genes, more preferably at least 10 of the genes, most preferably all of these 16 genes. Exemplary primers for amplification of the 16 IL-6/STAT3 signature genes are described in the application (see Experimental Section and FIG. 6). Of course alternative primers may be used and indeed may be required, if e.g., the assay measures expression of orthologs of the listed genes, e.g., rodent orthologs such as in animal assays designed to assess drug efficacy or side effects.

As disclosed in detail in the Experimental Section, this gene expression signature has been developed from cell lines in response to specific pathway manipulation with microarray analysis. Few previous studies have verified their signature genes in terms of different cell lines and real-time PCR platform. Therefore, by developing and verifying a unique gene expression signature correlated to the activation of the IL-6/STAT3 pathway with an companion algorithm, the inventors provide a novel and improved workflow for quantitative pathway gene expression signature for the identification and verification of cells and samples wherein this pathway is affected using a real-time PCR platform.

The inventive gene expression signature, because of the manner by which it was determined, should accurately reflect the regulatory status of IL-6/STAT3 pathway activity and be useful in different assays such as screening for compounds that modulate IL-6/STAT3 signaling and for identifying cells wherein IL-6/STAT3 signaling is abnormal as in malignancy.

As discussed above, and in detail in the Experimental Section, the present inventors identified this signature gene set from an initial list of 88 IL-6/STAT3 response genes identified with microarray analysis in HepG2 and MCF10A cells treated with IL-6 and STAT3-targeting siRNA. The IL-6/STAT3 response genes were validated with real-time PCR in a training set of 16 samples, and 16 IL-6/STAT3 signature genes were identified by a random forest method.

The accuracy and predictive value of this 16 gene signature was later verified by cross validation in those 16 samples using real-time PCR, in which 9 samples were stimulated with IL-6 ("positively regulated") and the 7 samples were transfected with STAT3 siRNA ("negatively regulated"). As shown infra and in the Figures referenced in the Experimental Section, this 16 gene signature had an accuracy of 87.5% in predicting the regulatory status of IL-6/STAT3 pathway activity in these 16 samples. Therefore, the 16 gene signature and the genes in this signature may be used as biomarkers for monitoring the regulatory status of IL-6/STAT3 pathway activity.

In a preferred embodiment, the expression of these 16 genes may be determined in samples by microarray and/or RT-PCR. In an especially preferred embodiment, the expression of these 16 genes may be determined by use of SYBR Green based real-time PCR, the gene expression data analyzed by ΔΔCt method, and the pathway activity determined with the random forest method.

In these methods the regulatory status of a cell sample may be determined by comparing the expression profile of one or more of these 16 genes, preferably at least 5 of these genes, to control samples (e.g., cells having a normal IL-6/STAT3 pathway activity). The assayed cell sample for which regulatory status may be evaluated according to the invention may comprise any cell or cell sample wherein IL-6/STAT3 pathway activity is desirably assayed. This includes by way of example potentially malignant cells, cells which have been obtained from a patient subjected to a chemotherapy regimen which potentially affects IL-6/STAT3 pathway activity, cells wherein IL-6/STAT3 pathway deregulation status is desirably evaluated in a sample; cell samples which are to be classified as having a deregulated or regulated IL-6/STAT3 signaling pathway; a cell sample wherein it is to be determined whether an agent modulates the IL-6/STAT3 signaling pathway in sample; and the like. In addition, the present signature and biomarkers comprised therein can be used to predict the response of a subject to an agent that modulates the IL-6/STAT3 signaling pathway; assigning treatment to a subject; and evaluating the pharmacodynamic effects of therapies designed to regulate IL-6/STAT3 pathway signaling.

Because the present invention relies upon a comparison of the levels of expression by different genes in cell samples, practice of the invention typically requires control and treatment samples to determine the relative regulatory status of a target cell sample vs control. The target cell sample, e.g., may be one manipulated by different means that may affect IL-6/STAT3 pathway regulation status such as contacting with siRNA(s), drug treatment and the like and the control will be the appropriate control for that manipulation. For example the control cells will be treated identically (culture conditions, time, excipients, vehicles) except for the absence of the particular tested manipulation agent such as exposure to a chemotherapeutic agent. Alternatively, the control sample may be computer generated random ΔΔCT variation for each gene.

In the present invention, target polynucleotide molecules are typically extracted from a sample taken from an individual afflicted with cancer or tumor cell lines, and corresponding normal/control tissues or cell lines, respectively. Samples may also be taken from primary cell lines or ex vivo cultures of cells taken from an animal or patient. The sample may be collected in any clinically acceptable manner, but must be collected such that biomarker-derived polynucleotides (i.e., RNA) are preserved. mRNA or nucleic acids derived therefrom (i.e., cDNA or amplified DNA) are preferably labeled distinguishably from standard or control polynucleotide molecules, and both are simultaneously or independently hybridized to a microarray comprising some or all of the biomarkers or biomarker sets or subsets described above. Alternatively, mRNA or nucleic acids derived therefrom may be labeled with the same label as the standard or control polynucleotide molecules, wherein the intensity of hybridization of each at a particular probe is compared. A sample may comprise any clinically relevant tissue sample, such as a tumor biopsy, fine needle aspirate, or hair follicle, or a sample of bodily fluid, such as blood, plasma, serum, lymph, ascitic fluid, cystic fluid, urine. The sample may be taken from a human, or, in a veterinary context, from non-human animals such as ruminants, horses, swine or sheep, or from domestic companion animals such as felines and canines. Additionally, the samples may be from frozen or archived formalin-fixed, paraffin-embedded (H-PE) tissue samples.

Methods for preparing total and poly(A)+RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., CURRENT PROTOCOLS IN MOLECULAR BIOLOGY, vol. 2, Current Protocols Publishing, New York (1994)).

RNA may be isolated from eukaryotic cells by procedures that involve lysis of the cells and denaturation of the proteins contained therein. Cells of interest include wild-type cells (i.e., non-cancerous), drug-exposed wild-type cells, tumor- or tumor-derived cells, modified cells, normal or tumor cell line cells, and drug-exposed modified cells.

Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979)). Poly(A)+RNA is selected by selection with oligo-dT cellulose (see Sambrook et al, MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex. (see Ausubel et al., CURRENT PROTOCOLS IN MOLECULAR BIOLOGY, vol. 2, Current Protocols Publishing, New York (1994). Once bound, poly(A)+mRNA is eluted from the affinity column using 2 mM EDTA/0.1% SDS.

The sample of RNA can comprise a plurality of different mRNA molecules, each different mRNA molecule having a different nucleotide sequence. In a specific embodiment, the mRNA molecules in the RNA sample comprise at least 100 different nucleotide sequences. More preferably, the mRNA molecules of the RNA sample comprise mRNA molecules corresponding to each of the biomarker genes. In another specific embodiment, the RNA sample is a mammalian RNA sample.

In a specific embodiment, total RNA or mRNA from cells is used in the methods of the invention. The source of the RNA can be cells of a plant or animal, human, mammal, primate, non-human animal, dog, cat, mouse, rat, bird, yeast, eukaryote, prokaryote, etc. In specific embodiments, the method of the invention is used with a sample containing total mRNA or total RNA from $1 \times 10^6$ cells or less. In another embodiment, proteins can be isolated from the foregoing sources, by methods known in the art, for use in expression analysis at the protein level.

Probes to the homologs of the biomarker sequences disclosed herein can be employed preferably wherein non-human nucleic acid is being assayed.

In a preferred embodiment of the invention, the IL-6/STAT3 pathway regulation status will be determined based on the expression levels of all of the 16 genes in the IL-6/STAT3 pathway signature versus the control sample. However, it is envisioned that IL-6/STAT3 pathway regulation status may also be determined by assaying the expression of a subset of these 16 genes or biomarkers, i.e., any combination of at least 2 of these genes, at least 3 of these genes, at least 4 of these genes, at least 6 of these genes, at least 7 of these genes, . . . or all of these 16 genes. In addition, it is within the scope of the invention to further assay the expression of additional genes which affect and/or correlate to IL-6/STAT3 pathway regulation status.

Therefore, one aspect of the invention provides a set of 16 biomarkers or a subset thereof whose expression is correlated with IL-6/STAT3 signaling pathway deregulation. These biomarkers identified as useful for classifying subjects according to regulation status of the IL-6/STAT3 signaling pathway may also be used for classification of cell samples, including but not limited to tumors, by assessing pathway activation status; predicting response to treatment, i.e., prospectively identifying patients harboring tumors that have high levels of a particular pathway activity before treating the patients with inhibitors targeting the pathway; assigning treatment; and as early efficacy biomarkers, i.e., an early readout of efficacy. A gene expression signature for pathway activity may also be used to screen for agents that modulate the IL-6/STAT3 signaling pathway. Furthermore, gene expression signatures for pathway activation may also be used as pharmacodynamic biomarkers, i.e., monitoring pathway inhibition in patient tumors or peripheral tissues post-treatment.

Another aspect of the invention provides a method of using these biomarkers or a microarray containing to distinguish tumor types in diagnosis or to predict response to therapeutic agents.

Yet other aspects of the invention provide methods of using these biomarkers or a microarray containing as pharmacodynamic biomarkers, i.e. monitoring pathway inhibition in patient tumors or peripheral tissues post-treatment; as response prediction biomarkers, i.e., prospectively identifying patients harboring tumors that have high levels of a particular pathway activity before treating the patients with inhibitors targeting the pathway; and as early efficacy biomarkers, i.e., an early readout of efficacy.

In another embodiment, the invention provides a set of 16 biomarkers or a subset thereof, or a microarray containing them, that can be used to predict response of a subject to a IL-6/STAT3 signaling pathway agent. In a more specific embodiment, the invention provides a subset of the disclosed set of 16 biomarkers that can be used to predict the response of a subject to an agent that modulates the IL-6/STAT3 signaling pathway. In another embodiment, the invention provides a set of 16 biomarkers that can be used to select a IL-6/STAT3 pathway agent for treatment of a subject with cancer and/or a non-cancer inflammatory condition, e.g., hypoferremia of inflammation, acute-phase response to inflammation and infection, chronic inflammation, inflammation in cardiovascular, systemic juvenile rheumatoid arthritis, *Staphylococcus epidermidis*-induced peritoneal inflammation, and pulmonary inflammation. In yet another embodiment, the pulmonary inflammation condition includes adult respiratory distress syndrome, shock lung, chronic pulmonary inflammatory disease, pulmonary sarcoidosis, pulmonary fibrosis and silicosis. In a more specific embodiment, the invention provides a set of 16 biomarkers that can be used to select a IL-6/STAT3 pathway agent for treatment of a subject with cancer, e.g., lung, breast, esophageal, head and neck, colonic, gastrointestinal, prostate, multiple myeloma, hepatic, ovarian, neuroblastoma, glioblastoma, melanoma, pancreatic adenocarcinoma, renal cell carcinoma, cholangiocellular carcinoma, and various leukemias and lymphomas. Non-limiting examples thereof include low grade/follicular non-Hodgkin's lymphoma (NHL), small lymphocytic (SL) NHL, intermediate grade/follicular NHL, intermediate grade diffuse NHL, chronic lymphocytic leukemia (CLL), high grade immunoblastic NHL, high grade lymphoblastic NHL, high grade small noncleaved cell NHL, bulky disease NHL, mantle cell lymphoma, AIDS-related lymphoma, Waldenstrom's Macroglobulinemia and T cell lymphomas and leukemias. Alternatively, these biomarkers can be used to predict response of a subject to a IL-6/STAT3 signaling pathway agent or to select a IL-6/STAT3 signaling pathway agent for treatment of a subject with a non-cancer inflammatory condition, e.g., hypoferremia of inflammation, acute-phase response to inflammation and infection, chronic inflammation, inflammation in cardiovascular, systemic juvenile rheumatoid arthritis, *Staphylococcus epidermidis*-induced peritoneal inflammation, and pulmonary inflammation. In one embodiment, the pulmonary inflammation condition includes adult respiratory distress syndrome, shock lung, chronic pulmonary inflammatory disease, pulmonary sarcoidosis, pulmonary fibrosis and silicosis. Additionally, the biomarkers can be used to detect inflammation sites in vivo or ex vivo.

In another embodiment, the invention provides a set of 16 genetic biomarkers or a subset thereof, or a microarray containing them, that can be used to determine whether an agent has a pharmacodynamic effect on the IL-6/STAT3 signaling pathway in a subject. The biomarkers provided may be used to monitor inhibition of the IL-6/STAT3 signaling pathway at various time points following treatment of a subject with said agent. In a more specific embodiment, the invention provides a subset of the disclosed 16 biomarkers that can be used to monitor pharmacodynamic activity of an agent on the IL-6/STAT3 signaling pathway.

The subject biomarkers may be used alone or in combination with biomarkers outside the set. For example, biomarkers that distinguish IL-6/STAT3 pathway regulation status may be used in combination with biomarkers that distinguish growth factor signaling pathway regulation status. Any of the biomarker sets provided herein also may also be used in combination with other biomarkers for cancer, inflammation, or for any other clinical or physiological condition.

As noted in a preferred embodiment, the expression value of all 16 genes is assayed by realtime PCR to determine the IL-6/STAT3 pathway regulatory status. To ensure accuracy the expression value of these 16 genes plus control genes (i.e., 1 or more house keeping genes, e.g., 5 house keeping genes) is measured on both the control cell sample and the treatment sample and the ΔΔCt is calculated. This ΔΔCt value of those 16 genes is then compared to ΔΔCt value of 16 genes in a training data pool that contains 16 samples (7 negatively regulated and 9 positively regulated in terms of pathway activity). In the exemplified embodiments, the random forest method is used to determine the regulatory status of the particular target cell sample.

The present invention further provides kits and kit components for effecting the subject gene expression assay methods. In a preferred exemplary embodiment, the kit will comprise an IL-6/STAT3 signaling PCR array product comprising one or more sequences corresponding to these 16 genes, preferably all 16 of these genes or the majority thereof. The invention further may preferably include a web based system for analysis of the gene expression data.

The present invention further provides compositions for the detection of the gene signature comprising 16 genes, or a subset thereof, and the use thereof in determining the regulation status of the IL-6/STAT3 signaling pathway in a cell sample or subject. The composition may further comprise primers for the amplification of between 1 and 10 housekeeping genes, e.g., 5 housekeeping genes. In one embodiment, the compositions comprise primers that are in contact with the sample to be tested for IL-6/STAT3 pathway activity. Such primers may have comprises a fluorophore to provide for a qualitative and/or quantitative readout of the amplification reaction. In one embodiment, at least one primer comprises a fluorophore and matched fluorescence quencher.

For example, the composition comprises primers that amplify at least 2 genes selected from the group consisting of STAT3, SOCS3, IFITM2, CEBPD, JUNB, TUBB2A, IL-6ST, CASP4, PROS1, TNFRSF1A, PVRL2, PHF21A, BCL3, NRP1, GLRX, and TGM2, or an ortholog or variant thereof, which allow for detection of IL-6/STAT3 pathway activation in a cell sample or subject. The enumerated genes in the 16 gene signature correspond to the following accession numbers: NM_213662, NM_003955, NM_006435, NM_005195, NM_002229, NM_001069, NM_002184, NM_001225, NM_000313, NM_001065, NM_002856, NM_016621, NM_005178, NM_003873, NM_002064, and NM_004613. The composition may comprise at least five of the following primer pairs:

```
                                    (SEQ ID NO: 147)
TGACATGGAGTTGACCTCG
and (SEQ ID NO: 148)
CTGGAACCACAAAGTTAGTAGTTTC;

(SEQ ID NO: 171)
CCACCTACTGAACCCTCCTCC
and (SEQ ID NO: 172)
TCTTCCGACAGAGATGCTGAA;

(SEQ ID NO: 67)
TCCCACGTACTCTATCTTCCATTC
and (SEQ ID NO: 68)
CTGATGCAGGACTCGGCTG;

(SEQ ID NO: 17)
CGCCATGTACGACGACGAG
and (SEQ ID NO: 18)
CGCCTTGTGATTGCTGTTG;

(SEQ ID NO: 173)
CGACTACAAACTCCTGAAACCG
and (SEQ ID NO: 174)
GAAGAGGCGAGCTTGAGAGAC;

(SEQ ID NO: 161)
AACTTCTCAGATCAATCGTGC
and (SEQ ID NO: 162)
AGACCATGCTTGAGGACAAC;

(SEQ ID NO: 169)
AAGATTTGAAACAGTTGGCATGGAG
and (SEQ ID NO: 170)
CCTTCACTGAGGCATGTAGC;

(SEQ ID NO: 13)
GAGAGACAGCACAATGGGCTC
and (SEQ ID NO: 14)
CTTCCGAAATACTTCCTCTAGGTG;

(SEQ ID NO: 115)
ATCGGATACAGGCCCTAAGTC and (SEQ ID NO: 116)
TTGTCCAAGACGGCAAGTTG;

(SEQ ID NO: 155)
TGTTACACTAATAGAAACTTGGCAC
and (SEQ ID NO: 156)
CCTTAGGACAGTTCAGCTTGC;

(SEQ ID NO: 117)
AAGCCAAAGAGACTCAGGTG
and (SEQ ID NO: 118)
CAGGTATCAGGGCTGGTTCCTC;

(SEQ ID NO: 107)
GGCAGAAGGAGATGCACAGC
and (SEQ ID NO: 108)
TCAGAGTCTACAGGTTTGGAGAG;

(SEQ ID NO: 175)
CACTCTCTACCAGATAACTGAGGAG
and (SEQ ID NO: 176)
TAATAATTTACATCGTGATCCGTGC;

(SEQ ID NO: 95)
CAACAACTATGATACACCTGAGC
and (SEQ ID NO: 96)
TTCCACTTCACAGCCCAGC;

(SEQ ID NO: 53)
GCAGAGGCTGTGGTCATGC
and (SEQ ID NO: 54)
TGCTTTAATCTTTGCTGGTAGTC;

(SEQ ID NO: 151)
CTTCACAAGGGCGAACCAC
and (SEQ ID NO: 152)
GCGGCAGACGTACTCCTCAG.
```

In one embodiment, the composition includes primers for amplification of at least 5, at least 6, at least 7, at least 8, at least 9, at least 10, at least 11, at least 12, at least 13, at least 14, at least 15, or at least 16 of said genes. Preferably, the composition includes primers for amplification of at least 10 to 15 of said genes. More preferably, the composition includes primers for amplification of all 16 said genes.

In addition to primer pairs for the amplification of Notch signature profiel genes, the composition may further comprise a DNA or RNA polymerase. In one embodiment, the compositions of the invention are adapted for effecting PCR, real-time PCR, strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), reverse transcriptase polymerase chain reaction (RT-PCR), or helicase-dependent isothermal DNA amplification.

Real time PCR, also abbreviated as Q-PCR, qPCR, QRT-PCR, or RT-qPCR, is a laboratory technique based on the PCR (polymerase chain reaction), to amplify and simultaneously quantify targeted DNA molecules, which are most often produced by reverse transcription in order to detect and quantify the template mRNA. It enables both detection and quantification (as absolute copy numbers or relative amount of reference genes) of one or more specific sequences in a DNA sample. The procedure follows the general principle of polymerase chain reaction. The amplified DNA is detected as the reaction progresses in real time. Two common methods for detection of products in real-time PCR are: (1) sequence-specific DNA probes consisting of oligonucleotides that are labeled with a fluorescent reporter which permits detection only after hybridization of the probe with its complementary DNA target, and (2) non-specific fluorescent dyes that intercalate with any double-stranded DNA. The commonly used reagent for method (1) is TaqMan probes and for method (2) is the SYBR Green I dye. Frequently, real-time PCR is combined with reverse transcription to quantify RNA (including messenger RNA and Non-coding RNA).

TaqMan probes are hydrolysis probes that are designed to increase the specificity of real-time PCR assays (Holland, P M; Abramson, RD; Watson, R; Gelfand, DH (1991). "Detection of specific polymerase chain reaction product by utilizing the 5'-3' exonuclease activity of *Thermus aquaticus* DNA polymerase". Proceedings of the National Academy of Sciences of the United States of America 88 (16): 7276-80. PMID 1871133; Gelfand, et al., U.S. Pat. No. 5,210,015; Mayrand; Paul E.: U.S. Pat. No. 7,413,708). TaqMan utilizes a dual-labeled probe (containing a fluorophore and matched fluorescence quencher) and fluorophore-based detection. During hybridization to the complementary target sequence, the 5'-3' nuclease activity of Taq DNA polymerase releases the fluorophore from proximity to the quencher, generating fluorescence intensity proportionate to the amount of complementary target sequence in the reaction. As in other real-time PCR methods, the resulting fluorescence signal permits quantitative measurements of the accumulation of the product during the exponential stages of the PCR; however, the TaqMan probe significantly increases the specificity of the detection.

TaqMan probes consist of a fluorophore covalently attached to the 5'-end of the oligonucleotide probe and a quencher at the 3'-end. Several different fluorophores (e.g. 6-carboxyfluorescein, acronym: FAM, or tetrachlorofluorescin, acronym: TET) and quenchers (e.g. tetramethylrhodamine, acronym: TAMRA, or dihydrocyclopyrroloindole tripeptide minor groove binder, acronym: MGB) are available. The quencher molecule quenches the fluorescence emitted by the fluorophore when excited by the cycler's light source via FRET (Fluorescence Resonance Energy Transfer). As long as the fluorophore and the quencher are in proximity, quenching inhibits any fluorescence signals.

TaqMan probes are designed such that they anneal within a DNA region amplified by a specific set of primers. As the Taq DNA polymerase extends the primer and synthesizes the nascent strand, the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

Another commonly used reagent for detection of products in real-time PCR is SYBR Green I (SG), an asymmetrical cyanine dye that is also used as a nucleic acid stain in molecular biology. SYBR Green I binds to double-stranded DNA. The resulting DNA-dye-complex absorbs blue light (λmax=488 nm) and emits green light (λmax=522 nm). SYBR Green I can be readily used for real-time PCR detection because there is a linear relation between the double-stranded DNA synthesized and the amount of green light emitted.

Reagents for detection of products in real-time PCR also include double strand nucleic acid specific dyes such as SYBR Gold, ethidium bromide, propidium bromide, Pico Green, reagents for detection of real-time PCR products include the fluorescent dyes and quenchers listed in Table 1 below. Hoechst 33258, YO-PRO-I and YO-YO-I, Boxto, Evagreen, LC Green, LC Green Plus and Syto 9.

Additional Exemplary

TABLE 1

Exemplary fluorescent dyes and compatible quenchers suitable for detection of real time PCR products. Abbreviations: HEX: 6-carboxy-2',4,4',5',7,7'-hexachlorofluorescein, succinimidyl ester; 6-FAM: 6-carboxyfluorescein; ROX: 6-ROXN (6-carboxy-X-rhodamine); BHQ-1: Black Hole Quencher 1, Biosearch Technologies, Inc., Novato, CA; BHQ-2: Black Hole Quencher 2, Biosearch Technologies, Inc., Novato, CA; BHQ-3: Black Hole Quencher 3, Biosearch Technologies, Inc., Novato, CA.

| Dye | Max Excitation (nm) | Max Emission (nm) | Compatible Quencher(s) |
| --- | --- | --- | --- |
| 6-FAM | 494 | 515 | BHQ-1, TAMRA |
| JOE | 520 | 548 | BHQ-1, TAMRA |
| TET | 521 | 536 | BHQ-1, TAMRA |
| Cal Fluor Gold 540 | 520 | 548 | BHQ-1 |
| HEX | 535 | 555 | BHQ-1, TAMRA |
| Cal Fluor Orange 560 | 522 | 541 | BHQ-1 |
| TAMRA | 555 | 576 | BHQ-2 |
| Cy3 | 550 | 570 | BHQ-2 |
| Quasar 570 | 548 | 566 | BHQ-2 |
| Cal Fluor Red 590 | 565 | 588 | BHQ-2 |
| ROX | 573 | 602 | BHQ-2 |
| Texas Red | 583 | 603 | BHQ-2 |
| Cy5 | 651 | 674 | BHQ-3 |
| Quasar 670 | 647 | 667 | BHQ-3 |
| Cy5.5 | 675 | 694 | BHQ-3 |

TaqMan requires producing double-labeled probes specific for each product, which can increase the cost of TaqMan-based real-time PCR system. However, unlike SYBR Green I, TaqMan can readily be utilized for multiplex PCR since a reaction can contain multiple TaqMan probes, each specific for a particular amplicon and each utilizing a distinguishable fluorophore.

In addition, biomarker expression levels may be determined using a microarray, optionally together with amplification of sample nucleic acids (e.g., as described in the preceding paragraphs). A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637, each of which is hereby incorporated by reference in its entirety). Microarray technology allows for the measurement of the steady-state level of large numbers of polynucleotide sequences simultaneously. Microarrays currently in wide use include cDNA arrays and oligonucleotide arrays.

cDNA microarrays consist of multiple (e.g., thousands) of different cDNAs spotted (e.g., using a robotic spotting device) onto known locations on a solid support, such as a glass microscope slide, onto which the probes are covalently or non-covalently attached. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kB in length. In a typical microarray experiment, RNA (either total RNA or poly A RNA) is isolated from cells or tissues of interest and is reverse transcribed to yield cDNA. Labeling is usually performed during reverse transcription by incorporating a labeled nucleotide in the reaction mixture. A microarray is then hybridized with labeled RNA, and relative expression levels calculated based on the relative concentrations of cDNA molecules that hybridized to the cDNAs represented on the microarray. Microarray analysis can be performed by commercially available equipment, following manufacturer's protocols, such as, e.g., by using Affymetrix GeneChip® technology, Agilent Technologies cDNA microarrays, Illumina Whole-Genome DASL® array assays, or any other comparable microarray technology.

Probes capable of hybridizing to one or more biomarker RNAs or cDNAs may be attached to the substrate at a defined location ("addressable array"). Probes can be attached to the substrate in a wide variety of ways, as will be appreciated by those in the art. In some embodiments, the probes are synthesized first and subsequently attached to the substrate. In other embodiments, the probes are synthesized on the substrate. In some embodiments, probes are synthesized on the substrate surface using techniques such as photopolymerization and photolithography.

In some embodiments, microarrays are utilized in a RNA-primed, Array-based Klenow Enzyme ("RAKE") assay. See Nelson, P. T. et al. (2004) Nature Methods 1(2):1-7; Nelson, P. T. et al. (2006) RNA 12(2):1-5, each of which is incorporated herein by reference in its entirety. In these embodiments, total RNA is isolated from a sample. Optionally, small RNAs can be further purified from the total RNA sample. The RNA sample is then hybridized to DNA probes immobilized at the 5'-end on an addressable array. The DNA probes comprise a base sequence that is complementary to a target RNA of interest, such as one or more biomarker RNAs capable of specifically hybridizing to a nucleic acid comprising a sequence that is identically present in one of the genes of interest under standard hybridization conditions.

Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). For example, fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with the robust multichip average (RMA) algorithm to generate expression values. Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

In one embodiment, the primers are contained in one or more wells of a multi-well reaction vessel. In another embodiment, the primers for amplification of at least two of said genes are included together in a duplex or multiplex reaction.

The invention further may preferably include a web based system for analysis of the gene expression data. After running the preferred amplification array, e.g., PCR, a user will determine the regulatory status of a target sample and a control sample. In a preferred embodiment a user will effect comparison and analysis by the use of an available web based analysis tool or equivalent. In the context of the present invention this tool may in addition provide users with a number (index, probability or analogous parameter) which will indicate the relative regulatory status of a particular treatment sample compared to an appropriate control sample.

Applications of Present Invention

Diagnostic/Sample Classification Methods

The invention provides for methods of using the biomarker sets to analyze a sample from an individual or subject so as to determine or classify the subject's sample at a molecular level, to determine the regulation status of the IL-6/STAT3 pathway. The sample may or may not be derived from a tumor. The individual need not actually be afflicted with cancer, non-cancer inflammatory conditions, and/or any other disease. Essentially, the expression of specific biomarker genes in the individual, or a sample taken therefrom, is compared to a standard or control. For example, assume two cancer-related conditions, X and Y. One can compare the level of expression of IL-6/STAT3 pathway biomarkers for condition X in an individual to the level of the biomarker-derived polynucleotides in a control, wherein the level represents the level of expression exhibited by samples having condition X. In this instance, if the expression of the markers in the individual's sample is substantially (i.e., statistically) different from that of the control, then the individual does not have condition X. Where, as here, the choice is bimodal (i.e., a sample is either X or Y), the individual can additionally be said to have condition Y. Of course, the comparison to a control representing condition Y can also be performed. Preferably, both are performed simultaneously, such that each control acts as both a positive and a negative control. The distinguishing result may thus either be a demonstrable difference from the expression levels (i.e. the amount of marker-derived RNA, or polynucleotides derived therefrom) represented by the control, or no significant difference.

Thus, in one embodiment, the method of determining a particular tumor-related status of an individual comprises the steps of (1) hybridizing labeled target polynucleotides from an individual to a microarray containing the above biomarker set or a subset of the biomarkers; (2) hybridizing standard or control polynucleotide molecules to the microarray, wherein the standard or control molecules are differentially labeled from the target molecules; and (3) determining the difference in transcript levels, or lack thereof, between the target and standard or control, wherein the difference, or lack thereof, determines the individual's tumor-related status.

In a more specific embodiment, the standard or control molecules comprise biomarker-derived polynucleotides from a pool of samples from normal individuals, a pool of samples from normal adjacent tissue, or a pool of tumor samples from individuals with cancer. In a preferred embodiment, the standard or control is artificially-generated pool of biomarker-derived polynucleotides, which pool is designed to mimic the level of biomarker expression exhibited by clinical samples of normal or cancer tumor tissue having a particular clinical indication (e.g., cancerous or non-cancerous; IL-6/STAT3 pathway regulated or deregulated). In another specific embodiment, the control molecules comprise a pool derived from normal or cancer cell lines.

The present invention provides a set of biomarkers or a microarray containing useful for distinguishing the regulation status of the IL-6/STAT3 pathway, e.g., in a cell sample (tumor). Thus, in one embodiment of the above method, the level of polynucleotides (i.e., mRNA or polynucleotides derived therefrom) in a sample from an individual, expressed from the 16 biomarkers provided herein are compared to the level of expression of the same biomarkers from a control. If the purpose is to identify whether a compound affects IL-6/STAT3 signaling, then the control may comprise a sample treated by the same methods except in the absence of the compound.

The comparison alternatively may be to both deregulated and regulated IL-6/STAT3 signaling pathway tumor samples, and the comparison may be to polynucleotide pools from a number of deregulated and regulated IL-6/STAT3 signaling pathway tumor samples, respectively. Where the individual's biomarker expression most closely resembles or correlates with the deregulated control, and does not resemble or correlate with the regulated control, the individual is classified as having a deregulated IL-6/STAT3 signaling pathway. Where the pool is not pure deregulated or regulated IL-6/STAT3 signaling pathway type tumors samples, for example, a sporadic pool is used, a set of experiments using individuals with known IL-6/STAT3 signaling pathway status may be hybridized against the pool in order to define the expression templates for the deregulated and regulated group. Each individual with unknown IL-6/STAT3 signaling pathway status is hybridized against the same pool and the expression profile is compared to the template(s) to determine the individual's IL-6/STAT3 signaling pathway status. As noted in the preferred methods the expression of the biomarkers is effected by use of RT-PCR.

In another specific embodiment, the method comprises:
(1) calculating a measure of similarity between a first expression profile and a deregulated IL-6/STAT3 signaling pathway template, or calculating a first measure of similarity between said first expression profile and said deregulated IL-6/STAT3 signaling pathway template and a second measure of similarity between said first expression profile and a regulated IL-6/STAT3 signaling pathway template, said first expression profile comprising the expression levels of a first plurality of genes in the cell sample, said deregulated IL-6/STAT3 signaling pathway template comprising expression levels of said first plurality of genes that are average expression levels of the respective genes in a plurality of cell samples having at least one or more components of said IL-6/STAT3 signaling pathway with abnormal activity, and said regulated IL-6/STAT3 signaling pathway template comprising expression levels of said first plurality of genes that are average expression levels of the respective genes in a plurality of cell samples not having at least one or more components of said IL-6/STAT3 signaling pathway with abnormal activity, said first plurality of genes consisting of at least 5 of the genes for which biomarkers are listed herein;

(2) classifying said cell sample as having said deregulated IL-6/STAT3 signaling pathway if said first expression profile has a high similarity to said deregulated IL-6/STAT3 signaling pathway template or has a higher similarity to said deregulated IL-6/STAT3 signaling pathway template than to said regulated IL-6/STAT3 signaling pathway template, or classifying said cell sample as having said regulated IL-6/STAT3 signaling pathway if said first expression profile has a low similarity to said deregulated IL-6/STAT3 signaling pathway template or has a higher similarity to said regulated IL-6/STAT3 signaling pathway template than to said deregulated IL-6/STAT3 signaling pathway template; wherein said first expression profile has a high similarity to said deregulated IL-6/STAT3 signaling pathway template if the similarity to said deregulated IL-6/STAT3 signaling pathway template is above a predetermined threshold, or has a low similarity to said deregulated IL-6/STAT3 signaling pathway template if the similarity to said deregulated IL-6/STAT3 signaling pathway template is below said predetermined threshold; and (3) displaying; or outputting to a user interface device, a computer readable storage medium, or a local or remote computer system; the classification produced by said classifying step (2).

In another specific embodiment, the set of biomarkers may be used to classify a sample from a subject by the IL-6/STAT3 signaling pathway regulation status. The sample may or may not be derived from a tumor. Thus, in one embodiment of the above method, the level of polynucleotides (i.e., mRNA or polynucleotides derived therefrom) in a sample from an individual, expressed from the biomarkers provided herein are compared to the level of expression of the same biomarkers from a control, wherein the control comprises biomarker-related polynucleotides derived from deregulated IL-6/STAT3 signaling pathway samples, regulated IL-6/STAT3 signaling pathway samples, or both. The comparison may be to both deregulated and regulated IL-6/STAT3 signaling pathway samples, and the comparison may be to polynucleotide pools from a number of deregulated and regulated IL-6/STAT3 signaling pathway samples, respectively. The comparison may also be made to a mixed pool of samples with deregulated and regulated IL-6/STAT3 signaling pathway or unknown samples.

For the above embodiments, the full set of biomarkers may be used (i.e., the complete set of 16 biomarkers). In other embodiments, subsets of the 16 biomarkers may be used, e.g., 1-15 of the 16 biomarkers, at least 5 of the 16 biomarkers, at least 10-15 of the biomarkers.

In another embodiment, the expression profile is a differential expression profile comprising differential measurements of said plurality of genes in a sample derived from a subject versus measurements of said plurality of genes in a control sample. The differential measurements can be xdev, log(ratio), error-weighted log(ratio), or a mean subtracted log(intensity) (see, e.g., PCT publication WO00/39339, published on Jul. 6, 2000; PCT publication WO2004/065545, published Aug. 5, 2004, each of which is incorporated herein by reference in its entirety). The similarity between the biomarker expression profile of a sample or an individual and that of a control can be assessed a number of ways using any method known in the art. For example, Dai et al. describe a number of different ways of calculating gene expression templates and corresponding biomarker genets useful in classifying breast cancer patients (U.S. Pat. No. 7,171,311; WO2002/103320; WO2005/086891; WO2006015312; WO2006/084272). Similarly, Linsley et al. (US2003/0104426) and Radish et al. (US20070154931)

disclose gene biomarker genesets and methods of calculating gene expression templates useful in classifying chronic myelogenous leukemia patients. In the simplest case, the profiles can be compared visually in a printout of expression difference data. Alternatively, the similarity can be calculated mathematically.

In one embodiment, the similarity is represented by a correlation coefficient between the patient or sample profile and the template. In one embodiment, a correlation coefficient above a correlation threshold indicates high similarity, whereas a correlation coefficient below the threshold indicates low similarity. In some embodiments, the correlation threshold is set as 0.3, 0.4, 0.5, or 0.6. In another embodiment, similarity between a sample or patient profile and a template is represented by a distance between the sample profile and the template. In one embodiment, a distance below a given value indicates a high similarity, whereas a distance equal to or greater than the given value indicates low similarity.

Thus, in a more specific embodiment, the above method of determining a particular tumor-related status of an individual comprises the steps of (1) hybridizing labeled target polynucleotides from an individual to a microarray containing one of the above marker sets; (2) hybridizing standard or control polynucleotides molecules to the microarray, wherein the standard or control molecules are differentially labeled from the target molecules; and (3) determining the ratio (or difference) of transcript levels between two channels (individual and control), or simply the transcript levels of the individual; and (4) comparing the results from (3) to the predefined templates, wherein said determining is accomplished by any means known in the art, and wherein the difference, or lack thereof, determines the individual's tumor-related status. The method can use the complete set of 16 biomarkers. However, subsets of the 16 biomarkers may also be used (e.g., at least 5 of the 16 biomarkers, at least 10-15 of the biomarkers).

In yet another embodiment, the signature score of a sample is defined as the average expression level (such as mean log(ratio)) of the complete set of 16 biomarkers or a subset of these biomarkers. If the signature score for a sample is above a pre-determined threshold, then the sample is considered to have deregulation of the IL-6/STAT3 signaling pathway. The pre-determined threshold may be 0, or may be the mean, median, or a percentile of signature scores of a collection of samples or a pooled sample used as a standard or control.

The use of the biomarkers is not limited to distinguishing or classifying particular tumor types, such as liver cancer, as having deregulated or regulated IL-6/STAT3 signaling pathway. The biomarkers may be used to classify cell samples from any cancer type, where aberrant IL-6/STAT3 signaling may be implicated such as lung, breast, esophageal, head and neck, colonic, gastrointestinal, prostate, multiple myeloma, hepatic, ovarian, neuroblastoma, glioblastoma, melanoma, pancreatic adenocarcinoma, renal cell carcinoma, cholangiocellular carcinoma, and various leukemias and lymphomas. Non-limiting examples thereof include low grade/follicular non-Hodgkin's lymphoma (NHL), small lymphocytic (SL) NHL, intermediate grade/follicular NHL, intermediate grade diffuse NHL, chronic lymphocytic leukemia (CLL), high grade immunoblastic NHL, high grade lymphoblastic NHL, high grade small noncleaved cell NHL, bulky disease NHL, mantle cell lymphoma, AIDS-related lymphoma, Waldenstrom's Macroglobulinemia and T cell lymphomas and leukemias The use of the biomarkers is also not restricted to distinguishing or classifying cell samples as having deregulated or regulated IL-6/STAT3 signaling pathway for cancer-related conditions, and may be applied in a variety of phenotypes or conditions, in which aberrant IL-6/STAT3 signaling plays a role, or the level of IL-6/STAT3 signaling activity is sought. For example, the biomarkers may be useful for classifying samples for non-cancer inflammatory conditions, including, but not limited to, hypoferremia of inflammation, acute-phase response to inflammation and infection, chronic inflammation, inflammation in cardiovascular, systemic juvenile rheumatoid arthritis, *Staphylococcus epidermidis*-induced peritoneal inflammation, and pulmonary inflammation, e.g., adult respiratory distress syndrome, shock lung, chronic pulmonary inflammatory disease, pulmonary sarcoidosis, pulmonary fibrosis and silicosis. The IL-6/STAT3 signaling pathway has previously been implicated in the inflammatory response (Grivennikov S I, Karin M. Dangerous liaisons: STAT3 and NF-kappaB collaboration and crosstalk in cancer. Cytokine Growth Factor Rev. 2010 February; 21(1):11-9. Epub 2009 Dec. 16); biological events such as, e.g., embryonic development, programmed cell death, organogenesis, innate immunity, adaptive immunity and cell growth regulation in many organisms (Mankan A K, Greten F R. Inhibiting signal transducer and activator of transcription 3: rationality and rationale design of inhibitors. Expert Opin Investig Drugs. 2011 September; 20(9):1263-75. Epub 2011 Jul. 14); and cancer initiation and progression (Yu H, Pardoll D, Jove R. STATs in cancer inflammation and immunity: a leading role for STAT3. Nat Rev Cancer. 2009 November; 9(11):798-809).

Methods of Predicting Response to Treatment and Assigning Treatment

The invention provides a set of biomarkers useful for distinguishing samples from those patients likely to respond to treatment with an agent that modulates the IL-6/STAT3 signaling pathway, from patients who are not likely to respond to treatment an agent that modulates the IL-6/STAT3 signaling pathway. Thus, the invention further provides a method for using these biomarkers for determining whether an individual with cancer is a predicted responder to treatment with an agent that modulates the IL-6/STAT3 signaling pathway. In one embodiment, the invention provides for a method of predicting response of a cancer patient to an agent that modulates the IL-6/STAT3 signaling pathway comprising (1) comparing the level of expression of the 16 biomarkers in a sample taken from the individual to the level of expression of the same biomarkers in a standard or control, where the standard or control levels represent those found in a sample having a deregulated IL-6/STAT3 signaling; and (2) determining whether the level of the biomarker-related polynucleotides in the sample from the individual is significantly different than that of the control, wherein if no substantial difference is found, the patient is predicted to respond to treatment with an agent that modulates the IL-6/STAT3 signaling pathway, and if a substantial difference is found, the patient is predicted not to respond to treatment with an agent that modulates the IL-6/STAT3 signaling pathway. Persons of skill in the art will readily see that the standard or control levels may be from a sample having a regulated IL-6/STAT3 signaling pathway. In a more specific embodiment, both controls are run. In case the pool is not pure "IL-6/STAT3 regulated" or "IL-6/STAT3 deregulated," a set of experiments of individuals with known responder status may be hybridized against the pool to define the expression templates for the predicted responder and predicted non-responder group. Each individual with unknown outcome is hybridized against the same pool and the resulting expression profile is compared to the templates to predict its outcome.

IL-6/STAT3 signaling pathway deregulation status of a tumor may indicate a subject that is responsive to treatment with an agent that modulates the IL-6/STAT3 signaling pathway. Therefore, the invention provides for a method of determining or assigning a course of treatment of a cancer patient, comprising determining whether the level of expression of the 16 biomarkers, or a subset thereof, correlates with the level of these biomarkers in a sample representing deregulated IL-6/STAT3 signaling pathway status or regulated IL-6/STAT3 signaling pathway status; and determining or assigning a course of treatment, wherein if the expression correlates with the deregulated IL-6/STAT3 signaling pathway status pattern, the tumor is treated with an agent that modulates the IL-6/STAT3 signaling pathway.

As with the diagnostic biomarkers, the method can preferably use the complete set of 16 biomarkers. However, subsets of the 16 biomarkers may also be used (e.g., at least 5 of the 16 biomarkers, at least 10-15 of the biomarkers).

Classification of a sample as "predicted responder" or "predicted non-responder" is accomplished substantially as for the diagnostic biomarkers described above, wherein a template is generated to which the biomarker expression levels in the sample are compared.

In another embodiment, the above method for measuring the effect of an agent on the IL-6/STAT3 signaling pathway is preferably determined after real-time PCR measuring expression levels of 16 biomarker genes using SYBR Green, and a $\Delta\Delta CT$ method employed to analysis the data. The average CT values of house keeping genes in each sample, e.g., 8 housekeeping genes, is calculated as house keeping gene CT value for that sample. $\Delta CT$ was calculated by subtracting house keeping CT value from individual assay CT value of same sample. $\Delta\Delta CT$ value was derived by further subtracting $\Delta CT$ value of control samples of each assay from its corresponding $\Delta CT$ value of treatment sample. This $\Delta\Delta CT$ value of those 16 genes is then compared to $\Delta\Delta CT$ value of 16 genes in a training data pool that contains several samples, e.g., 16 total sample, 7 of which are negatively regulated and 9 of which are positively regulated in terms of pathway activity. A random forest method is preferably used to analyze the $\Delta\Delta CT$ values of the samples and the expression thereof used to assess the regulatory status of the IL-6/STAT3 pathway activity in the sample.

The use of the biomarkers is not restricted to predicting response to agents that modulate IL-6/STAT3 signaling pathway for cancer-related conditions, and may be applied in a variety of phenotypes or conditions, clinical or experimental, in which gene expression plays a role. Where a set of biomarkers has been identified that corresponds to two or more phenotypes, the biomarker sets can be used to distinguish these phenotypes. For example, the phenotypes may be the diagnosis and/or prognosis of clinical states or phenotypes associated with cancers and other disease conditions, or other physiological conditions, prediction of response to agents that modulate pathways other than the IL-6/STAT3 signaling pathway, wherein the expression level data is derived from a set of genes correlated with the particular physiological or disease condition.

The use of the biomarkers is not limited to predicting response to agents that modulate IL-6/STAT3 signaling pathway for a particular cancer type, such as liver cancer. The biomarkers may be used to predict response to agents in any cancer type where aberrant IL-6/STAT3 signaling may be implicated. Aberrant IL-6/STAT3 pathway signaling has been discovered in a wide variety of cancers, including lung, breast, esophageal, head and neck, colonic, gastrointestinal, prostate, multiple myeloma, hepatic, ovarian, neuroblastoma, glioblastoma, melanoma, pancreatic adenocarcinoma, renal cell carcinoma, cholangiocellular carcinoma, and various leukemias and lymphomas.

The use of the biomarkers is also not restricted to predicting response to agents that modulate IL-6/STAT3 signaling pathway for cancer-related conditions, and may be applied in a variety of phenotypes or conditions, in which aberrant IL-6/STAT3 signaling plays a role, or the level of IL-6/STAT3 signaling activity is sought. For example, the biomarkers may be useful for classifying samples for non-cancer inflammatory conditions, such as, but not limited to, hypoferremia of inflammation, acute-phase response to inflammation and infection, chronic inflammation, inflammation in cardiovascular, systemic juvenile rheumatoid arthritis, *Staphylococcus epidermidis*-induced peritoneal inflammation, and pulmonary inflammation, e.g., adult respiratory distress syndrome, shock lung, chronic pulmonary inflammatory disease, pulmonary sarcoidosis, pulmonary fibrosis and silicosis. The IL-6/STAT3 signaling pathway has previously been implicated in the inflammatory response (Grivennikov S I, Karin M. Dangerous liaisons: STAT3 and NF-kappaB collaboration and crosstalk in cancer. Cytokine Growth Factor Rev. 2010 February; 21(1):11-9. Epub 2009 Dec. 16); biological events such as, e.g., embryonic development, programmed cell death, organogenesis, innate immunity, adaptive immunity and cell growth regulation in many organisms (Mankan A K, Greten F R. Inhibiting signal transducer and activator of transcription 3: rationality and rationale design of inhibitors. Expert Opin Investig Drugs. 2011 September; 20(9):1263-75. Epub 2011 Jul. 14); and cancer initiation and progression (Yu H, Pardo11 D, Jove R. STATs in cancer inflammation and immunity: a leading role for STAT3. Nat Rev Cancer. 2009 November; 9(11):798-809). Additionally, the biomarkers can be used to detect inflammation sites in vivo or ex vivo.

Method of Determining Whether an Agent Modulates the IL-6/STAT3 Signaling Pathway The invention provides a set of biomarkers useful for and methods of using the biomarkers for identifying or evaluating an agent that is predicted to modify or modulate the IL-6/STAT3 signaling pathway in a subject. "IL-6/STAT3 signaling pathway" is initiated by the cytokine IL-6 binding to the IL-6 receptor (IL-6R), and this engagement of IL6 to its specific receptor activates receptor-associated tyrosine kinase Janus Kinase 2 (JAK2), which in turn phosphorylates tyrosine residues in the cytoplasmic tail of the IL-6R that function as docking sites for STAT3. JAK2-dependent phosphorylation of STAT3 leads to its homodimerization and nuclear translocation. Once in the nucleus, activated STAT3 functions as transcriptional activator, inducing expression of target genes (Levy D E, Darnell JE Jr. Stats: transcriptional control and biological impact. Nat Rev Mal Cell Biol. 2002 September; 3(9):651-62). STAT3 induces expression of a large number of genes having a STAT3 binding site, including genes involved in cell survivial, cell proliferation, invasion, angiogenesis, and tumor immune evasion (e.g., cyclin DI, p53, Bcl-Xl, MMP-2, MMP-9, VEGF, bFGF, HIF-1 alpha, IP-10, and RANTES) and feedback regulation of the pathway (e.g., SOCS3).

Agents affecting the IL-6/STAT3 signaling pathway include small molecule compounds; proteins or peptides (including antibodies); siRNA, shRNA, or microRNA molecules; or any other agents that modulate one or more genes or proteins that function within the IL-6/STAT3 signaling pathway or other signaling pathways that interact with the IL-6/STAT3 signaling pathway, such as the Notch pathway.

"IL-6/STAT3 pathway agent" refers to an agent which modulates the IL-6/STAT3 pathway signaling. A IL-6/STAT3 pathway inhibitor inhibits the IL-6/STAT3 pathway signaling. Molecular targets of such agents may include JAK2 and STAT3, as well as any of the genes listed herein. Such agents are known in the art and include, but are not limited to: AZD1480 (Hedvat et al., The JAK2 Inhibitor, AZD1480, Potently Blocks Stat3 Signaling and Oncogenesis in Solid Tumors. Cancer Cell. 2009 Dec. 8; 16(6):487-97), WP1066 (Calbiochem, La Jolla, Calif., USA), NSC 74859, Stattic (Santa Cruz Biotechnology, Inc.; Schust et al., Stattic: A Small Molecule Inhibitor of STAT3 Activation and Dimerization. Chemistry & Biology. 2006; 13:1235-1242), and LLL12 (Liu et al., Inhibition of STAT3 signaling blocks the anti-apoptotic activity of IL-6 in human liver cancer cells. J Biol Chem, 285:27429-39, Epub 2010 Jun. 18).

In one embodiment, the method for measuring the effect or determining whether an agent modulates the IL-6/STAT3 signaling pathway comprises: (1) comparing the level of expression of the 16 biomarkers in a sample treated with an agent to the level of expression of the same biomarkers in a standard or control, wherein the standard or control levels represent those found in a vehicle-treated sample; and (2) determining whether the level of the biomarker-related polynucleotides in the treated sample is significantly different than that of the vehicle-treated control, wherein if no substantial difference is found, the agent is predicted not to have an modulate the IL-6/STAT3 signaling pathway, and if a substantial difference is found, the agent is predicted to modulate the IL-6/STAT3 signaling pathway.

In another embodiment, the above method for measuring the effect of an agent on the TL-6/STAT3 signaling pathway is preferably determined after real-time PCR measuring expression levels of 16 biomarker genes (e.g., using SYBR green), and a ΔΔCT method employed to analysis the data. The average CT values of house keeping genes in each sample is calculated as house keeping gene CT value for that sample. ΔCT was calculated by subtracting house keeping CT value from individual assay CT value of same sample. ΔΔCT value was derived by further subtracting ΔCT value of control samples of each assay from its corresponding ΔCT value of treatment sample. This ΔΔCt value of those 16 genes is then compared to ΔΔCt value of 16 genes in a training data pool that contains several samples (e.g., 16 total sample, 7 negatively regulated and 9 positively regulated in terms of pathway activity). A random forest method is preferably used to analyze the ΔΔCT values of the samples and the expression thereof used to assess the regulatory status of the IL-6/STAT3 pathway activity in the sample.

The use of the biomarkers is not restricted to determining whether an agent modulates IL-6/STAT3 signaling pathway for cancer-related conditions, and may be applied in a variety of phenotypes or conditions, clinical or experimental, in which gene expression plays a role. Where a set of biomarkers has been identified that corresponds to two or more phenotypes, the biomarker sets can be used to distinguish these phenotypes. For example, the phenotypes may be the diagnosis and/or prognosis of clinical states or phenotypes associated with cancers and other disease conditions, or other physiological conditions, prediction of response to agents that modulate pathways other than the IL-6/STAT3 signaling pathway, wherein the expression level data is derived from a set of genes correlated with the particular physiological or disease condition.

The use of the biomarkers is not limited to determining whether an agent modulates the IL-6/STAT3 signaling pathway for a particular cancer type, such as liver cancer. The biomarkers may be used to determine whether an agent modulates the IL-6/STAT3 for any cancer type, where aberrant IL-6/STAT3 signaling may be implicated. Aberrant IL-6/STAT3 pathway signaling has been discovered in a wide variety of cancers, including lung, breast, esophageal, head and neck, colonic, gastrointestinal, prostate, multiple myeloma, hepatic, ovarian, neuroblastoma, glioblastoma, melanoma, pancreatic adenocarcinoma, renal cell carcinoma, cholangiocellular carcinoma, and various leukemias, and lymphomas.

The use of the biomarkers is also not restricted determining whether an agent modulates the IL-6/STAT3 signaling pathway for cancer-related conditions, and may be applied for agents for a variety of phenotypes or conditions, in which aberrant IL-6/STAT3 signaling plays a role, or the level of IL-6/STAT3 signaling activity is sought. For example, the biomarkers may be useful for classifying samples for non-cancer inflammatory conditions, such as, but not limited to, hypoferremia of inflammation, acute-phase response to inflammation and infection, chronic inflammation, inflammation in cardiovascular, systemic juvenile rheumatoid arthritis, *Staphylococcus epidermidis*-induced peritoneal inflammation, and pulmonary inflammation, e.g., adult respiratory distress syndrome, shock lung, chronic pulmonary inflammatory disease, pulmonary sarcoidosis, pulmonary fibrosis and silicosis. The IL-6/STAT3 signaling pathway has previously been implicated in the inflammatory response (Grivennikov S I, Karin M. Dangerous liaisons: STAT3 and NF-kappaB collaboration and crosstalk in cancer. Cytokine Growth Factor Rev. 2010 February; 21(1):11-9. Epub 2009 Dec. 16); biological events such as, e.g., embryonic development, programmed cell death, organogenesis, innate immunity, adaptive immunity and cell growth regulation in many organisms (Mankan A K, Greten F R. Inhibiting signal transducer and activator of transcription 3: rationality and rationale design of inhibitors. Expert Opin Investig Drugs. 2011 September; 20(9):1263-75. Epub 2011 Jul. 14); and cancer initiation and progression (Yu H, Pardoll D, Jove R. STATs in cancer inflammation and immunity: a leading role for STAT3. Nat Rev Cancer. 2009 November; 9(11):798-809). Additionally, the biomarkers can be used to detect inflammation sites in vivo or ex vivo.

Method of Measuring Pharmacodynamic Effect of an Agent

The invention provides a set of biomarkers useful for measuring the pharmacodynamic effect of an agent on the IL-6/STAT3 signaling pathway. The biomarkers provided may be used to monitor modulation of the IL-6/STAT3 signaling pathway at various time points following treatment with said agent in a patient or sample. Thus, the invention further provides a method for using these biomarkers as an early evaluation for efficacy of an agent which modulates the IL-6/STAT3 signaling pathway. In one embodiment, the invention provides for a method of measuring pharmacodynamic effect of an agent that modulates the IL-6/STAT3 signaling pathway in patient or sample comprising: (1) comparing the level of expression of the 16 biomarkers in a sample treated with an agent to the level of expression of the same biomarkers in a standard or control, wherein the standard or control levels represent those found in a vehicle-treated sample; and (2) determining whether the level of the biomarker-related polynucleotides in the treated sample is significantly different than that of the vehicle-treated control, wherein if no substantial difference is found, the agent is predicted not to have an pharmacodynamic effect on the IL-6/STAT3 signaling pathway, and if a substantial difference is found, the agent is predicted to have an pharmacodynamic effect on the IL-6/STAT3 signaling pathway. In another specific embodiment, the invention provides a subset of at least 5 biomarkers, or at least 10 biomarkers, drawn from the set of 16 that can be used to monitor pharmacodynamic activity of an agent on the IL-6/STAT3 signaling pathway.

In another embodiment, the above method for measuring the effect of an agent on the IL-6/STAT3 signaling pathway is preferably determined after real-time PCR measuring expression levels of 16 biomarker genes (e.g., using SYBR green detection), and a $\Delta\Delta CT$ method employed to analysis the data. The average CT values of house keeping genes in each sample is calculated as house keeping gene CT value for that sample. $\Delta CT$ was calculated by subtracting house keeping CT value from individual assay CT value of same sample. $\Delta\Delta CT$ value was derived by further subtracting $\Delta CT$ value of control samples of each assay from its corresponding $\Delta CT$ value of treatment sample. This $\Delta\Delta Ct$ value of those 16 genes is then compared to $\Delta\Delta Ct$ value of 16 genes in a training data pool that contains several samples (e.g., 16 total sample, 7 negatively regulated and 9 positively regulated in terms of pathway activity). A random forest method is preferably used to analyze the $\Delta\Delta CT$ values of the samples and the expression thereof used to assess the regulatory status of the IL-6/STAT3 pathway activity in the sample.

Improving Sensitivity to Expression Level Differences

In using the biomarkers disclosed herein, and, indeed, using any sets of biomarkers to differentiate an individual or subject having one phenotype from another individual or subject having a second phenotype, one can compare the absolute expression of each of the biomarkers in a sample to a control; for example, the control can be the average level of expression of each of the biomarkers, respectively, in a pool of individuals or subjects. To increase the sensitivity of the comparison, however, the expression level values are preferably transformed in a number of ways.

For example, the expression level of each of the biomarkers can be normalized by the average expression level of all markers the expression level of which is determined, or by the average expression level of a set of control genes. Thus, in one embodiment, the biomarkers are represented by probes on a microarray, and the expression level of each of the biomarkers is normalized by the mean or median expression level across all of the genes represented on the microarray, including any non-biomarker genes. In a specific embodiment, the normalization is carried out by dividing the median or mean level of expression of all of the genes on the microarray. In another embodiment, the expression levels of the biomarkers is normalized by the mean or median level of expression of a set of control biomarkers. In a specific embodiment, the control biomarkers comprise a set of housekeeping genes. In another specific embodiment, the normalization is accomplished by dividing by the median or mean expression level of the control genes.

The sensitivity of a biomarker-based assay will also be increased if the expression levels of individual biomarkers are compared to the expression of the same biomarkers in a pool of samples. Preferably, the comparison is to the mean or median expression level of each the biomarker genes in the pool of samples. Such a comparison may be accomplished, for example, by dividing by the mean or median expression level of the pool for each of the biomarkers from the expression level each of the biomarkers in the sample. This has the effect of accentuating the relative differences in expression between biomarkers in the sample and markers in the pool as a whole, making comparisons more sensitive and more likely to produce meaningful results that the use of absolute expression levels alone. The expression level data may be transformed in any convenient way: preferably, the expression level data for all is log transformed before means or medians are taken.

In performing comparisons to a pool, two approaches may be used. First, the expression levels of the markers in the sample may be compared to the expression level of those markers in the pool, where nucleic acid derived from the sample and nucleic acid derived from the pool are hybridized during the course of a single experiment. Such an approach requires that new pool nucleic acid be generated for each comparison or limited numbers of comparisons, and is therefore limited by the amount of nucleic acid available. Alternatively, and preferably, the expression levels in a pool, whether normalized and/or transformed or not, are stored on a computer, or on computer-readable media, to be used in comparisons to the individual expression level data from the sample (i.e., single-channel data).

Thus, the current invention provides the following method of classifying a first cell or organism as having one of at least two different phenotypes, where the different phenotypes comprise a first phenotype and a second phenotype. The level of expression of each of a plurality of genes in a first sample from the first cell or organism is compared to the level of expression of each of said genes, respectively, in a pooled sample from a plurality of cells or organisms, the plurality of cells or organisms comprising different cells or organisms exhibiting said at least two different phenotypes, respectively, to produce a first compared value. The first compared value is then compared to a second compared value, wherein said second compared value is the product of a method comprising comparing the level of expression of each of said genes in a sample from a cell or organism characterized as having said first phenotype to the level of expression of each of said genes, respectively, in the pooled sample. The first compared value is then compared to a third compared value, wherein said third compared value is the product of a method comprising comparing the level of expression of each of the genes in a sample from a cell or organism characterized as having the second phenotype to the level of expression of each of the genes, respectively, in the pooled sample. Optionally, the first compared value can be compared to additional compared values, respectively, where each additional compared value is the product of a method comprising comparing the level of expression of each of said genes in a sample from a cell or organism characterized as having a phenotype different from said first and second phenotypes out included among the at least two different phenotypes, to the level of expression of each of said genes, respectively, in said pooled sample. Finally, a determination is made as to which of said second, third, and, if present, one or more additional compared values, said first compared value is most similar, wherein the first cell or organism is determined to have the phenotype of the cell or organism used to produce said compared value most similar to said first compared value.

In a specific embodiment of this method, the compared values are each ratios of the levels of expression of each of said genes. In another specific embodiment, each of the levels of expression of each of the genes in the pooled sample is normalized prior to any of the comparing steps. In a more specific embodiment, the normalization of the levels of expression is carried out by dividing by the median or mean level of expression of each of the genes or dividing by the mean or median level of expression of one or more housekeeping genes in the pooled sample from said cell or organism. In another specific embodiment, the normalized levels of expression are subjected to a log transform, and the comparing steps comprise subtracting the log transform from the log of the levels of expression of each of the genes in the sample. In another specific embodiment, the two or more different phenotypes are different regulation status of the IL-6/STAT3 signaling pathway. In still another specific embodiment, the two or more different phenotypes are different predicted responses to treatment with an agent that modulates the IL-6/STAT3 signaling pathway. In yet another specific embodiment, the levels of expression of each of the genes, respectively, in the pooled sample or said levels of expression of each of said genes in a sample from the cell or organism characterized as having the first phenotype, second phenotype, or said phenotype different from said first and second phenotypes, respectively, are stored on a computer or on a computer-readable medium.

In another specific embodiment, the two phenotypes are deregulated or IL-6/STAT3 signaling pathway status. In another specific embodiment, the two phenotypes are predicted IL-6/STAT3 signaling pathway-agent responder status. In yet another specific embodiment, the two phenotypes are pharmacodynamic effect and no pharmacodynamic effect of an agent on the IL-6/STAT3 signaling pathway.

In another specific embodiment, the comparison is made between the expression of each of the genes in the sample and the expression of the same genes in a pool representing only one of two or more phenotypes. In the context of IL-6/STAT3 signaling pathway status-correlated genes, for example, one can compare the expression levels of IL-6/STAT3 signaling pathway regulation status-related genes in a sample to the average level of the expression of the same genes in a "deregulated" pool of samples (as opposed to a pool of samples that include samples from patients having regulated and deregulated IL-6/STAT3 signaling pathway status). Thus, in this method, a sample is classified as having a deregulated IL-6/STAT3 signaling pathway status if the level of expression of prognosis-correlated genes exceeds a chosen coefficient of correlation to the average "deregulated IL-6/STAT3 signaling pathway" expression profile (i.e., the level of expression of IL-6/STAT3 signaling pathway status-correlated genes in a pool of samples from patients having a "deregulated IL-6/STAT3 signaling pathway status." Patients or subjects whose expression levels correlate more poorly with the "deregulated IL-6/STAT3 signaling pathway" expression profile (i.e., whose correlation coefficient fails to exceed the chosen coefficient) are classified as having a regulated IL-6/STAT3 signaling pathway status.

Of course, single-channel data may also be used without specific comparison to a mathematical sample pool. For example, a sample may be classified as having a first or a second phenotype, wherein the first and second phenotypes are related, by calculating the similarity between the expression of at least 5 markers in the sample, where the markers are correlated with the first or second phenotype, to the expression of the same markers in a first phenotype template and a second phenotype template, by (a) labeling nucleic acids derived from a sample with a fluorophore to obtain a pool of fluorophore-labeled nucleic acids; (b) contacting said fluorophore-labeled nucleic acid with a microarray under conditions such that hybridization can occur, detecting at each of a plurality of discrete loci on the microarray a fluorescent emission signal from said fluorophore-labeled nucleic acid that is bound to said microarray under said conditions; and (c) determining the similarity of marker gene expression in the individual sample to the first and second templates, wherein if said expression is more similar to the first template, the sample is classified as having the first phenotype, and if said expression is more similar to the second template, the sample is classified as having the second phenotype.

Methods for Classification of Expression Profiles

In preferred embodiments, the methods of the invention use a classifier for predicting IL-6/STAT3 signaling pathway regulation status of a sample, predicting response to agents that modulate the IL-6/STAT3 signaling pathway, assigning treatment to a subject, and/or measuring pharmacodynamic effect of an agent. The classifier can be based on any appropriate pattern recognition method that receives an input comprising a biomarker profile and provides an output comprising data indicating which patient subset the patient belongs. The classifier can be trained with training data from a training population of subjects. Typically, the training data comprise for each of the subjects in the training population a training marker profile comprising measurements of respective gene products of a plurality of genes in a suitable sample taken from the patient and outcome information, i.e., deregulated or regulated IL-6/STAT3 signaling pathway status.

In preferred embodiments, the classifier can be based on a classification (pattern recognition) method described below, e.g., profile similarity; artificial neural network; support vector machine (SVM); logic regression, linear or quadratic discriminant analysis, decision trees, clustering, principal component analysis, nearest neighbor classifier analysis, nearest shrunken centroid, random forest. Such classifiers can be trained with the training population using methods described in the relevant sections, infra.

The biomarker profile can be obtained by measuring the plurality of gene products in a cell sample from the subject using a method known in the art, e.g., a method described infra.

Various known statistical pattern recognition methods can be used in conjunction with the present invention. A classifier based on any of such methods can be constructed using the biomarker profiles and IL-6/STAT3 pathway signaling status data of training patients. Such a classifier can then be used to evaluate the IL-6/STAT3 pathway signaling status of a patient based on the patient's biomarker profile. The methods can also be used to identify biomarkers that discriminate between different IL-6/STAT3 signaling pathway regulation status using a biomarker profile and IL-6/STAT3 signaling pathway regulation data of training patients.

Profile Matching

A subject can be classified by comparing a biomarker profile obtained in a suitable sample from the subject with a biomarker profile that is representative of a particular phenotypic state. Such a marker profile is also termed a "template profile" or a "template." The degree of similarity to such a template profile provides an evaluation of the subject's phenotype. If the degree of similarity of the subject marker profile and a template profile is above a predetermined threshold, the subject is assigned the classification represented by the template. For example, a subject's outcome prediction can be evaluated by comparing a biomarker profile of the subject to a predetermined template profile corresponding to a given phenotype or outcome, e.g., a IL-6/STAT3 signaling pathway template comprising measurements of the plurality of biomarkers which are representative of levels of the biomarkers in a plurality of subjects that have tumors with deregulated IL-6/STAT3 signaling pathway status.

In one embodiment, the similarity is represented by a correlation coefficient between the subject's profile and the template. In one embodiment, a correlation coefficient above a correlation threshold indicates a high similarity, whereas a correlation coefficient below the threshold indicates a low similarity.

Artificial Neural Network

In some embodiments, a neural network is used. A neural network can be constructed for a selected set of molecular markers of the invention. A neural network is a two-stage regression or classification model. A neural network has a layered structure that includes a layer of input units (and the bias) connected by a layer of weights to a layer of output units. For regression, the layer of output units typically includes just one output unit. However, neural networks can handle multiple quantitative responses in a seamless fashion. In multilayer neural networks, there are input units (input layer), hidden units (hidden layer), and output units (output layer). There is, furthermore, a single bias unit that is connected to each unit other than the input units. Neural networks are described in Duda et al., 2001, Pattern Classification, Second Edition, John Wiley & Sons, Inc., New York; and Hastie et al., 2001, The Elements of Statistical Learning, Springer-Verlag, New York.

Support Vector Machine

In some embodiments of the present invention, support vector machines (SVMs) are used to classify subjects using expression profiles of marker genes described in the present invention. General description of SVM can be found in, for example, Cristianini and Shawe-Taylor, 2000, An Introduction to Support Vector Machines, Cambridge University Press, Cambridge, Baser et al., 1992, "A training algorithm for optimal margin classifiers, in Proceedings of the 5th Annual ACM Workshop on Computational Learning Theory, ACM Press, Pittsburgh, Pa., pp. 142-152; Vapnik, 1998, Statistical Learning Theory, Wiley, New York; Duda, Pattern Classification, Second Edition, 2001, John Wiley & Sons, Inc.; Hastie, 2001, The Elements of Statistical Learning, Springer, N.Y.; and Furey et al, 2000, Bioinformatics 16, 906-914. Applications of SVM in biological applications are described in Jaakkola et al., Proceedings of the 7th International Conference on Intelligent Systems for Molecular Biology, AAAI Press, Menlo Park, Calif. (1999); Brown et al., Proc. Natl. Acad. Sci. 97(1):262-67 (2000); Zien et al., Bioinformatics, 16(9):799-807 (2000); Furey et al., Bioinformatics, 16(10):906-914 (2000).

In some embodiments, the classifier is based on a regression model, preferably a logistic regression model. Such a regression model includes a coefficient for each of the molecular markers in a selected set of molecular biomarkers of the invention. In such embodiments, the coefficients for the regression model are computed using, for example, a maximum likelihood approach. In particular embodiments, molecular biomarker data from two different classification or phenotype groups, e.g., deregulated or regulated IL-6/STAT3 signaling pathway, response or non-response to treatment to an agent that modulates the IL-6/STAT3 signaling pathway, is used and the dependent variable is the phenotypic status of the patient for which molecular marker characteristic data are from.

Some embodiments of the present invention provide generalizations of the logistic regression model that handle multicategory (polychotomous) responses. Such embodiments can be used to discriminate an organism into one or three or more classification groups, e.g., good, intermediate, and poor therapeutic response to treatment with IL-6/STAT3 signaling pathway agents. Such regression models use multicategory logic models that simultaneously refer to all pairs of categories, and describe the odds of response in one category instead of another. Once the model specifies logits for a certain (J-1) pairs of categories, the rest are redundant. See, for example, Agresti, An Introduction to Categorical Data Analysis, John Wiley & Sons, Inc., 1996, New York, Chapter 8, which is hereby incorporated by reference.

Discriminant Analysis

Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, the expression values for the selected set of molecular markers of the invention across a subset of the training population serve as the requisite continuous independent variables. The clinical group classification of each of the members of the training population serves as the dichotomous categorical dependent variable.

LDA seeks the linear combination of variables that maximizes the ratio of between-group variance and within-group variance by using the grouping information. Implicitly, the linear weights used by LDA depend on how the expression of a molecular biomarker across the training set separates in the two groups (e.g., a group that has deregulated IL-6/STAT3 signaling pathway and a group that have regulated IL-6/STAT3 signaling pathway status) and how this gene expression correlates with the expression of other genes. In some embodiments, LDA is applied to the data matrix of the N members in the training sample by K genes in a combination of genes described in the present invention. Then, the linear discriminant of each member of the training population is plotted. Ideally, those members of the training population representing a first subgroup (e.g. those subjects that have deregulated IL-6/STAT3 signaling pathway status) will cluster into one range of linear discriminant values (e.g., negative) and those member of the training population representing a second subgroup (e.g. those subjects that have regulated IL-6/STAT3 signaling pathway status) will cluster into a second range of linear discriminant values (e.g., positive). The LDA is considered more successful when the separation between the clusters of discriminant values is larger. For more information on linear discriminant analysis, see Duda, Pattern Classification, Second Edition, 2001, John Wiley & Sons, Inc; and Hastie, 2001, The Elements of Statistical Learning, Springer, N.Y.; Venables & Ripley, 1997, Modern Applied Statistics with s-plus, Springer, N.Y. Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

Decision Trees

In some embodiments of the present invention, decision trees are used to classify subjects using expression data for a selected set of molecular biomarkers of the invention. Decision tree algorithms belong to the class of supervised learning algorithms. The aim of a decision tree is to induce a classifier (a tree) from real-world example data. This tree can be used to classify unseen examples which have not been used to derive the decision tree.

A decision tree is derived from training data. An example contains values for the different attributes and what class the example belongs. In one embodiment, the training data is expression data for a combination of genes described in the present invention across the training population.

Clustering

In some embodiments, the expression values for a selected set of molecular markers of the invention are used to cluster a training set. For example, consider the case in which ten gene biomarkers described in one of the genes of the present invention are used. Each member m of the training population will have expression values for each of the ten biomarkers. Such values from a member m in the training population define the vector: Those members of the training population that exhibit similar expression patterns across the training group will tend to cluster together. A particular combination of genes of the present invention is considered to be a good classifier in this aspect of the invention when the vectors cluster into the trait groups found in the training population. For instance, if the training population includes patients with good or poor prognosis, a clustering classifier will cluster the population into two groups, with each group uniquely representing either a deregulated IL-6/STAT3 signalling pathway status or a regulated IL-6/STAT3 signalling pathway status.

Clustering is described on pages 211-256 of Duda and Hart, Pattern Classification and Scene Analysis, 1973, John Wiley & Sons, Inc., New York. As described in Section 6.7 of Duda, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda, clustering does not require the use of a distance metric. For example, a nonmetric similarity function $s(x, x')$ can be used to compare two vectors x and x'. Conventionally, $s(x, x')$ is a symmetric function whose value is large when x and x' are somehow "similar". An example of a nonmetric similarity function $s(x, x')$ is provided on page 216 of Duda.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda. Criterion functions are discussed in Section 6.8 of Duda. More recently, Duda et al., Pattern Classification, 2nd edition, John Wiley & Sons, Inc. New York, has been published. Pages 537-563 describe clustering in detail. More information on clustering techniques can be found in Kaufman and Rousseeuw, 1990, Finding Groups in Data: An Introduction to Cluster Analysis, Wiley, New York, N.Y.; Everitt, 1993, Cluster analysis (3d ed.), Wiley, New York, N.Y.; and Backer, 1995, Computer-Assisted Reasoning in Cluster Analysis, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Principal Component Analysis

Principal component analysis (PCA) has been proposed to analyze gene expression data. Principal component analysis is a classical technique to reduce the dimensionality of a data set by transforming the data to a new set of variable (principal components) that summarize the features of the data. See, for example, Jolliffe, 1986, Principal Component Analysis, Springer, N.Y. Principal components (PCs) are uncorrelate and are ordered such that the kth PC has the kth largest variance among PCs. The kth PC can be interpreted as the direction that maximizes the variation of the projections of the data points such that it is orthogonal to the first k-1 PCs. The first few PCs capture most of the variation in the data set. In contrast, the last few PCs are often assumed to capture only the residual 'noise' in the data.

PCA can also be used to create a classifier in accordance with the present invention. In such an approach, vectors for a selected set of molecular biomarkers of the invention can be constructed in the same manner described for clustering above. In fact, the set of vectors, where each vector represents the expression values for the select genes from a particular member of the training population, can be considered a matrix. In some embodiments, this matrix is represented in a Free-Wilson method of qualitative binary description of monomers (Kubinyi, 1990, 3D QSAR in drug design theory methods and applications, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been accounted for.

Then, each of the vectors (where each vector represents a member of the training population) is plotted. Many different types of plots are possible. In some embodiments, a one-dimensional plot is made. In this one-dimensional plot, the value for the first principal component from each of the members of the training population is plotted. In this form of plot, the expectation is that members of a first group will cluster in one range of first principal component values and members of a second group will cluster in a second range of first principal component values.

In one example, the training population comprises two classification groups. The first principal component is computed using the molecular biomarker expression values for the select genes of the present invention across the entire training population data set where the classification outcomes are known. Then, each member of the training set is plotted as a function of the value for the first principal component. In this example, those members of the training population in which the first principal component is positive represent one classification outcome and those members of the training population in which the first principal component is negative represent the other classification outcome. In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent subjects in the first classification group, a second cluster of members in the two-dimensional plot will represent subjects in the second classification group, and so forth.

In some embodiments, the members of the training population are plotted against more than two principal components and a determination is made as to whether the members of the training population are clustering into groups that each uniquely represents a subgroup found in the training population. In some embodiments, principal component analysis is performed by using the R mva package (Anderson, 1973, Cluster Analysis for applications, Academic Press, New York 1973; Gordon, Classification, Second Edition, Chapman and Hall, CRC, 1999.). Principal component analysis is further described in Duda, Pattern Classification, Second Edition, 2001, John Wiley & Sons, Inc.

Nearest Neighbor Classifier Analysis

Nearest neighbor classifiers are memory-based and require no model to be fit. Given a query point x0, the k training points x(r), r, . . . , k closest in distance to x0 are identified and then the point x0 is classified using the k nearest neighbors. Ties can be broken at random. In some embodiments, Euclidean distance in feature space is used to determine distance as:

$d(i)$=-parallel-$x(i)$–$xo$·parallel.

Typically, when the nearest neighbor algorithm is used, the expression data used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. Profiles of a selected set of molecular biomarkers of the invention represents the feature space into which members of the test set are plotted. Next, the ability of the training set to correctly characterize the members of the test set is computed. In some embodiments, nearest neighbor computation is performed several times for a given combination of genes of the present invention. In each iteration of the computation, the members of the training population are randomly assigned to the training set and the test set. Then, the quality of the combination of genes is taken as the average of each such iteration of the nearest neighbor computation. The nearest neighbor rule can be refined to deal with issues of unequal class priors, differential misclassification costs, and feature selection. Many of these refinements involve some form of weighted voting for the neighbors. For more information on nearest neighbor analysis, see Duda, Pattern Classification, Second Edition, 2001, John Wiley & Sons, Inc; and Hastie, 2001, The Elements of Statistical Learning, Springer, N.Y.

Evolutionary Methods

Inspired by the process of biological evolution, evolutionary methods of classifier design employ a stochastic search for an optimal classifier. In broad overview, such methods create several classifiers—a population—from measurements of gene products of the present invention. Each classifier varies somewhat from the other. Next, the classifiers are scored on expression data across the training population. In keeping with the analogy with biological evolution, the resulting (scalar) score is sometimes called the fitness. The classifiers are ranked according to their score and the best classifiers are retained (some portion of the total population of classifiers). Again, in keeping with biological terminology, this is called survival of the fittest. The classifiers are stochastically altered in the next generation—the children or offspring. Some offspring classifiers will have higher scores than their parent in the previous generation, some will have lower scores. The overall process is then repeated for the subsequent generation: The classifiers are scored and the best ones are retained, randomly altered to give yet another generation, and so on. In part, because of the ranking, each generation has, on average, a slightly higher score than the previous one. The process is halted when the single best classifier in a generation has a score that exceeds a desired criterion value. More information on evolutionary methods is found in, for example, Duda, Pattern Classification, Second Edition, 2001, John Wiley & Sons, Inc.

Bagging, Boosting and the Random Subspace Method

Bagging, boosting and the random subspace method are combining techniques that can be used to improve weak classifiers. These techniques are designed for, and usually applied to, decision trees. In addition, Skurichina and Duin provide evidence to suggest that such techniques can also be useful in linear discriminant analysis.

In bagging, one samples the training set, generating random independent bootstrap replicates, constructs the classifier on each of these, and aggregates them by a simple majority vote in the final decision rule. See, for example, Breiman, 1996, Machine Learning 24, 123-140; and Efron & Tibshirani, An Introduction to Bootstrap, Chapman & Hall, New York, 1993.

In boosting, classifiers are constructed on weighted versions of the training set, which are dependent on previous classification results. Initially, all objects have equal weights, and the first classifier is constructed on this data set. Then, weights are changed according to the performance of the classifier. Erroneously classified objects (molecular biomarkers in the data set) get larger weights, and the next classifier is boosted on the reweighted training set. In this way, a sequence of training sets and classifiers is obtained, which is then combined by simple majority voting or by weighted majority voting in the final decision. See, for example, Freund & Schapire, "Experiments with a new boosting algorithm," Proceedings 13th International Conference on Machine Learning, 1996, 148-156.

In some embodiments, modifications of Freund and Schapire, 1997, Journal of Computer and System Sciences 55, pp. 119-139, are used. For example, in some embodiments, feature pre-selection is performed using a technique such as the nonparametric scoring methods of Park et al., 2002, Pac. Symp. Biocomput. 6, 52-63. Feature pre-selection is a form of dimensionality reduction in which the genes that discriminate between classifications the best are selected for use in the classifier. Then, the LogitBoost procedure introduced by Friedman et al., 2000, Ann Stat 28, 337-407 is used rather than the boosting procedure of Freund and Schapire. In some embodiments, the boosting and other classification methods of Ben-Dor et al., 2000, Journal of Computational Biology 7, 559-583 are used in the present invention. In some embodiments, the boosting and other classification methods of Freund and Schapire, 1997, Journal of Computer and System Sciences 55, 119-139, are used.

In the random subspace method, classifiers are constructed in random subspaces of the data feature space. These classifiers are usually combined by simple majority voting in the final decision rule. See, for example, Ho, "The Random subspace method for constructing decision forests," IEEE Trans Pattern Analysis and Machine Intelligence, 1998; 20(8): 832-844.

Random Forest

Random Forest classifiers are an ensemble classifier that consists of many decision trees and outputs the class that is the mode of the classes output by individual trees. Random Forests utilize bootstrapping instead of cross-validation. For each iteration, a random sample (with replacement) is drawn and the largest tree possible is grown. Each tree receives a vote in the final class prediction. To fit a random forest, the number of trees (e.g. bootstrap iterations) is specified. The random forest algorithm gauges biomarker importance by the average reduction in the training accuracy. The random forest method uses a number of different decision trees. A biomarker is considered to have discriminating significance if it served as a decision branch of a decision tree from a significant random forest analysis.

Random forest (or random forests) is an ensemble classifier that consists of many decision trees and outputs the class that is the mode of the classes output by individual trees. (Breiman, Leo (2001). "Random Forests". Machine Learning 45 (1): 5-32). Random forest is one of the most accurate learning algorithms available, i.e., produces a highly accurate classifier for data sets. (Caruana, Rich; Karampatziakis, Nikos; Yessenalina, Ainur (2008). "An empirical evaluation of supervised learning in high dimensions." Proceedings of the 25th International Conference on Machine Learning (ICML)). The method combines "bagging" and the random selection of features in order to construct a collection of decision trees with controlled variation. The selection of a random subset of features is an example of the random subspace method, which is a way to implement stochastic discrimination. Bootstrap distribution is used as a way to estimate the variation in a statistics based on the original data. For each tree grown on a bootstrap sample, e.g., 150 or 500, the error rate for observations left out of the bootstrap sample is monitored. This is called the "out-of-bag" error rate.

Each tree is constructed using the following algorithm: (1) Let the number of training cases be N, and the number of variables in the classifier be M; (2) The number m of input variables to be used to determine the decision at a node of the tree; m should be much less than M; (3) Choose a training set for this tree by choosing n times with replacement from all N available training cases (i.e., take a bootstrap sample), and use the rest of the cases to estimate the error of the tree, by predicting their classes; (4) For each node of the tree, randomly choose m variables on which to base the decision at that node. Calculate the best split based on these m variables in the training set; and (5) Each tree is fully grown and not pruned (as may be done in constructing a normal tree classifier).

For prediction a new sample is pushed down the tree. It is assigned the label of the training sample in the terminal node it ends up in. This procedure is iterated over all trees in the ensemble, and the mode vote of all trees is reported as random forest prediction.

In one embodiment, random forest analysis involving classification and regression based on a forest of trees using random inputs is performed using "randomForest: Breiman and Cutler's random forests for classification and regression" (Depends: R (>=2.5.0), stats) (Version: 4.6-6) (2012-01-06) (Fortran original by Leo Breiman and Adele Cutler, R port by Andy Liaw and Matthew Wiener). See, A. Liaw and M. Wiener (2002). Classification and Regression by randomForest. R News 2(3), 18-22.

Random Forests are further described in Liaw and Wiener, R News Vol. 2/3, December 2002, pgs. 18-22; Dfaz-Uriarte and Alvarez, BMC Bioinformatics. 2006 Jan. 6; 7:3); Statnikov et al., BMC Bioinformatics. 2008 Jul. 22; 9:319; Shi et al., Mod Pathol. 2005 April; 18(4):547-57, Breiman, 1999, "Random Forests—Random Features," Technical Report 567, Statistics Department, U.C. Berkeley, September 1999, which is hereby incorporated by reference in its entirety, each of which is incorporated by reference herein it its entirety.

Other Algorithms

The pattern classification and statistical techniques described above are merely examples of the types of models that can be used to construct a model for classification. Moreover, combinations of the techniques described above can be used. Some combinations, such as the use of the combination of decision trees and boosting, have been described. However, many other combinations are possible. In addition, in other techniques in the art such as Projection Pursuit and Weighted Voting can be used to construct a classifier.

As discussed in the Experimental Section, expression of the subject biomarker genes is preferably determined after real-time PCR using SYBR Green, and a $\Delta\Delta CT$ method employed to analysis the data. The average CT values of house keeping genes in each sample is calculated as house keeping gene CT value for that sample. $\Delta CT$ was calculated by subtracting house keeping CT value from individual assay CT value of same sample. $\Delta\Delta CT$ value was derived by further subtracting $\Delta CT$ value of control samples of each assay from its corresponding $\Delta CT$ value of treatment sample. A Random Forest method is preferably used to analyze the $\Delta\Delta CT$ values of the samples and the expression thereof used to assess the regulatory status of the IL-6/STAT3 pathway activity in the sample.

Experimental Methods Used to Identify Inventive IL-6/STAT3 Signaling (16) Gene Signature Identification of IL-6/STAT3 Response Genes by Gene Expression Profiling The protocol that was used to identify the subject gene signature is depicted schematically in FIG. 1. As depicted therein, human liver hepatocellular cells HepG2 and human normal mammary epithelial cells MCF10A were plated in 6-well plate in a density of $4\times10^5$ cells per well for HepG2 and $2.5\times10^5$ cells per well for MCF10A in 2 ml growth medium and were reverse transfected with siRNA specifically targeting STAT3 or non targeting siRNA as control at the time of plating cells. For each well, 6 ul of SureFECT transfection reagent (SABiosciences, a QIAGEN company) was diluted into 400 µl of OptiMEM medium (Invitrogen). The diluted transfection reagent was mixed with 40 nM STAT3 targeting siRNA duplex 7 (QIAGEN) or non-targeting AllStars siRNA (QIAGEN) as control. After incubation at room temperature for 20 min, the transfection mixture was added into 6-well plate and covered with 2 ml growth medium with HepG2 or MCF10A cells. Plated cells were incubated in a cell culture incubator at 37 degrees C. with 5% CO2 supplied. Forty-eight hours after transfection, the medium with transfection mixture was replaced with 1 ml serum-free medium in each well and cells were incubated for 16 hours in serum-free medium. After 16 hours serum starvation, 1 ml serum-free medium with either 60 ng/ml recombinant IL-6 (R&D Systems) or PBS as control was added on top of 1 ml cells bringing the final serum-free medium volume to 2 ml and IL-6 concentration to 30 ng/ml.

At the end of the 8 hour IL-6 treatment cells were lysed in 200 ul of RLT Plus buffer (QIAGEN) for each well. The lysates were further processed to RNA isolation with RNeasy Plus RNA Isolation Kit from QIAGEN according to manufacturer's protocol. (See Appendix attached to this patent application) as described in experimental protocol section. At the end of isolation, 30 ul of RNase-free water was added to spin column to elute RNA off column. The concentration of RNA was measured with Nanodrop spectrophotometer (Thermo SCIENTIFIC) and the RNA was further processed for real-time RT-PCR or microarray gene expression profiling analysis.

Real-time RT-PCR was employed to confirm the effect of IL-6 treatment and STAT3 siRNA knockdown by measuring mRNA expression levels of IL-6/STAT3 target genes and STAT3 itself respectively. 1 μg of total RNA was reverse transcribed with RT2 First Strand cDNA synthesis kit (QIAGEN) according to protocol described in common experimental protocol section. The 20 μl cDNA reaction was diluted to 100 μl of water for real-time PCR analysis. For each real-time PCR reaction mixture, 1 μl of cDNA was mixed with 10 μM of 10 μM primer mixture (forward and reverse primers mixed), 12.5 μl of real-time PCR master mixture (QIAGEN) and 10.5 ul water to a total volume of 25 μl. The primer sequences used for SOCS3, JUNB, BCL3, ZFP36, CEBPD, PIM1 are in the Table below:

The amplification and labeling reagents and reaction parameters for HepG2 and MCF10A cell samples are shown below.

HepG2 Cells

| 1-strand cDNA synthesis sample | RNA con ng/ul | RNA amount 300 ng | H2O | T7-Oligo(dT) primer | total |
|---|---|---|---|---|---|
| HepG2/nc/+IL-6/1 | 1287.45 | 0.23 | 1.77 | 1 | 3.00 |
| HepG2/nc/+IL-6/2 | 1028.62 | 0.29 | 1.71 | 1 | 3.00 |
| HepG2/nc/+IL-6/3 | 771.28 | 0.39 | 1.61 | 1 | 3.00 |
| HepG2/nc/−IL-6/1 | 964.86 | 0.31 | 1.69 | 1 | 3.00 |
| HepG2/nc/−IL-6/2 | 547.48 | 0.55 | 1.45 | 1 | 3.00 |
| HepG2/nc/−IL-6/3 | 692.68 | 0.43 | 1.57 | 1 | 3.00 |
| HepG2/Stat3/+IL-6/1 | 975.75 | 0.31 | 1.69 | 1 | 3.00 |
| HepG2/Stat3/+IL-6/2 | 1026.54 | 0.29 | 1.71 | 1 | 3.00 |
| HepG2/Stat3/+IL-6/3 | 1072.54 | 0.28 | 1.72 | 1 | 3.00 |
| HepG2/Stat3/−IL-6/1 | 814.68 | 0.37 | 1.63 | 1 | 3.00 |
| HepG2/Stat3/−IL-6/2 | 616.46 | 0.49 | 1.51 | 1 | 3.00 |
| HepG2/Stat3/−IL-6/3 | 636.18 | 0.47 | 1.53 | 1 | 3.00 | incubate 65 degrees C. for 5 min, chill on ice 1 min, centrifuge briefly

| Gene Symbol | Refseq | Forward Primer | Reverse Primer |
|---|---|---|---|
| SOCS3 | NM_003955 | CCA CCT ACT GAA CCC TCC TCC (SEQ ID NO: 171) | TCT TCC GAC AGA GAT GCT GAA (SEQ ID NO: 172) |
| JUNB | NM_002229 | CGA CTA CAA ACT CCT GAA ACC G (SEQ ID NO: 173) | GAA GAG GCG AGC TTG AGA GAC (SEQ ID NO: 174) |
| BCL3 | NM_005178 | CAC TCT CTA CCA GAT AAC TGA GGA G (SEQ ID NO: 175) | TAA TAA TTT ACA TCG TGA TCC GTG C (SEQ ID NO: 176) |
| CEBPD | NM_005195 | CGC CAT GTA CGA CGA CGA G (SEQ ID NO: 17) | CGC CTT GTG ATT GCT GTT G (SEQ ID NO: 18) |
| ZFP36 | NM_003407 | GCT ATG TCG GAC CTT CTC AG (SEQ ID NO: 193) | CTT CGC TAG GGT TGT GGA TG (SEQ ID NO: 194) |
| PIM1 | NM_002648 | GAT CCG CTA CCA TCG CTC C (SEQ ID NO: 195) | ATC TCC ACA CAC CAT ATC ATA CAG (SEQ ID NO: 196) |

The reaction mixture was added into 384-well real-time PCR plate in duplicate wells with 10 μl each well. The PCR plate was sealed with optical adhesive film (Applied Biosystems) and centrifuged for 2 minutes at 2000 rpm. The real-time PCR was run in ABI 7900 real-time PCR machine (Applied Biosystems) with PCR program as following, 95 degrees C. for 10 min, 40 cycles of 95 degrees C. 15 seconds and 60 degrees C. 1 minutes following melting curve analysis. The effect of IL-6 treatment was confirmed by upregulation of IL-6/STAT3 target genes such as SOCS3, JUNB and CEBPD in IL-6 treated samples compared to untreated samples (See FIG. 2B). The siRNA knockdown of STAT3 was verified by decreased mRNA expression levels of STAT3 (See FIG. 2A).

After the confirmation of IL-6 treatment and STAT3 siRNA knockdown, RNA samples were processed to whole genome microarray gene profiling analysis. The 12 samples were split into four treatment groups in triplicates, sinon-no IL-6, sinon-IL-6, siSTAT3-no IL-6 and siSTAT3-IL-6. 300 ng of total RNA was amplified and labeled with TargetAmp Nano-g Biotin-aRNA Labeling Kit (Epicentre Biotechnologies) according to manufacturer's protocol.

| 1st strand cDNA synthesis master mix | 14 | |
|---|---|---|
| 1st strand cDNA premix | 21 | |
| DTT | 3.5 | |
| superscript III (200 u/ul) | 3.5 | |
| Total | 28 | gently mix | add 2 ul to each reaction, gently mix, incubate 50 degrees C. for 30 min.

Second Strand cDNA Synthesis

| second strand cDNA synthesis master mix | 13 | |
|---|---|---|
| 2nd-strand cDNA premix | 58.5 | |
| 2nd-strand DNA polymerase | 6.5 | |
| total | 65 | gently mix | add 5 ul to each reaction, gently mix, incubate 65 degrees C. 10 min, centrifuge briefly.

incubate at 80 degrees C. for 3 min, centrifuge briefly, chill on ice.

In Vitro Transcription of Biotin-aRNA warm T7 RNA polymerase to RT and thaw other reagent at RT

| in vitro transcription master mix setup at RT | 13 | |
|---|---|---|
| T7 transcription buffer | 26 | |
| UTP/biotin-UTP | 39 | |
| NTP premix | 130 | |
| DTT | 39 | |
| T7 RNA polymerase | 26 | |
| Total | 260 | gently mix | add 20 ul to each reaction, gently mix, incubate 42 degrees C. for 4 h (don't exceed 4h)
add 2 ul Rnase-free Dnase I to each reaction, mix gently, incubate 37 degrees C. 15 min.
Biotin-aRNA Purification (SABio cRNA Cleanup Kit)
Bind aRNA to Spin Column
a. transfer entire reaction (32 ul) to 1.5 ml tube
b. add 112 ul lysis & binding buffer (G6) to each reaction, mix by pipetting 2-3×
c. add 112 ul RT 100% ETOH, mix by pipettting 5-6×
d. immediately load on spin column
e. centrifuge 8000 g for 30 sec
f. discard flow-through, put column back to collection
Washing Spin Column
a. add 400-500 ul washing buffer (G17+ETOH) to each spin column
b. centrifuge 8000 g 30 sec
c. discard flow-through, put column back to collection tube
d. add 200 ul washing buffer (G17+ETOH) to each spin column
e. centrifuge 11000 g 1 min
f. discard flow-through, put column back to collection tube
g. centrifuge 11000 g 2 min (180 degree rotate from previous orientation)
Elute aRNA from Spin Column
a. transfer spin column to new elution tube
b. add 40 ul (<40 ug, 80 ul if >40 ug) H2O into column
c. sit in RT 2 min
d. centrifuge 8000 g for 1 min
e. store aRNA −80 degrees C.
MCF10A Cells

| 1-strand cDNA synthesis sample | RNA con ng/ul | RNA amount 300 ng | H2O | T7-Oligo(dT) primer | Total |
|---|---|---|---|---|---|
| MCF10A/nc/+IL-6/1 | 839.39 | 0.36 | 1.64 | 1 | 3.00 |
| MCF10A/nc/+IL-6/2 | 984.02 | 0.30 | 1.70 | 1 | 3.00 |
| MCF10A/nc/+IL-6/3 | 875.17 | 0.34 | 1.66 | 1 | 3.00 |
| MCF10A/nc/−IL-6/1 | 798.19 | 0.38 | 1.62 | 1 | 3.00 |
| MCF10A/nc/−IL-6/2 | 626.77 | 0.48 | 1.52 | 1 | 3.00 |
| MCF10A/nc/−IL-6/3 | 445.07 | 0.67 | 1.33 | 1 | 3.00 |
| MCF10A/Stat3/+IL-6/1 | 760.52 | 0.39 | 1.61 | 1 | 3.00 |
| MCF10A/Stat3/+IL-6/2 | 735.99 | 0.41 | 1.59 | 1 | 3.00 |
| MCF10A/Stat3/+IL-6/3 | 748.25 | 0.40 | 1.60 | 1 | 3.00 |
| MCF10A/Stat3/−IL-6/1 | 629.8 | 0.48 | 1.52 | 1 | 3.00 |
| MCF10A/Stat3/−IL-6/2 | 406.17 | 0.74 | 1.26 | 1 | 3.00 |
| MCF10A/Stat3/−IL-6/3 | 517.99 | 0.58 | 1.42 | 1 | 3.00 | incubate 65 degree C. for 5 min, chill on ice 1 min, centrifuge briefly

| 1st strand cDNA synthesis master mix | 14 | |
|---|---|---|
| 1st strand cDNA premix | 21 | |
| DTT | 3.5 | |
| superscript III (200 u/ul) | 3.5 | |
| Total | 28 | gently mix | add 2 ul to each reaction, gently mix, incubate 50 degrees C. for 30 min.
Second Strand cDNA Synthesis

| second strand cDNA synthesis master mix | 13 | |
|---|---|---|
| 2nd-strand cDNA premix | 58.5 | |
| 2nd-strand DNA polymerase | 6.5 | |
| total | 65 | gently mix | add 5 ul to each reaction, gently mix, incubate 65 degrees C. 10 min, centrifuge briefly.
incubate at 80 degrees C. for 3 min, centrifuge briefly, chill on ice.
In Vitro Transcription of Biotin-sRNA
warm T7 RNA polymerase to RT and thaw other reagent at RT

| in vitro transcription master mix setup at RT | 13 | |
|---|---|---|
| T7 transcription buffer | 26 | |
| UTP/biotin-UTP | 39 | |
| NTP premix | 130 | |
| DTT | 39 | |
| T7 RNA polymerase | 26 | |
| Total | 260 | gently mix | add 20 ul to each reaction, gently mix, incubate 42 degrees C. for 4 h (don't exceed 4h)
add 2 ul Rnase-free Dnase I to each reaction, mix gently, incubate 37 degrees C. 15 min.
Biotin-aRNA Purification (SABio cRNA Cleanup Kit)
Bind aRNA to Spin Column
a. transfer entire reaction (32 ul) to 1.5 ml tube
b. add 112 ul lysis & binding buffer (G6) to each reaction, mix by pipetting 2-3×
c. add 112 ul RT 100% ETOH, mix by pipettting 5-6×
d. immediately load on spin column
e. centrifuge 8000 g for 30 sec
f. discard flow-through, put column back to collection
Washing Spin Column
a. add 400-500 ul washing buffer (G17+ETOH) to each spin column
b. centrifuge 8000 g 30 sec
c. discard flow-through, put column back to collection tube
d. add 200 ul washing buffer (G17+ETOH) to each spin column
e. centrifuge 11000 g 1 min
f. discard flow-through, put column back to collection tube
g. centrifuge 11000 g 2 min (180 degree rotate from previous orientation)
Elute aRNA from Spin Column
a. transfer spin column to new elution tube
b. add 40 ul (<40 ug, 80 ul if >40 ug) H2O into column
c. sit in RT 2 min
d. centrifuge 8000 g for 1 min
e. store aRNA −80 degrees C.

The concentration of labeled antisense RNA was measured with Nanodrop spectrophotometer (Thermo SCIENTIFIC). Total 750 ng of labeled antisense RNA was hybridized onto an Illumina Human HT-12 BeadChip (Illumina) according to the manufacturer's standard protocol for 12 samples chip (Illumina Whole Genome Gene Expression Direct Hybridization Assay).

Hybridized BeadChip was washed and scanned on an iScan (Illumina) according to manufacturer's standard protocol. The image file was processed with GenomeStudio software (Illumina) without background correction and normalization. The sample probe expression file was exported as GeneSpring format for further analysis with GeneSpring software (Agilent). The expression data was analyzed with GeneSpring with its guided workflow and fold changes and statistical analysis was computed between groups during the guided workflow analysis.

After effecting these protocols, three gene lists were selected from the identified IL-6 response genes as IL-6/STAT3 response genes. Two gene lists (HepG2 list 1 and HepG2 list 2) were derived from HepG2 cell with different selection criteria. HepG2 list 1 had 57 genes (66 probes) and was selected based on sinon-IL-6 vs sinon-no IL-6 adjusted P<=0.05, fold>=1.5 and sinon-IL-6 vs siSTAT3-IL-6 P<=0.05 (See FIG. 3A). HepG2 list 2 had 52 genes (55 probes) and was selected based on sinon-IL-6 vs sinon adjusted P<=0.05, and sinon-IL-6 vs siSTAT3-IL-6 adjusted P<=0.05 (see FIG. 3B). 14 genes were derived from MCF10A samples and were selected based on sinon-IL-6 vs sinon-no IL-6 P<=0.05, fold>=1.5, and sinon-IL-6 vs siSTAT3-IL-6 P<=0.05. All three gene lists showed similar pattern of expression changes across treatment conditions. Expression changes of those genes were statistically significant in response to IL-6 and were reversed upon treatment with STAT3 siRNA. A list of 84 genes from all three gene lists combined were selected as IL-6/STAT3 response genes from microarray studies. These 84 genes plus 4 well known IL-6/STAT3 target genes and 8 house keeping genes were converted to real-time PCR platform for further verification.

Identification of IL-6/STAT3 Gene Expression Signature

To test these 88 IL-6/STAT3 response genes with real-time PCR, SYBR green based real-time PCR assay was designed for each individual gene. The sequence information for all primers is contained in FIG. 6.

Sixteen samples were employed to test the expression of these 88 genes. The IL-6/STAT3 pathway activity was negatively regulated in seven samples with STAT3 siRNA treatment. In contrast, nine samples had their IL-6/STAT3 pathway activity positively regulated and they were stimulated with IL-6 to activate IL-6/STAT3 pathway activity.

The STAT3 siRNA was reverse transfected into HepG2, 293H, Hela, A549, U105MG, HT1080 and MDA-MB-231 cells. For each well of 6-well plate, 6 µl of SureI-ECT transfection reagent (SABiosciences, a QIAGEN Company) was diluted into 200 µl of OptiMEM medium (Invitrogen). The diluted transfection reagent was mixed with 40 nM STAT3 targeting siRNA duplex 7, or non-targeting siRNA (QIAGEN) as control. Master transfection mixture for 4 wells was prepared for either STAT3 or non-target siRNA. After incubation at room temperature for 20 minutes, 200 µl of transfection mixture was added into each well in eight 6-well plates with one plate for each cell line including HepG2, 293H, Hela, A549, U105MG, HT1080 and MDA-MB-231. Each plate had two wells containing STAT3 siRNA mixture and two wells containing non-target siRNA mixture. These two duplicate wells were for protein extraction and RNA isolation respectively. During the 20 minute incubation time, different cell lines were trypsinized, washed off plate and resuspended in 8 ml culture medium and cell numbers were counted with a hemocytometer.

Cells were diluted into culture medium in a concentration of $1-2 \times 10^5$ cells per ml. For each well, 2 ml of cells ($2-4 \times 10^5$) were plated in 6-well plate on top of 200 µl transfection mixture and the plate was mixed well. The cell culture plates were put back into incubator and incubated for 72 hours at 37 degrees C. with 5% CO2 supplied. At the end of 72 hours incubation, cells were either lysed in 50 µl modified RIPA buffer for protein lysate extraction or in 200 µl lysis RLT Plus buffer for RNA isolation. The protein extraction and western blot was carried out according to western blot protocol in common experimental protocol section with rabbit anti-pSTAT3 (1:1000) and rabbit anti-STAT3 (1:1000) antibody. The decreased STAT3 protein levels in both phosphorylated and total forms verified the effect of STAT3 siRNA (See FIG. 4B). The RNA was isolated with RNeasey Plus RNA Isolation Kit from QIAGEN according to manufacturer's protocol as described in experimental protocol section.

To obtain nine positively regulated samples with IL-6 treatment, nine different cell lines were plated in 6-well plates in a density of $2-4 \times 10^5$ cells/well/2 ml. After 24 h of plating, cells were switched to serum-free medium by removing normal culture medium, washing cells in PBS two times and replacing with 1 ml serum-free medium each well. After 16 hours in serum-free medium, cells were replaced with serum-free medium with or without 30 ng/ml IL-6 in duplicate wells for an additional incubation of 8 h. At the end of 8 hours incubation, cells were either lysed in 50 µl modified RIPA buffer for protein lysate extraction or in 200 µl RLT Plus lysis buffer for RNA isolation. The protein extraction and western blot was carried out according to western blot protocol with rabbit anti-pSTAT3 (1:1000) and rabbit anti-STAT3 (1:1000) antibody. The increased pSTAT3 protein levels confirmed the effect of IL-6 (See FIG. 4A). The RNA was isolated with RNease Phis RNA Isolation Kit from QIAGEN according to manufacturer's protocol described in experimental protocol section.

To verify 84 IL-6/STAT3 response genes with SYBR green based real-time PCR on the described seven negative and nine positive samples, 1 µg of total RNA was reversed transcribed with RT2 First Strand cDNA synthesis kit (SABiosciences, a QIAGEN company) according to manufacturer's protocol in experimental protocol section. The 20 µl of reverse transcription reaction was diluted to 200 µl with water. For each real-time PCR reaction, 1 µl of diluted cDNA was mixed with 5 µl of SYBR green PCR master mixture and 4 µl of water to give a final volume of 10 µl of each reaction. A master mixture of 110 real-time PCR reactions was prepared for each sample and added into 384-well plate with 10 µl for each well. Each sample had 96 reactions in 96 wells corresponding to 96 different PCR assays (88 IL-6/STAT3 response genes plus 8 house keeping genes) and each 384-well plate was loaded with reactions for 4 samples (96×4 wells). The 384-well plates were run in ABI 7900 real-time PCR machine (Applied Biosystems) with SYBR green based real-time PCR program as following, 95 degrees C. for 10 min, 40 cycles of 95 degrees C. 15 seconds and 60 degrees C. 1 minutes following by melting curve analysis.

After real-time PCR, a ΔΔCT statistical analysis method was employed to analysis the data. The average CT values of 8 house keeping genes in each sample were calculated as house keeping gene CT value for that sample. OCT was calculated by subtracting house keeping CT value from individual assay CT value of same sample. The ΔΔCT value was derived by further subtracting ΔCT value of control samples of each assay from its corresponding ΔCT value of treatment sample.

A Random Forest classifier method was used to analyze the ΔΔCT values of seven negative and nine positive samples. Up to 150 bootstrap samples containing 14 out of the 16 training samples were selected and the bootstrap was performed without replacement and stratified by class (selected 7 stimulated and 7 repressed). For each bootstrap, a random forest classifier (using default parameters) was trained on the 14 samples with all 88 gene expression measurements. Based on the random forest variable importance measure (mean decrease in out-of-bag classifier accuracy when a gene's expression values are randomly permuted), the top 16 ranked genes were selected from each bootstrap process. Each 150 bootstrap iteration generated a slightly differently ranked gene list and the average rank across the 150 bootstrap iterations for each gene was calculated. Genes were ranked by this average rank, and the top 16 genes were select as the final signature gene set. These sixteen genes were defined as a gene expression signature that differentially classified positive samples from negative samples (see FIG. 5A). These 16 genes and their Accession numbers are listed in the table below.

| Gene Symbol | RefSeq_ID |
|---|---|
| STAT3 | NM_213662 |
| SOCS3 | NM_003955 |
| IFITM2 | NM_006435 |
| CEBPD | NM_005195 |
| JUNB | NM_002229 |
| TUBB2A | NM_001069 |
| IL-6ST | NM_002184 |
| CASP4 | NM_001225 |
| PROS1 | NM_000313 |
| TNFRSF1A | NM_001065 |
| PVRL2 | NM_002856 |
| PHF21A | NM_016621 |
| BCL3 | NM_005178 |
| NRP1 | NM_003873 |
| GLRX | NM_002064 |
| TGM2 | NM_00461 |

The utility of the obtained 16 gene signature was verified on these 16 samples by cross validation with Random Forest classification method using described bootstrap process. During each of 150 bootstrap process, the top 16 genes were used to train a new random forest classifier and the model was used to score the two out-of-training samples. The performance of the classification method was estimated based on the ability of the model to classify two out-of-training samples during each bootstrap process. Using the described methods 14 out of 16 samples were clearly classified correctly based on this 16 gene signature (See FIG. 5B).

Standard Protocols for Common Experiments:
Cell Culture and Chemicals

All cell culture medium was purchased from Invitrogen and different cell lines were purchased from ATCC. 293H, HepG2, U373MG, U105MG, and MDA-MB-231 cells were cultured in DMEM medium with 10% FBS, 1 mM sodium pyruvate and non-essential amino acid (Invitrogen). CCD1079SK, BJ, IMR90, Hela, HT1082 and MCF7 cells were cultured in MEM medium with 10% FBS. Lncap and Raji cells were cultured in RPMI 1640 medium with 10% FBS. HT29 cells were cultured in McCoy's 5A modified medium with 10% FBS. All cells were cultured in a cell culture incubator at 37 degrees C. supplied with 5% CO2. All chemicals used in experiments were from Sigma unless indicated with other source.

Protocol for Cell Lysis and Western Blot

At the end of experimental treatment, cells were lysed in Modified RIPA buffer (150 mM NaCl, 50 mM TrisHCl, 1% IGEPAL, 0.5% sodium deoxycholate, 1 mM EDTA, 1% Triton X-100 and 0.1% SDS with protease and phosphatase inhibitor) (all chemicals from Sigma). For each well in 6-well plate, cell culture medium was aspirated and washed with 1 ml PBS. 50 μl of Modified RIPA buffer was added to each well and cells were scrapped off wells in Modified RIPA buffer. Cell lysate was transferred to 1.5 ml microcentrifuge tube and incubated on ice for 30 min. After 15 minutes centrifuge at 15000 rpm at 4 degrees C., supernatant was transferred to a new 1.5 ml tube and protein concentration was measured with BCA protein assay according to manufacturer's standard protocol (Pierce). The cell lysate was diluted in 30 μl of H2O to 2 μg/μl protein concentration and mixed with 30 μl of 2×SDS sample buffer (BioRAD) to give a final concentration of 1 μg/μl. The diluted lysate was heated at 70 degrees C. for 10 minutes to denature the protein. The lysate was centrifuged at 15000 rpm for 1 minutes after heating and was loaded on a precast 4-12% NuPAGE Novex Bis-Tris Mini gel (Invitrogen) with 15 μl lysate for each well. The gel was run at a constant voltage of 150 V for 1.5 hours following transfer to a nitrocellulose membrane at a constant voltage of 30 V for 2 hours according to manufacturer's protocol (Invitrogen). The nitrocellulose membrane was blocked in 5% milk in western blot wash buffer (1×PBS plus 0.1% Tween-20) for 1 hours at room temperature. Separate membranes were further incubated with rabbit anti-pSTAT3 (1:1000) (Cell Signaling), rabbit anti-STAT3 (1:1000) (Cell Signaling) and rabbit anti-GAPDH (1:2000) (Cell Signaling) primary antibodies at 40 C overnight. The next day, membranes were took out from 40 C and further incubated at room temperature for 30 minutes following three times of wash in western blot wash buffer with 5 minutes for each wash. Membranes were incubated with goat anti-rabbit (1:4000) secondary antibody (Cell Signaling) for 1 hours at room temperature. Membranes were washed in western blot wash buffer 5 minutes for three times. To detect protein band on membranes, mixed western blot substrate (0.75 ml peroxide solution mixed with 0.75 ml luminol enhancer solution) (Thermo SCIENTIFIC) was added to each membrane and incubated at room temperature for 1 minutes to cover the entire membrane. The membrane was exposed to Fuji image machine LAS-3000 (Fuji Film) for 2 minutes with chemiluminecence filter. The effect of IL-6 treatment was demonstrated by increased protein levels of pSTA3 in IL-6 treated samples compared to no treated samples. The effect of STAT3 siRNA was demonstrated by decreased protein levels of phorylated and total STAT3 in STAT3 siRNA transfected samples compared to non target siRNA transfected samples.

Total RNA Isolation with QIAGEN RNeasy Plus Mini Kit

To harvest cells grown in 6-well plate for RNA isolation, cell culture medium was removed and 200 μl of RNeasy Plus buffer was added into each well. Cells were scrapped off plate and lysate was transferred to a 1.5 ml microcentrifuge tube for immediate RNA isolation or stored at −80 degrees C. to isolate RNA later. To isolate RNA, transfer the homogenized lysate to a gDNA Eliminator spin column placed in a 2 ml collection tube. Centrifuge for 30 s at ≥8000×g (≥10,000 rpm). Discard the column, and save the flowthrough. One volume (200 μl) of 70% ethanol was added to the flowthrough and mixed 6 times by pipetting.

The mixed sample was added to an RNeasy spin column placed in a 2 ml collection tube and centrifuged for 1 minutes at ≥8000×g (≥10,000 rpm). The column was washed with 700 μl of buffer RW1 by centrifuging for 1 minutes at ≥8000×g (≥10,000 rpm). Buffer RPE (500 μl) was added to the RNeasy spin column and centrifuged for 1 minutes at ≥8000×g (≥10,000 rpm) to wash the spin column membrane. Another 500 μl Buffer RPE was added to the RNeasy spin column and centrifuged for 2 minutes at ≥8000×g (≥10,000 rpm) to wash the spin column membrane. The RNeasy spin column was placed in a new 2 ml collection tube and centrifuged at full speed for 1 min. RNeasy spin column was transferred to a new 1.5 ml collection tube and 30 μl RNase-free water was directly added to the spin column membrane. The spin column was sit at room temperature for 2 minutes and centrifuged for 1 minutes at ≥8000×g (≥10,000 rpm) to elute the RNA.

Protocol for Reverse Transcription with RT$^2$ EZ First Strand Kit (QIAGEN)

Total RNA of 300-1000 ng was diluted with RNase-free H2O to 8 μl and mixed with 6 μl of GE2 (genomic DNA elimination) buffer. The reaction was incubated at 37° C. for 5 min, and immediately placed on ice for 1 minute. 6 μl of the BC5 (RT Master Mix) was added to each 14-μl Genomic DNA Elimination Mixture for a final volume of 20 μl. The reaction was incubated at 42° C. for exactly 15 minutes and then immediately stopped by heating at 95° C. for 5 minutes. Incubation at 37° C., 42° C. and 95° C. was done on a thermal cycle GenAmp PCR System 2700 (Applied Systems). The finished reaction was put on ice until ready to use for real-time PCR, or placed at −20° C. for long-term storage.

Protocol for Reverse Transcription with RT$^2$ First Strand Kit (QIAGEN)

Total RNA of 300-1000 ng was diluted with RNase-free H2O to 8 μl and mixed with 2 μl of GE (genomic DNA elimination) buffer. The reaction was incubated at 42° C. for 5 min, and immediately placed on ice for 1 minute. 10 μl of the RT cocktail (4 μl BC3, 1 μl P2, 2 μl of RE3 and 3 μl of H2O) was added to each 10-μl Genomic DNA Elimination Mixture for a final volume of 20 μl. The reaction was incubated at 42° C. for exactly 15 minutes and then immediately stop the reaction by heating at 95° C. for 5 minutes. Incubation at 42° C. and 95° C. was done on a thermal cycle GenAmp PCR System 2700 (Applied Systems). The finished reaction was put on ice until ready to use for real-time PCR, or placed at −20° C. for long-term storage.

Primers

The primers used to amplify the 88 response genes are listed in the table below and provided in FIG. 6.

| Gene symbol | Primer_F | SEQ ID NO | Primer_R | SEQ ID NO |
|---|---|---|---|---|
| ACSL3 | GGA GTG TTA GGA GCA GCC AG | 1 | CAT ACG ATG TTT GTG ATG CAA C | 2 |
| ADFP | TCC TGT CCA ACA TCC AAG GTG | 3 | TTG CTA GAA GTG AGG AGG CTG | 4 |
| ARFGAP3 | GTG AAA GGT GTT GCT GTT TG | 5 | AAT GAC TGT TCT CCC ATA CAC G | 6 |
| BTBD11 | GTA TCC TCA GAG ATG CTG CGT G | 7 | TGA CAG AGA AAG CAC ACC AAA TG | 8 |
| C20orf46 | CCT CCT TCC CAA TGG CAT C | 9 | AGC TGC CCA GTC TCG TGT TC | 10 |
| C8A | TCA ATC CAT GAC CAG GGA G | 11 | AAT GTT TCA GGT GTC TGC TTG | 12 |
| CASP4 | GAG AGA CAG CAC AAT GGG CTC | 13 | CTT CCG AAA TAC TTC CTC TAG GTG | 14 |
| CD14 | CCA GAA CCT TGT GAG CTG GAC | 15 | CGC TTT AGA AAC GGC TCT AGG | 16 |
| CEBPD | CGC CAT GTA CGA CGA CGA G | 17 | CGC CTT GTG ATT GCT GTT G | 18 |
| CFB | GCT CAC GCC CGA GAC TTT C | 19 | AAC CCA AAT CCT CAT CTT GGA G | 20 |
| CHI3L1 | ACT CGG GAT TAG TAC ACA CTT GTT G | 21 | GTT TGG CTC CTT GGT GAT AG | 22 |
| CITED2 | AAT GGG CGA GCA CAT ACA C | 23 | GTG CCC TCC GTT CAC AGT C | 24 |
| CXADR | CAT AGG TGA AGA CAT GGG TGA AC | 25 | GAG ACT GGT GGG CCA TAA ATA AAT G | 26 |
| DNAJC12 | GAA GGC AAA GGA GAT TCT GAC | 27 | ACT GCT GGA ATG GCA TCG AC | 28 |
| EFNA1 | AGC TGA ATG ACT ACG TGG ACA TC | 29 | ACT GCC AGC GGA CTT GGT C | 30 |
| FBN2 | CAG ATC AGC CTA GAG AGT GTC G | 31 | CCT TTG GTG GAT GCG GAA G | 32 |
| FGA | GAG ACT CCA CAT TTG AAA GCA AG | 33 | CTC TGA CAG GGC GAG ATT TAG | 34 |
| FGB | CAT GCA GCC AAT CCA AAC G | 35 | TTC ATC CAT ACT ACA CCA TCA TC | 36 |
| FILIP1L | CTT CAA ATG CAG CCA GTC TAC | 37 | GAT CTC CAG GTT GCA CAA AG | 38 |

| Gene symbol | Primer_F | SEQ ID NO | Primer_R | SEQ ID NO |
|---|---|---|---|---|
| FKBP14 | GAG GTT GCG GTA AGC CGA G | 39 | GCC ACC AAT CAC TAG GAG C | 40 |
| FLOT2 | GGT GAA GCA GGT CCT CTT G | 41 | CTT CAT CCG CTC AGC CTC TG | 42 |
| FLRT3 | CAG CCT GGA GCA TCT TCC TC | 43 | CAG TAA ATG AAA CCC GCA TCG | 44 |
| FVT1 | ATG AGC ATC AAT TAC CTG GGC AG | 45 | GGC TGT GAA ACC GAA TAA TC | 46 |
| GALNAC4S-6ST | GAG GCT TTG ATG ACC AAG AGC | 47 | GGC CTG TAG AAA TCC CGC AG | 48 |
| GBP2 | GAA CGT ATA AAG GCT GAA TCT GC | 49 | TGA AGT TTA AGA GCG AGG GTC | 50 |
| GK | TGC ATG ACC CTC CAA GTA GAC | 51 | TAG AGG GAA TGG AGC AGG ATG | 52 |
| GLRX | GCA GAG GCT GTG GTC ATG C | 53 | TGC TTT AAT CTT TGC TGG TAG TC | 54 |
| GSDMC | AGA GAT AGG GCT GTG CCT C | 55 | TTA TAC ATA GTG AAA CGC TTA CGT C | 56 |
| GSTT1 | GCC AAG GAC TTC CCA CCT G | 57 | AAT GCT TTG TGG ACT GCT GAG | 58 |
| HAMP | CCA TGT TCC AGA GGC GAA G | 59 | GCA GCA CAT CCC ACA CTT TG | 60 |
| HK1 | AAC GTG TCC TTC CTC CTG TC | 61 | CTG CTT GCC TCT GTG CGT AAC | 62 |
| HP | TAA GGC ATT ATG AAG GCA GC | 63 | CCA GTC GCA TAC CAG GTG TC | 64 |
| HPR | TAG GGC GTG TGG GTT ACG TG | 65 | GTT CGT TCA GTA TGG GCT G | 66 |
| IFITM2 | TCC CAC GTA CTC TAT CTT CCA TTC | 67 | CTG ATG CAG GAC TCG GCT G | 68 |
| IFNGR1 | AGA ATG GAT TGA TGC CTG C | 69 | TTG TCC AAC CCT GGC TTT AAC | 70 |
| IFNGR2 | GGA GCC TGT TTC TTC CTG GTC | 71 | CTC TTC TAT CTG TAA TGG GAT GC | 72 |
| IL1RAP | CTA GAC ACC ATG AGG CAA ATC | 73 | CCT AGT CCA ATA CCA GAT CAG AG | 74 |
| INSIG2 | TGG CAG AAG GAG AGA CAG AG | 75 | CTC GAA TCA TCA AGT TCA CAC TC | 76 |
| KLF9 | GGC CGC CTA CAT GGA CTT C | 77 | AGC TCT TGG CGA TGG TGA C | 78 |
| LBP | TGA GAG TTT GAG GAC AAG AAA GAT G | 79 | CGG AGC TGA GAG CAG AAA TG | 80 |
| LOXL4 | GTG ATG AAC GCC CAG CTA GTG | 81 | CAG TCC GGC CCA GAT TGT AG | 82 |
| LRG1 | CTA GAA CTC TGT TCC TGC TGC | 83 | CAG GTG GTT GAC AGG AGA TG | 84 |
| LY96 | GTT GTT GAA GCT ATT TCT GGG AG | 85 | TTG AAT TAG GTT GGT GTA GGA TG | 86 |
| MATN3 | TCT CCC GGA TAA TCG ACA CTC | 87 | CCT GAC ATG GTG CCT GTT GAC | 88 |
| MBL2 | TGA GGT TTC TAC TGG GAC CAC | 89 | CAG TTC TGC ATA AGT TGA TTG ATA G | 90 |
| MOCOS | GGC TGC TAT ATG ACC GGA G | 91 | TCG ATG AAG GGC TGG ATC AG | 92 |
| NEK6 | GAA CCA CCC AAA TAT CAT CAA G | 93 | CTG CGT CAG CCA ACT CCA G | 94 |
| NRP1 | CAA CAA CTA TGA TAC ACC TGA GC | 95 | TTC CAC TTC ACA GCC CAG C | 96 |
| ORM1 | GCA TTT CGC TCA CTT GCT G | 97 | AGT TCT TCT CAT CGT TCA CGT C | 98 |
| P2RY5 | TTG TAT GGG TGC ATG TTC AGC | 99 | TGT AAG TTG TAG TTT CAT TTC GGA C | 100 |
| PC | CCT TTC AGC CAT CGT CCT TTC | 101 | CCA CCT GAC CCA CCA CTT GTA G | 102 |
| PFKFB3 | GAG CCG CAT CGT GTA CTA C | 103 | CTG GAG GTT GTG CTC GTT CTC | 104 |

| Gene symbol | Primer_F | SEQ ID NO | Primer_R | SEQ ID NO |
|---|---|---|---|---|
| PGK1 | TCT GTT TGA TGA AGA GGG AGC | 105 | CAG CCA GCA GGT ATG CCA G | 106 |
| PHF21A | GGC AGA AGG AGA TGC ACA GC | 107 | TCA GAG TCT ACA GGT TTG GAG AG | 108 |
| PLA2G2A | TGT GTG AGT GTG ATA AGG CTG C | 109 | GAG AGG GAA ATT CAG CAC TGG | 110 |
| PLOD2 | TAG CCG TAT ATC TGG TGG TTA TG | 111 | GTG TAA CTG GTG CAA TGA ACT C | 112 |
| PLSCR4 | AAC TTG CTT CTG TTG CAC TTT AG | 113 | TAC ATC CCA TTC TAC ATA CTG ACT G | 114 |
| PROS1 | ATC GGA TAC AGG CCC TAA GTC | 115 | TTG TCC AAG ACG GCA AGT TG | 116 |
| PVRL2 | AAG CCA AAG AGA CTC AGG TG | 117 | CAG GTA TCA GGG CTG GTT CCT C | 118 |
| RAB43 | GGC CAG GTG ATC TTC CTT AGC | 119 | CTA GAC CAC AAA CCG ACG CAG | 120 |
| RCN1 | CAT GAG GAG AAT GGC CCT G | 121 | CAT CTT TGT CTA ACT TCC CGT C | 122 |
| RHOB | TGC CAT AAG CGA ACT TTG TGC | 123 | GTG TGG TCA GAA TGC TAC TGT C | 124 |
| RNASE4 | TGC AGA GGA CCC ATT CAT TG | 125 | CAA GTT GCA GTA GCG ATC AC | 126 |
| SEMA4B | GGA GAA GCC ATG TGA GCA AG | 127 | CCG TTG CGT AGC CAG AGT C | 128 |
| SERPINA3 | CTC TCA GTA AGG AAC TTG GAA TG | 129 | AGA GCT ACA CAG GGA ATC GCT G | 130 |
| SERPINB13 | GAA AGA AAG GTG AAT CTG CAC | 131 | CAG GAA CTT CTG GGC GTA CAA C | 132 |
| SERPINB3 | CGC GGT CTC GTG CTA TCT G | 133 | GGA AAG GGT GAT TAC AAT GGA AC | 134 |
| SERPINE1 | AGA GAC AGG CAG CTC GGA TTC | 135 | CCA AAG TGC ATT ACA TCC ATC | 136 |
| SLC17A2 | TTG AGT CTG GTT GGA GGA ATG | 137 | TCA GAG GCG GGT AAG GGT C | 138 |
| SNX25 | TCA GTG AGC AAA TGT TGG TTT AC | 139 | CTT CTG ATT GTG GTC GGT G | 140 |
| SOD2 | GGA GCA CGC TTA CTA CCT TC | 141 | CAT TCT CCC AGT TGA TTA CAT TC | 142 |
| SPINK1 | CTG AAG AGA CGT GGT AAG TGC | 143 | CAC TGA GAA GAA AGA TGC CTG | 144 |
| SPP1 | CTG AAA CCC ACA GCC ACA AG | 145 | TGA CTA TCA ATC ACA TCG GAA TG | 146 |
| STAT3 | TGA CAT GGA GTT GAC CTC G | 147 | CTG GAA CCA CAA AGT TAG TAG TTT C | 148 |
| TACC1 | CCT GTG TCG GTG TCC TGT G | 149 | AGG TGA GCA CGG CTG TCT TG | 150 |
| TGM2 | CTT CAC AAG GGC GAA CCA C | 151 | GCG GCA GAC GTA CTC CTC AG | 152 |
| TMEM166 | CTG TAC TTT GTT TCT GGC GTG TG | 153 | GTC GCT GCT GCT CTC TCT GTC | 154 |
| TNFRSF1A | TGT TAC ACT AAT AGA AAC TTG GCA C | 155 | CCT TAG GAC AGT TCA GCT TGC | 156 |
| TOX3 | GAT TGT CAC ATC AGT CAC CAT TG | 157 | TTG CAC CGA AGG ACT CAC TTG | 158 |
| TPST1 | TGG ATG AGG CTG GTG TTA CTG | 159 | ATC TCG ACC ATC AGG AGA AA | 160 |
| TUBB2A | AAC TTC TCA GAT CAA TCG TGC | 161 | AGA CCA TGC TTG AGG ACA AC | 162 |
| TUBB3 | AAC AAC TGG GCC AAG GGT C | 163 | GTC GGG ATA CTC CTC ACG CAC | 164 |
| XBP1 | ATA TCC TGT TGG GCA TTC TG | 165 | GAA AGG GAG GCT GGT AAG AAA C | 166 |
| ZNF684 | AGG ACG GTA GCC GGT ATT C | 167 | GCT CCA AGC TGG GAT CA G | 168 |
| IL6ST | AAG ATT TGA AAC AGT TGG CAT GGA G | 169 | CCT TCA CTG AGG CAT GTA GC | 170 |

| Gene symbol | Primer_F | SEQ ID NO | Primer_R | SEQ ID NO |
|---|---|---|---|---|
| SOCS3 | CCA CCT ACT GAA CCC TCC TCC | 171 | TCT TCC GAC AGA GAT GCT GAA | 172 |
| JUNB | CGA CTA CAA ACT CCT GAA ACC G | 173 | GAA GAG GCG AGC TTG AGA GAC | 174 |
| BCL3 | CAC TCT CTA CCA GAT AAC TGA GGA G | 175 | TAA TAA TTT ACA TCG TGA TCC GTG C | 176 |
| B2M | GCA AGG ACT GGT CTT TCT ATC TC | 177 | ACT AAC TAT CT TGG GCT GTG AC | 178 |
| HPRT1 | GGC CAT CTG CTT AGT AGA GC | 179 | TTA GGA ATG CAG CAA CTG AC | 180 |
| RPL13A | TGA GTG AAA GGG AGC CAG AAG | 181 | TGC AGA GTA TAT GAC CAG GTG | 182 |
| GAPDH | AGA GCA CAA GAG GAA GAG AGA G | 183 | GGT TGA GCA CAG GGT ACT TTA TTG | 184 |
| ACTB | AAT GCT TCT AGG CGG ACT ATG | 185 | CTC CAA CCG ACT GCT GTC AC | 186 |
| TFRC | AGC TGA GAT TCC TGG TTC G | 187 | CAT GCC CTG TAT TCA TAT TGT G | 188 |
| HSP90AB1 | GCA GAG GAA CCC AAT GCT G | 189 | GGA CAC TAT ACA AGG GCA CAA G | 190 |
| PPIA | AAT GGG TTA CTT CTG AAA CAT CAC | 191 | GAC TCC TAC CCT CAG GTG GTC | 192 |

The invention claimed is:

1. A composition for the detection of the regulation status of IL-6/STAT3 signaling pathway in a cell sample or subject, comprising primers that amplify at least 5 of the genes selected from the group consisting of STAT3, SOCS3, IFITM2, CEBPD, JUNB, TUBB2A, IL-6ST, CASP4, PROS1, TNFRSF1A, PVRL2, PHF21A, BCL3, NRP1, GLRX, and TGM2 or an ortholog or variant thereof, wherein said primers include at least five primer pairs selected from the group consisting of:

```
                                  (SEQ ID NO: 147)
TGACATGGAGTTGACCTCG
and
                                  (SEQ ID NO: 148)
CTGGAACCACAAAGTTAGTAGTTTC;

(SEQ ID NO: 171)
CCACCTACTGAACCCTCCTCC
and
                                  (SEQ ID NO: 172)
TCTTCCGACAGAGATGCTGAA;

(SEQ ID NO: 67)
TCCCACGTACTCTATCTTCCATTC
and
                                  (SEQ ID NO: 68)
CTGATGCAGGACTCGGCTG;

(SEQ ID NO: 17)
CGCCATGTACGACGACGAG
and
                                  (SEQ ID NO: 18)
CGCCTTGTGATTGCTGTTG;

(SEQ ID NO: 173)
CGACTACAAACTCCTGAAACCG
and
                                  (SEQ ID NO: 174)
GAAGAGGCGAGCTTGAGAGAC;

(SEQ ID NO: 161)
AACTTCTCAGATCAATCGTGC
and
                                  (SEQ ID NO: 162)
AGACCATGCTTGAGGACAAC;

(SEQ ID NO: 169)
AAGATTTGAAACAGTTGGCATGGAG
and
                                  (SEQ ID NO: 170)
CCTTCACTGAGGCATGTAGC;

(SEQ ID NO: 13)
GAGAGACAGCACAATGGGCTC
and
                                  (SEQ ID NO: 14)
CTTCCGAAATACTTCCTCTAGGTG;

(SEQ ID NO: 115)
ATCGGATACAGGCCCTAAGTC
and
                                  (SEQ ID NO: 116)
TTGTCCAAGACGGCAAGTTG;

(SEQ ID NO: 155)
TGTTACACTAATAGAAACTTGGCAC
and
                                  (SEQ ID NO: 156)
CCTTAGGACAGTTCAGCTTGC;

(SEQ ID NO: 117)
AAGCCAAAGAGACTCAGGTG
and
                                  (SEQ ID NO: 118)
CAGGTATCAGGGCTGGTTCCTC;

(SEQ ID NO: 107)
GGCAGAAGGAGATGCACAGC
and
                                  (SEQ ID NO: 108)
TCAGAGTCTACAGGTTTGGAGAG;

(SEQ ID NO: 175)
CACTCTCTACCAGATAACTGAGGAG
and
                                  (SEQ ID NO: 176)
TAATAATTTACATCGTGATCCGTGC;

(SEQ ID NO: 95)
CAACAACTATGATACACCTGAGC
and
                                  (SEQ ID NO: 96)
TTCCACTTCACAGCCCAGC;

(SEQ ID NO: 53)
GCAGAGGCTGTGGTCATGC
and
```

-continued

```
TGCTTTAATCTTTGCTGGTAGTC;        (SEQ ID NO: 54)
and

CTTCACAAGGGCGAACCAC             (SEQ ID NO: 151)
and

GCGGCAGACGTACTCCTCAG            (SEQ ID NO: 152)
``` wherein at least one of said primers comprises a fluorophore and matched fluorescence quencher.

2. The composition of claim 1, wherein the amplified genes are at least 90% identical to or specifically hybridize to at least 5 genes having accession numbers selected from the group consisting of NM_213662, NM_003955, NM_006435, NM_005195, NM_002229, NM_001069, NM_002184, NM_001225, NM_000313, NM_001065, NM_002856, NM_016621, NM_005178, NM_003873, NM_002064, and NM_004613.

3. The composition of claim 1, which includes primers for amplification of at least 6, at least 7, at least 8, at least 9, at least 10, at least 11, at least 12, at least 13, at least 14, or at least 15 of said genes.

4. The composition of claim 1, wherein the amplified genes are at least 5 genes having accession numbers selected from the group consisting of NM_213662, NM_003955, NM_006435, NM_005195, NM_002229, NM_001069, NM_002184, NM_001225, NM_000313, NM_001065, NM_002856, NM_016621, NM_005178, NM_003873, NM_002064, and NM_004613.

5. The composition of claim 1, which includes primers for amplification of all 16 of said genes.

6. The composition of claim 5, wherein said primers are in contact with the sample to be tested for the level of IL-6/STAT3 pathway activity, and/or are contained in one or more wells of a multi-well reaction vessel.

7. The composition of claim 1, further comprising primers for detecting the expression level of between 1 and 10 housekeeping genes.

8. The composition of claim 1, further comprising a DNA or RNA polymerase.

9. The composition of claim 1, wherein said composition is adapted for effecting PCR, real-time PCR, strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), reverse transcriptase polymerase chain reaction (RT-PCR), or helicase-dependent isothermal DNA amplification.

* * * * *

UNITED STATES PATENT AND TRADEMARK OFFICE
CERTIFICATE OF CORRECTION

Page 1 of 1

PATENT NO. : 10,081,838 B2
APPLICATION NO. : 14/398532
DATED : September 25, 2018
INVENTOR(S) : Wu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 363 days.

Signed and Sealed this
Thirtieth Day of July, 2019

Andrei Iancu
*Director of the United States Patent and Trademark Office*